United States Patent
Nakayama et al.

(10) Patent No.: US 11,873,426 B2
(45) Date of Patent: Jan. 16, 2024

(54) CURABLE COMPOSITION, CURED PRODUCT, OPTICAL MEMBER, LENS, AND COMPOUND

(71) Applicant: FUJIFILM Corporation, Tokyo (JP)

(72) Inventors: Takafumi Nakayama, Kanagawa (JP); Naoyuki Morooka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 430 days.

(21) Appl. No.: 17/132,034

(22) Filed: Dec. 23, 2020

(65) Prior Publication Data

US 2021/0108012 A1    Apr. 15, 2021

Related U.S. Application Data

(63) Continuation of application No. PCT/JP2019/026039, filed on Jul. 1, 2019.

(30) Foreign Application Priority Data

Jul. 2, 2018    (JP) .................. 2018-125971
Feb. 18, 2019   (JP) .................. 2019-026587

(51) Int. Cl.
| | |
|---|---|
| C07D 241/38 | (2006.01) |
| C07D 209/56 | (2006.01) |
| C07D 305/14 | (2006.01) |
| C09J 4/00 | (2006.01) |
| G02B 1/04 | (2006.01) |
| C08F 222/10 | (2006.01) |
| C08F 222/24 | (2006.01) |
| C08F 222/22 | (2006.01) |
| C07D 333/50 | (2006.01) |

(52) U.S. Cl.
CPC .............. *C09J 4/00* (2013.01); *C07D 241/38* (2013.01); *C08F 222/1025* (2020.02); *C08F 222/22* (2013.01); *C08F 222/225* (2020.02); *C08F 222/24* (2013.01); *C08F 222/245* (2020.02); *G02B 1/041* (2013.01); *C07D 209/56* (2013.01); *C07D 305/14* (2013.01); *C07D 333/50* (2013.01)

(58) Field of Classification Search
CPC .. C07D 241/38; C07D 209/56; C07D 305/14; C07D 330/50
See application file for complete search history.

(56) References Cited

U.S. PATENT DOCUMENTS

| | | |
|---|---|---|
| 2013/0237630 A1 | 9/2013 | Morooka et al. |
| 2015/0018445 A1 | 1/2015 | Iizuka et al. |
| 2015/0175731 A1 | 6/2015 | Saitoh |
| 2017/0009138 A1 | 1/2017 | Nakazawa et al. |
| 2017/0174992 A1 | 6/2017 | Ootsuki |
| 2017/0335193 A1 | 11/2017 | Sakamoto et al. |
| 2018/0305486 A1 | 10/2018 | Nakayama et al. |
| 2020/0181061 A1 | 6/2020 | Nakayama et al. |
| 2020/0325367 A1 | 10/2020 | Nakayama et al. |

FOREIGN PATENT DOCUMENTS

| | | |
|---|---|---|
| CN | 107400100 A | 11/2017 |
| CN | 111051363 A | 4/2020 |
| JP | 57-54901 A | 4/1982 |
| JP | 57-66401 A | 4/1982 |
| JP | 60-12502 A | 1/1985 |
| JP | 2008-107767 A | 5/2008 |
| JP | 2009-126011 A | 6/2009 |
| JP | 2012-021068 A | 2/2012 |

(Continued)

OTHER PUBLICATIONS

Office Action dated Oct. 5, 2021 in Japanese Application No. 2020-528847.

(Continued)

*Primary Examiner* — Laura L Stockton
(74) *Attorney, Agent, or Firm* — Sughrue Mion, PLLC

(57) ABSTRACT

The present invention provides a curable composition containing a compound represented by General Formula A and a compound represented by General Formula B.

Ar(̶L-Sp-Pol)$_n$    (General Formula A)

In General Formula A, Ar represents an n-valent group containing a nitrogen-containing fused aromatic ring as a partial structure;

L represents a linking group such as —O— and —C(=O)O—; Sp represents a single bond or a divalent linking group; Pol represents a hydrogen atom or a polymerizable group; n represents 1 or 2; and the compound represented by General Formula A has at least one polymerizable group.

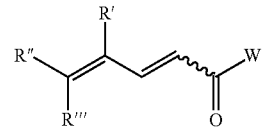

(General Formula B)

In General Formula B, R', R", and R'" are each independently a hydrogen atom or a substituent; R' and R" or R" and R'" may be bonded to each other to form a ring that may have a substituent; and W is a hydrogen atom or a substituent. Using the curable composition of the present invention, it is possible to form a cured product having a small Abbe number, a large partial dispersion ratio, and high light stability.

4 Claims, No Drawings

(56) References Cited

FOREIGN PATENT DOCUMENTS

| | | | |
|---|---|---|---|
| JP | 2012-107191 A | 6/2012 | |
| JP | 2014-043565 A | 3/2014 | |
| JP | 2016-053149 A | 4/2016 | |
| JP | 5898551 B2 | 4/2016 | |
| JP | 2016-081035 A | 5/2016 | |
| JP | 2017-125009 A | 7/2017 | |
| JP | 6857246 B2 | 4/2021 | |
| WO | 2013/018526 A1 | 2/2013 | |
| WO | WO-2016140245 A1 * | 9/2016 | ........... C07C 217/94 |
| WO | 2017/115649 A1 | 7/2017 | |
| WO | 2018/168233 A1 | 9/2018 | |
| WO | 2019/035461 A1 | 2/2019 | |
| WO | 2019/131572 A1 | 7/2019 | |

OTHER PUBLICATIONS

Office Action dated Jul. 20, 2021 from the Japanese Patent Office in JP Application No. 2020-528847.

Office Action dated Aug. 2, 2022, issued in Japanese Application No. 2021-151410.

International Search Report dated Sep. 24, 2019 in International Application No. PCT/JP2019/026039.

Written Opinion of the International Searching Authority dated Sep. 24, 2019 in International Application No. PCT/JP2019/026039.

International Preliminary Report on Patentability dated Jan. 5, 2021 in International Application No. PCT/JP2019/026039.

Sun et al., "Benzoquinone derived 1,3-dithiole-2-ones and thiones", Journal of Chemical Crystallography, 1997, vol. 27, No. 9, pp. 515-526 (12 pages total).

Communication dated Oct. 19, 2022, issued in Chinese Application No. 201980042680.4.

Office Action dated Jun. 21, 2022 in Chinese Application No. 201980042680.4.

"Plastic Aging and Anti-Aging Technology", Peripheral et al., Beijing: China Light Industry Press, 1st edition, 1st print, Nov. 1998, pp. 151-152 (668 pages total).

Office Action dated Jan. 10, 2022 from the China National Intellectual Property Administration in Chinese Application No. 201980042680.4.

* cited by examiner

CURABLE COMPOSITION, CURED PRODUCT, OPTICAL MEMBER, LENS, AND COMPOUND

CROSS-REFERENCE TO RELATED APPLICATIONS

This application is a continuation of PCT International Application No. PCT/JP2019/026039 filed on Jul. 1, 2019, which claims priorities under 35 U.S.C § 119 (a) to Japanese Patent Application Nos. 2018-125971 and 2019-026587 filed on Jul. 2, 2018 and Feb. 18, 2019, respectively, the entire contents of which are incorporated herein by reference.

BACKGROUND OF THE INVENTION

1. Field of the Invention

The present invention relates to a curable composition, a cured product, an optical member, a lens, and a compound.

2. Description of the Related Art

In the related art, glass materials have been used for an optical member of an imaging module such as a camera, a video camera, a mobile phone with a camera, a video phone, or a door phone with a camera. Glass materials have been used preferably because they have various optical characteristics and excellent environmental resistance, but they have a disadvantage in that weight reduction and miniaturization are not easy and workability and productivity are poor. In contrast, resin cured products can be produced in a massive amount and have excellent workability, and therefore they have recently been used in various optical members.

In recent years, a size of an optical member used in an imaging module is required to be reduced in accordance with miniaturization of the imaging module, but in a case of miniaturizing an optical member, a problem of chromatic aberrations occurs. Accordingly, in an optical member formed of a resin cured product, examinations have been conducted regarding adjusting an Abbe number using a monomer of a curable composition and additives, and thereby correcting chromatic aberrations.

For example, WO2017/115649A discloses that it is possible to obtain a curable composition that enables molding of a cured product having a small Abbe number by using a monomer having a heteroatom-containing skeleton similar to a diphenylfluorene skeleton.

Meanwhile, JP2017-125009A discloses a liquid crystal monomer having a quinoxaline ring group or a quinazoline ring group.

SUMMARY OF THE INVENTION

An object of the present invention is to provide a cured product having a small Abbe number (vd), a large partial dispersion ratio (θg, F), and high light stability; and a curable composition for forming the cured product.

In order to achieve the above-mentioned object, the inventors of the present invention have repeatedly conducted examinations using various compounds such as the compound disclosed in WO2017/115649A, which is known to enable formation of a cured product having a small Abbe number and a large partial dispersion ratio. As a result, the inventors of the present invention have found that, in a case of using a compound containing a nitrogen-containing fused aromatic ring in its structure as a monomer, such as the compound disclosed in WO2017/115649A, it is possible to form a cured product with significantly improved light stability by further using an unsaturated carbonyl compound having a specific structure. The inventors of the present invention have further repeatedly conducted examinations, and achieved the above-mentioned object.

That is, the present invention provides the following <1> to <21>.

<1> A curable composition comprising: a compound represented by General Formula A and a compound represented by General Formula B.

 (General Formula A)

In General Formula A, Ar represents an n-valent group containing a nitrogen-containing fused aromatic ring as a partial structure, L represents a single bond, or a linking group selected from the group consisting of —O—, —S—, —C(=O)—, —OC(=O)—, —C(=O)O—, —OC(=O)O—, —NR$_{101}$C(=O)—, —C(=O)NR$_{102}$—, —OC(=O)NR$_{103}$—, —NR$_{104}$C(=O)O—, —SC(=O)—, and —C(=O)S—, where R$_{101}$, R$_{102}$, R$_{103}$, and R$_{104}$ each independently represent -Sp$_3$-Pol$_3$ or a halogen atom; and in a case where there are a plurality of L's, the plurality of L's may be the same as or different from each other, Sp and Sp$_3$ each independently represent a single bond or a divalent linking group; and in a case where there are a plurality of Sp's, the plurality of Sp's may be the same as or different from each other, Pol and Pol$_3$ each independently represent a hydrogen atom or a polymerizable group; and in a case where there are a plurality of Pol's, the plurality of Pol's may be the same as or different from each other, n represents 1 or 2, and the compound represented by General Formula A has at least one polymerizable group.

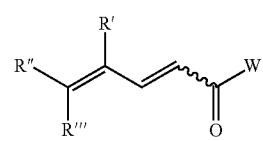 (General Formula B)

In General Formula B, R', R", and R''' are each independently a hydrogen atom or a substituent; R' and R" or R" and R''' may be bonded to each other to form a ring that may have a substituent; and W is a hydrogen atom or a substituent.

<2> The curable composition according to <1>, in which the nitrogen-containing fused aromatic ring is an aromatic ring formed by fusing two 6-membered rings, and contains two or three N's as an element constituting the ring.

<3> The curable composition according to <2>, in which the nitrogen-containing fused aromatic ring is a quinoxaline ring or a quinazoline ring.

<4> The curable composition according to any one of <1> to <3>, in which Ar is a group represented by any of general formulas selected from the group consisting of General Formula A1 and General Formulas A2-1 to A2-5.

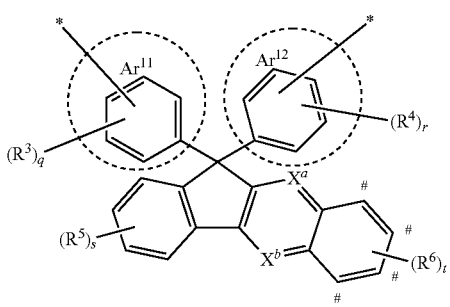

(A1)

In General Formula A1, Ar$^{11}$ and Ar$^{12}$ each independently represent an aromatic hydrocarbon group containing a benzene ring surrounded by a broken line or an aromatic heterocyclic group containing a benzene ring surrounded by a broken line as one of rings constituting a fused ring, one of X$^a$ or X$^b$ represents N and the other represents CH, or both X$^a$ and X$^b$ represent N, any one of CH's at positions # may be N, and R$^3$ to R$^6$ each independently represent a substituent; and q, r, s, and t are each independently an integer of 0 to 4.

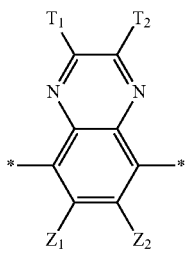

(A2-1)

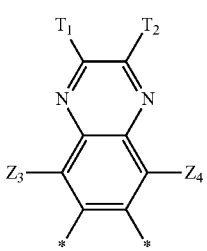

(A2-2)

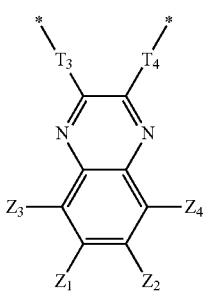

(A2-3)

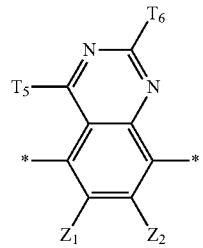

(A2-4)

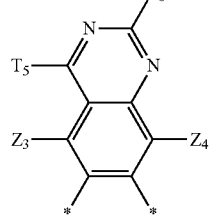

(A2-5)

In General Formulas A2-1 to A2-5, $Z_1$, $Z_2$, $Z_3$, and $Z_4$ each independently represent a hydrogen atom, an aliphatic hydrocarbon group which has 1 to 20 carbon atoms and may have a substituent, an alkoxy group which has 1 to 20 carbon atoms and may have a substituent, an alkoxycarbonyl group which has 1 to 20 carbon atoms and may have a substituent, an alicyclic hydrocarbon group which has 3 to 20 carbon atoms and may have a substituent, an aromatic hydrocarbon group which has 6 to 20 carbon atoms and may have a substituent, a halogen atom, a cyano group, a nitro group, —NR$_{12}$R$_{13}$, SR$_{12}$, or an aromatic heterocyclic ring which may have a substituent; $Z_1$ and $Z_2$ may be bonded to each other to form an aromatic hydrocarbon ring which may have a substituent or an aromatic heterocyclic ring which may have a substituent; and R$_{12}$ and R$_{13}$ each independently represent a hydrogen atom, or an alkyl group which has 1 to 6 carbon atoms and may have a substituent, $T_1$, $T_2$, $T_5$, and $T_6$ each independently represent a halogen atom, a cyano group, a nitro group, -L-Sp$_6$-Pol$_6$, an alicyclic hydrocarbon group which has 3 to 20 carbon atoms and may have a substituent, an aromatic hydrocarbon group which has 6 to 20 carbon atoms and may have a substituent, an aromatic heterocyclic group which may have a substituent, NR$_{12}$R$_{13}$, or SR$_{12}$; and $T_1$ and $T_2$ may be bonded to each other to form an aromatic hydrocarbon ring which may have a substituent or an aromatic heterocyclic ring which may have a substituent, L$_6$ is synonymous with L, Sp$_6$ represents a single bond, or a linking group selected from the group consisting of a linear alkylene group which has 1 to 30 carbon atoms and may have a substituent, and a group in which one or two or more non-adjacent —CH$_2$—'s are substituted by —O—, —S—, —C(=O)—, —OC(=O)—, —C(=O)O—, —OC(=O)O—, —NR$_{201}$C(=O)—, —C(=O)NR$_{202}$—, —OC(=O)NR$_{203}$—, —NR$_{204}$C(=O)O—, —SC(=O)—, or —C(=O)S— in a linear alkylene group which has 2 to 30 carbon atoms and may have a substituent, where R$_{201}$, R$_{202}$, R$_{203}$, and R$_{204}$ each independently represent -Sp$_4$-Pol$_4$ or a halogen atom, Sp$_4$ represents a single bond or a divalent linking group, Pol$_4$ and Pol$_6$ are each independently synonymous with Pol, and T₃ and T₄ each independently represent a divalent aromatic hydrocarbon group which has 6 to 12 carbon atoms and may have a substituent or a divalent aromatic heterocyclic group which may have a substituent.

<5> The curable composition according to <4>, in which Ar is a group represented by General Formula A1, both $X^a$ and $X^b$ are N, and neither of CH's at positions # is N.

<6> The curable composition according to <5>, in which $R^6$ is a methyl group, and t is 1 or 2.

<7> The curable composition according to any one of <4> to <6>, in which Ar is a group represented by General Formula A1, and $Ar^{11}$ and $Ar^{12}$ are a phenyl group.

<8> The curable composition according to <4>, in which Ar is a group represented by any of General Formulas A2-1, A2-2, or A2-3.

<9> The curable composition according to any one of <1> to <8>, in which Sp represents a single bond, or a linking group selected from the group consisting of a linear alkylene group which has 1 to 30 carbon atoms and may have a substituent, a linking group in which the linear alkylene group which has 1 to 30 carbon atoms and may have a substituent and a cycloalkylene group which has 3 to 10 carbon atoms and may have a substituent are bonded to each other through a single bond, —O—, —C(=O)—, —OC(=O)—, —C(=O)O—, —OC(=O)O—, —NR₂₀₁C(=O)—, or —C(=O)NR₂₀₂—, and a group in which one or two or more non-adjacent —CH₂—'s are substituted by —O—, —S—, —C(=O)—, —OC(=O)—, —C(=O)—, —OC(=O)O—, —NR₂₀₁C(=O)—, —C(=O)NR₂₀₂—, —OC(=O)NR₂₀₃—, —NR₂₀₄C(=O)O—, —SC(=O)—, or —C(=O)S— in a linear alkylene group which has 2 to 30 carbon atoms and may have a substituent, where R₂₀₁, R₂₀₂, R₂₀₃, and R₂₀₄ each independently represent -Sp₄-Pol₄ or a halogen atom, Sp₄ represents a single bond or a divalent linking group, and Pol₄ represents a hydrogen atom or a polymerizable group.

<10> The curable composition according to any one of <1> to <9>, in which L is —O—, —OC(=O)—, —OC(=O)O—, or —O—C(=O)NH—.

<11> The curable composition according to any one of <1> to <10>, in which any of Pol's is a (meth)acryloyloxy group.

<12> The curable composition according to any one of <1> to <10>, in which any of Pol's is a methacryloyloxy group.

<13> The curable composition according to any one of <1> to <12>, in which the compound represented by General Formula B is a compound represented by General Formula (B1).

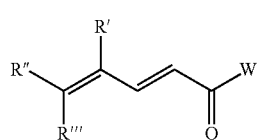

General Formula (B1)

<14> The curable composition according to any one of <1> to <12>, in which the compound represented by General Formula B is a compound represented by General Formula (B2).

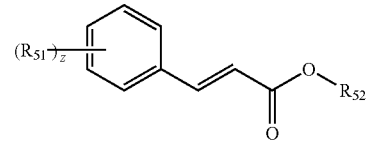

General Formula (B2)

In General Formula (B2), R₅₁ represents a substituent, R₅₂ represents a hydrogen atom or a substituent, and z represents an integer of 0 to 5.

<15> A cured product formed by curing the curable composition according to any one of <1> to <14>.

<16> An optical member comprising the cured product according to <15>.

<17> A lens comprising the cured product according to <15>.

<18> A compound represented by General Formula (A10).

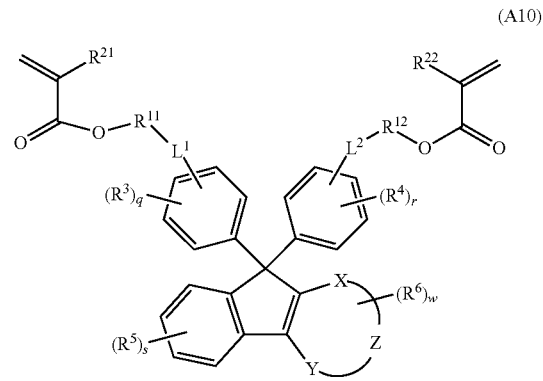

(A10)

In General Formula (A10), X and Y are each independently an oxygen atom, a sulfur atom, a nitrogen atom, or a carbon atom, and at least one of X or Y is an oxygen atom, a sulfur atom, or a nitrogen atom; Z represents an atomic group forming a 5- to 7-membered ring together with X—C=C—Y and containing at least one selected from a carbon atom or a heteroatom; and in X, Y, and Z, a hydrogen atom is bonded to a carbon atom to which $R^6$ is not bonded to form CH, $R^3$ to $R^6$ each independently represent a substituent, and q and r are each independently an integer of 0 to 4, s is an integer of 0 to 4, w is an integer of 0 or more, and a maximum number of w is a maximum number of substituents that may be substituted on the ring formed by X—C=C—Y and Z, $L^1$ and $L^2$ represent an ester bond, $R^{11}$ and $R^{12}$ each independently represent a linear alkylene group having 2 to 20 carbon atoms, or a group in which one or two or more non-adjacent —CH₂—'s are substituted by —O—, —C(=O)—, —OC(=O)—, —C(=O)O—, —OC(=O)O—, or —NH— in the linear alkylene group having 2 to 20 carbon atoms, and $R^{21}$ and $R^{22}$ each independently represent a hydrogen atom or a methyl group.

<19> The compound according to <18>, in which $R^{11}$ and $R^{12}$ each independently represent a linear alkylene group having 2 to 10 carbon atoms, or a group in which one or two or more non-adjacent —CH₂—'s are substituted by —O—, —C(=O)—, —OC(=O)—, —C(=O)O—, —OC(=O)O—, or —NH— in a linear alkylene group having 3 to 15 carbon atoms.

<20> The compound according to <18>, in which both -L$^1$-R$^{11}$— and -L$^2$-R$^{12}$— are —OC(=O)—C$_2$H$_4$—C(=O)—O—C$_2$H$_4$—.

<21> The compound according to any one of <18> to <20>, which is represented by General Formula (A10-1).

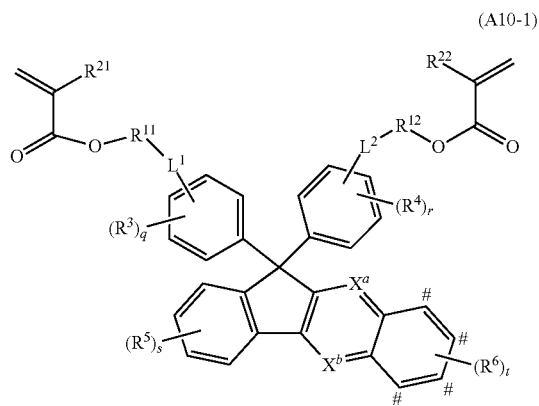

(A10-1)

In General Formula A10-1,
one of X$^a$ or X$^b$ represents N and the other represents CH, or both X$^a$ and X$^b$ represent N,
any one of CH's at positions # may be N,
R$^3$ to R$^6$ each independently represent a substituent; and q, r, s, and t are each independently an integer of 0 to 4,
L$^1$ and L$^2$ represent an ester bond,
R$^{11}$ and R$^{12}$ each independently represent a linear alkylene group having 2 to 20 carbon atoms, or a group in which one or two or more non-adjacent —CH$_2$—'s are substituted by —O—, —C(=O)—, —OC(=O)—, —C(=O)O—, —OC(=O)O—, or —NH— in the linear alkylene group having 2 to 20 carbon atoms, and
R$^{12}$ and R$^{22}$ each independently represent a hydrogen atom or a methyl group.

According to the present invention, a cured product having a small Abbe number (vd), a large partial dispersion ratio (θg, F), and high light stability is provided. Using the cured product according to the aspect of the present invention, it is possible to provide a highly functional optical member and lens. In addition, according to the present invention, a novel compound that can be used for manufacturing the above-mentioned cured product is provided.

DESCRIPTION OF THE PREFERRED EMBODIMENTS

Hereinafter, the present invention will be described in detail. The description of constituent requirements described below can be made based on representative embodiments and specific examples, but the present invention is not limited to such embodiments. Numerical value ranges expressed using "to" in the present specification mean a range including numerical values described before and after "to" as the lower limit value and the upper limit value.

In the present specification, "(meth)acrylate" refers to any one or both of acrylate and methacrylate, and "(meth)acryloyl" refers to any one or both of acryloyl and methacryloyl. A monomer in the present invention is a compound distinguished from oligomers and polymers and having a weight-average molecular weight of 1,000 or less.

In the present specification, in a case where an aliphatic hydrocarbon group is referred to, it represents a group obtained by removing one arbitrary hydrogen atom from a linear or branched alkane, a linear or branched alkene, or a linear or branched alkyne. In the present specification, an aliphatic hydrocarbon group is preferably an alkyl group obtained by removing one arbitrary hydrogen atom from a linear or branched alkane. Examples of alkyl groups include a methyl group, an ethyl group, a propyl group, an isopropyl group, a butyl group, an isobutyl group, a sec-butyl group, a tert-butyl group, a pentyl group, a 1-methylbutyl group, a 3-methylbutyl group, a hexyl group, a 1-methylpentyl group, a 4-methylpentyl group, a heptyl group, a 1-methylhexyl group, a 5-methylhexyl group, a 2-ethylhexyl group, an octyl group, a 1-methylheptyl group, a nonyl group, a 1-methyloctyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, and the like.

An (unsubstituted) aliphatic hydrocarbon group is preferably an alkyl group having 1 to 12 carbon atoms, and is particularly preferably a methyl group or an ethyl group.

In the present specification, in a case where an alkyl group is referred to, it represents a linear or branched alkyl group. Examples of alkyl groups include the above-mentioned examples. The same applies to an alkyl group in groups (for example, an alkoxy group, an alkoxycarbonyl group, and the like) containing an alkyl group.

In addition, examples of linear alkylene groups include groups obtained by removing each hydrogen atom bonded to a terminal carbon from a linear alkyl group among the above-mentioned alkyl groups.

In the present specification, examples of alicyclic hydrocarbon rings include cyclopropane, cyclobutane, cyclopentane, cyclohexane, cycloheptane, cyclooctane, cyclononane, cyclodecane, and the like.

In the present specification, examples of unsaturated hydrocarbon rings include indene, indane, fluorene, and the like.

In the present specification, in a case where an alicyclic hydrocarbon group is referred to, it represents a cycloalkyl group obtained by removing one arbitrary hydrogen atom from cycloalkane. Examples of alicyclic hydrocarbon groups include a cyclopropyl group, a cyclobutyl group, a cyclopentyl group, a cyclohexyl group, a cycloheptyl group, a cyclooctyl group, a cyclononyl group, a cyclodecyl group, and the like, where a cycloalkyl group having 3 to 12 carbon atoms is preferable.

In the present specification, a cycloalkylene group represents a divalent group obtained by removing two arbitrary hydrogen atoms from cycloalkane. Examples of cycloalkylene groups include a cyclohexylene group.

In the present specification, in a case where an aromatic ring is referred to, it means any one or both of an aromatic hydrocarbon ring and an aromatic heterocyclic ring.

In the present specification, an aromatic hydrocarbon ring means an aromatic ring forming a ring only with carbon atoms. An aromatic hydrocarbon ring may be a single ring or a fused ring. An aromatic hydrocarbon ring having 6 to 14 carbon atoms is preferable. Examples of aromatic hydrocarbon rings include a benzene ring, a naphthylene ring, an anthracene ring, a phenanthrene ring, and the like. In the present specification, in a case where an aromatic hydrocarbon ring is bonded to another ring, it is sufficient for the aromatic hydrocarbon ring to be substituted on the other ring as a monovalent or divalent aromatic hydrocarbon group.

In the present specification, in a case where a monovalent group is referred to regarding an aromatic hydrocarbon group, it represents a monovalent group obtained by removing one arbitrary hydrogen atom from an aromatic hydrocarbon ring. A monovalent aromatic hydrocarbon group is preferably an aromatic hydrocarbon group having 6 to 14 carbon atoms. Examples thereof include a phenyl group, a biphenyl group, a 1-naphthyl group, a 2-naphthyl group, a 1-anthracenyl group, a 2-anthracenyl group, a 3-anthracenyl group, a 4-anthracenyl group, a 9-anthracenyl group, a 1-phenanthryl group, a 2-phenanthryl group, a 3-phenanthryl group, a 4-phenanthryl group, a 9-phenanthryl group, and the like. Among the examples, a phenyl group is preferable.

In the present specification, in a case where a divalent group is referred to regarding an aromatic hydrocarbon group, it represents a divalent group obtained by removing one arbitrary hydrogen atom from the above-mentioned monovalent aromatic hydrocarbon group. Examples of divalent aromatic hydrocarbon groups include a phenylene group, a biphenylene group, a naphthylene group, a phenanthrylene group, and the like, where a phenylene group is preferable, and a 1,4-phenylene group is more preferable.

In the present specification, an aromatic heterocyclic ring means an aromatic ring in which a ring is formed by carbon atoms and heteroatoms. Examples of heteroatoms include an oxygen atom, a nitrogen atom, a sulfur atom, and the like. An aromatic heterocyclic ring may be a single ring or a fused ring, and the number of elements constituting the ring is preferably 5 to 20, and more preferably 5 to 14. The number of heteroatoms in the elements constituting the ring is not particularly limited, but it is preferably 1 to 3 and is more preferably 1 or 2. Examples of aromatic heterocyclic rings include a furan ring, a thiophene ring, a pyrrole ring, an imidazole ring, an isothiazole ring, an isoxazole ring, a pyridine ring, a pyrazine ring, a quinoline ring, a benzofuran ring, a benzothiazole ring, a benzoxazole ring, a nitrogen-containing fused aromatic ring to be described later, and the like. In the present specification, in a case where an aromatic heterocyclic ring is bonded to another ring, it is sufficient for the aromatic heterocyclic ring to be substituted on the other ring as a monovalent or divalent aromatic heterocyclic group.

In the present specification, in a case where a monovalent group is referred to regarding an aromatic heterocyclic group, it represents a monovalent group obtained by removing one arbitrary hydrogen atom from an aromatic heterocyclic ring. Examples of monovalent aromatic heterocyclic groups include a furyl group, a thienyl group, a pyrrolyl group, an imidazolyl group, an isothiazolyl group, an isoxazolyl group, a pyridyl group, a pyrazinyl group, a quinolyl group, a benzofuranyl group (preferably a 2-benzofuranyl group), a benzothiazolyl group (preferably a 2-benzothiazolyl group), a benzoxazolyl group (preferably a 2-benzoxazolyl group), and the like. Among the examples, a furyl group, a thienyl group, a benzofuranyl group, a benzothiazolyl group, and a benzoxazolyl group are preferable, and a 2-furyl group and a 2-thienyl group are more preferable.

In the present specification, in a case where a divalent aromatic heterocyclic group is referred to, it represents a divalent group obtained by removing two arbitrary hydrogen atoms from an aromatic heterocyclic ring. Examples thereof include a divalent group obtained by removing one arbitrary hydrogen atom from the above-mentioned (monovalent) aromatic heterocyclic group.

In the present specification, examples of halogen atoms include a fluorine atom, a chlorine atom, a bromine atom, and an iodine atom.

<Curable Composition>

A curable composition of the embodiment of the present invention contains a compound represented by General Formula A and a compound represented by General Formula B. The curable composition of the embodiment of the present invention may further contain other components in addition to the compound represented by General Formula A and the compound represented by General Formula B. Specific examples of other components may include (meth) acrylate monomers (monomers other than the compound represented by General Formula A and the compound represented by General Formula B), polymerization initiators (at least one selected from a photoradical polymerization initiator or a thermal radical polymerization initiator), polymers and monomers which are other than the components described above, and additives such as dispersants, plasticizers, thermal stabilizers, and mold release agents.

[Compound Represented by General Formula A]

The compound represented by General Formula A contains a nitrogen-containing fused aromatic ring and a polymerizable group in its structure. Using the compound represented by General Formula A enables a small Abbe number (vd) and a large partial dispersion ratio (θg, F) of a cured product formed from the curable composition containing this compound. Because the above-mentioned compound having a nitrogen-containing fused aromatic ring such as a quinoxaline ring or a quinazoline ring has absorption in a near ultraviolet region, this compound exhibits anomalous dispersibility of refractive index, thereby improving a chromatic aberration correction performance in a case of being used as a compound lens. Furthermore, in the cured product formed from the curable composition containing the compound represented by General Formula A, a change in refractive index due to a wet heat environment is small.

$$Ar\text{-}(\text{-}L\text{-}Sp\text{-}Pol)_n \quad \text{(General Formula A)}$$

In General Formula A, Ar represents an n-valent group containing a nitrogen-containing fused aromatic ring as a partial structure, L represents a single bond, or a linking group selected from the group consisting of —O—, —S—, —C(=O)—, —OC(=O)—, —C(=O)O—, —OC(=O)O—, —NR$_{101}$C(=O)—, —C(=O)NR$_{102}$—, —OC(=O)NR$_{103}$—, —NR$_{104}$C(=O)O—, —SC(=O)—, and —C(=O)S—, where R$_{101}$, R$_{102}$, R$_{103}$, and R$_{104}$ each independently represent -Sp$_3$-Pol$_3$ or a halogen atom; and in a case where there are a plurality of L's, the plurality of L's may be the same as or different from each other, Sp and Sp$_3$ each independently represent a single bond or a divalent linking group; and in a case where there are a plurality of Sp's, the plurality of Sp's may be the same as or different from each other, Pol and Pol$_3$ each independently represent a hydrogen atom or a polymerizable group; and in a case where there are a plurality of Pol's, the plurality of Pol's may be the same as or different from each other, n represents 1 or 2, and the compound represented by General Formula A has at least one polymerizable group.

Hereinafter, each substituent will be described.

In General Formula A, Ar is an n-valent group containing a nitrogen-containing fused aromatic ring as a partial structure. The nitrogen-containing fused aromatic ring is an aromatic ring (aromatic heterocyclic ring) formed by fusing two or more rings, and is an aromatic ring containing nitrogen as an element constituting the ring. The nitrogen-containing fused aromatic ring contained in Ar is preferably a bicyclic type, and is more preferably an aromatic ring in which two 6-membered rings are fused. Furthermore, it is sufficient that the nitrogen-containing fused aromatic ring contained in Ar contain one or more N's as an element constituting the ring, and it preferably contains two or more N's, more preferably contains two or three N's, and even more preferably contains 2 N's. The nitrogen-containing fused aromatic ring may contain a hetero element other than N such as O or S, but it preferably does not contain it. Examples of nitrogen-containing fused aromatic rings include an isoquinoline ring, a quinoline ring, a phthalazine ring, a naphthyridine ring, a quinoxaline ring, a quinazoline ring, a cinnoline ring, a pteridine ring, a benzoxazole ring, a benzothiazole ring, a pyridoxazole ring, a pyridothiazole ring, an indole ring, an isoindole ring, a benzimidazole ring, and the like. Among the examples, a quinoxaline ring and a quinazoline ring are preferable.

Examples of n-valent groups containing the nitrogen-containing fused aromatic ring represented by Ar as a partial structure include an n-valent group consisting of a nitrogen-containing fused aromatic ring which may have a substituent. Positions of bonds of the n-valent group are not particularly limited, and it is sufficient for n positions to be selected from the group consisting of any carbon atom on the nitrogen-containing fused aromatic ring, and any atom (preferably carbon atom) in a substituent substituting on the nitrogen-containing fused aromatic ring. In a case where n is 2, positions of bonds is preferably two positions selected from the group consisting of any carbon atom on the nitrogen-containing fused aromatic ring, or two positions selected from the group consisting of any atom in the substituent.

For example, in a case where the nitrogen-containing fused aromatic ring is a quinoxaline ring or a quinazoline ring, positions of bonds on the quinoxaline ring or the quinazoline ring are not particularly limited, but they are preferably two positions selected from a 5-position to a 8-position, and are more preferably a 5-position and a 8-position, or a 6-position and a 7-position. Furthermore, in a case where a bond is on a substituent substituting on the quinoxaline ring or the quinazoline ring, the substituent is preferably an aromatic hydrocarbon group or aromatic heterocyclic group which may have a substituent, is more preferably an aromatic hydrocarbon group which has 6 to 12 carbon atoms and may have a substituent, is even more preferably a phenyl group which may have a substituent (a phenylene group which may have a substituent as a state having a bond), and is particularly preferably a phenyl group (a phenylene group as a state having a bond). In a case where a phenyl group has a bond, a position thereof is preferably at a 4-position (where a bonding position to a quinoxaline ring or a quinazoline ring is a 1-position) (that is, a 1,4-phenylene group).

In the n-valent group consisting of the nitrogen-containing fused aromatic ring which may have a substituent, substituents bonded to adjacent carbon atoms in the nitrogen-containing fused aromatic ring may be bonded to each other to form a ring that may have a substituent. Examples of such structures include a structure represented by General Formula A1.

Ar preferably contains a structure in which one or two groups selected from the group consisting of an aromatic hydrocarbon ring which may have a substituent and an aromatic heterocyclic ring which may have a substituent are directly bonded to a nitrogen-containing fused aromatic ring, more preferably contains a structure in which one or two groups selected from the group consisting of aromatic hydrocarbon rings which have 6 to 12 carbon atoms and may have a substituent are directly bonded to a nitrogen-containing fused aromatic ring, and even more preferably contains a structure in which one or two benzene rings are directly bonded to a nitrogen-containing fused aromatic ring.

Examples of n-valent groups containing the nitrogen-containing fused aromatic ring represented by Ar as a partial structure include a group represented by General Formula A1 and a group represented by any of General Formulas A2-1, A2-2, A2-3, A2-4, or A2-5.

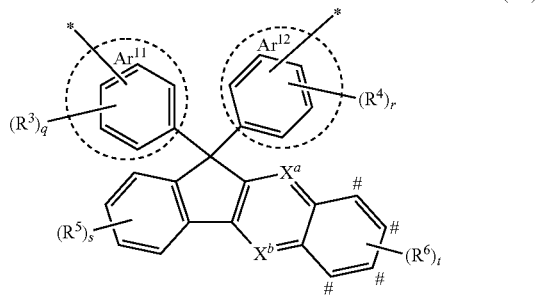

(A1)

In General Formula A1, $Ar^{11}$ and $Ar^{12}$ each independently represent an aromatic hydrocarbon group containing a benzene ring surrounded by a broken line or an aromatic heterocyclic group containing a benzene ring surrounded by a broken line as one of rings constituting a fused ring, one of $X^a$ or $X^b$ represents N and the other represents CH, or both $X^a$ and $X^b$ represent N, any one of CH's at positions # may be N, and $R^3$ to $R^6$ each independently represent a substituent; and q, r, s, and t are each independently an integer of 0 to 4.

Furthermore, * indicates a bonding position with Pol-Sp-L-.

Both $X^a$ and $X^b$ are preferably N. Furthermore, neither of CH's at positions # is preferably N. That is, General Formula A1 is preferably General Formula A1-2.

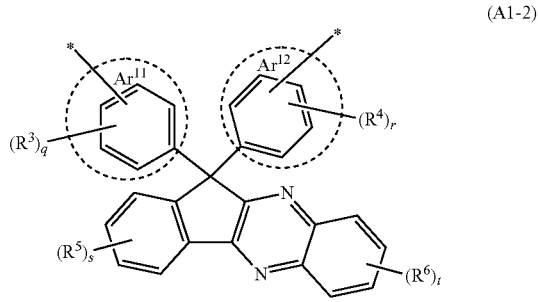

(A1-2)

In General Formula A1-2, $Ar^{11}$ and $Ar^{12}$ each independently represent an aromatic hydrocarbon group containing a benzene ring surrounded by a broken line or an aromatic heterocyclic group containing a benzene ring surrounded by a broken line as one of rings constituting a fused ring. $Ar^{11}$ and $Ar^{12}$ are each independently preferably an aromatic hydrocarbon group (aryl group) containing a benzene ring surrounded by a broken line. In a case where $Ar^{11}$ and $Ar^{12}$ are aromatic hydrocarbon groups containing a benzene ring surrounded by a broken line, the aromatic hydrocarbon group is preferably an aromatic hydrocarbon group having 6 to 18 carbon atoms, is more preferably an aromatic hydrocarbon group having 6 to 14 carbon atoms, and is particularly preferably an aromatic hydrocarbon group having 6 to 10 carbon atoms. Among them, $Ar^{11}$ and $Ar^{12}$ are each independently particularly preferably a phenyl group composed of only a benzene ring surrounded by a broken line. In a case where $Ar^{11}$ and $Ar^{12}$ are aromatic heterocyclic groups (heteroaryl groups) containing a benzene ring surrounded by a broken line as a fused ring, the aromatic heterocyclic group is preferably an aromatic heterocyclic group having a 9- to 14-membered ring, and is more preferably an aromatic heterocyclic group having a 9- or 10-membered ring. In a case where $Ar^{11}$ and $Ar^{12}$ are aromatic heterocyclic groups containing a benzene ring surrounded by a broken line as a fused ring, examples of heteroatoms include a nitrogen atom, an oxygen atom, and a sulfur atom.

Substituents represented by $R^3$ to $R^6$ are not particularly limited, and examples thereof include a halogen atom, a halogenated alkyl group, an alkyl group, an alkenyl group, an acyl group, a hydroxy group, a hydroxyalkyl group, an alkoxy group, an aromatic hydrocarbon group, an aromatic heterocyclic group, an aliphatic cyclic group, a cyano group, and the like. The substituents represented by $R^3$ to $R^6$ are preferably a halogen atom, an alkyl group, an alkoxy group, an aromatic hydrocarbon group, or a cyano group; are more preferably a halogen atom, an alkyl group having 1 to 5 carbon atoms, an alkoxy group having 1 to 5 carbon atoms, a phenyl group, or a cyano group; and are particularly preferably a halogen atom, a methyl group, a methoxy group, a phenyl group, or a cyano group. Among them, $R^3$ and $R^4$ are each independently preferably a methyl group or a methoxy group; and $R^5$ is preferably a halogen atom, a methyl group, or a methoxy group, and is more preferably a methyl group. $R^6$ is preferably a halogen atom, a methyl group, or a methoxy group, and is more preferably a methyl group.

It is preferable that q and r be each independently 0 or 1, and it is more preferable that both q and r be each independently 0. It is preferable that s and t be each independently 0 to 2, it is more preferable that s be 0 and t be 1 or 2, and it is even more preferable that s be 0 and t be 2. A substitution position of $R^6$ in a case where t is 1 is preferably a 6-position or 7-position of a formed quinoxaline ring, and substitution positions of $R^6$ in a case where t is 2 are preferably a 6-position and a 7-position of a formed quinoxaline ring.

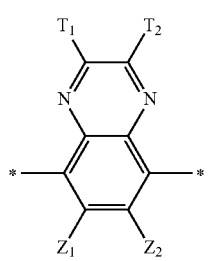

(A2-1)

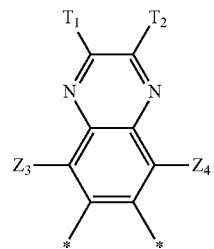

(A2-2)

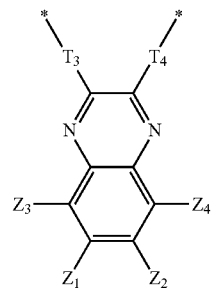

(A2-3)

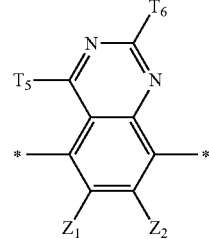

(A2-4)

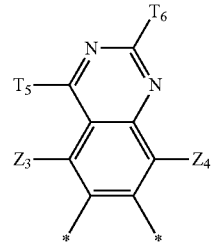

(A2-5)

In General Formulas A2-1 to A2-5, $Z_1$, $Z_2$, $Z_3$, and $Z_4$ represent monovalent groups, and each independently represent a hydrogen atom, an aliphatic hydrocarbon group which has 1 to 20 carbon atoms and may have a substituent, an alkoxy group which has 1 to 20 carbon atoms and may have a substituent, an alkoxycarbonyl group which has 1 to 20 carbon atoms and may have a substituent, an alicyclic hydrocarbon group which has 3 to 20 carbon atoms and may have a substituent, an aromatic hydrocarbon group which has 6 to 20 carbon atoms and may have a substituent, a halogen atom, a cyano group, a nitro group, $-NR_{12}R_{13}$, $SR_{12}$, or an aromatic heterocyclic group which may have a substituent; $Z_1$ and $Z_2$ may be bonded to each other to form an aromatic hydrocarbon ring which may have a substituent or an aromatic heterocyclic ring which may have a substituent; and $R_{12}$ and $R_{13}$ each independently represent a hydrogen atom, or an alkyl group which has 1 to 6 carbon atoms and may have a substituent. Furthermore, * indicates a bonding position with Pol-Sp-L-.

In the description of the respective substituents in General Formulas A2-1 to A2-5, a substituent in a case of referring to the phrase "may have a substituent" is not particularly limited as long as the substituent is not highly desorbable (easily decomposable) such as an acid chloride (—COCl) or —OTf(-O—SO$_2$CF$_3$). Examples thereof include a halogen atom, a hydroxy group, an amino group, a cyano group, a nitro group, a nitroso group, a carboxy group, an alkyl group having 1 to 6 carbon atoms, an alkoxy group having 1 to 6 carbon atoms, an alkoxycarbonyl group having 1 to 6 carbon atoms, an alkylcarbonyloxy group having 1 to 6 carbon atoms, an alkylcarbonyl group having 1 to 6 carbon atoms, an alkylsulfinyl group having 1 to 6 carbon atoms, an alkylsulfonyl group having 1 to 6 carbon atoms, a fluoroalkyl group having 1 to 6 carbon atoms, an alkylsulfanyl group having 1 to 6 carbon atoms, an N-alkylamino group having 1 to 6 carbon atoms, an N,N-dialkylamino group having 2 to 12 carbon atoms, an N-alkylsulfamoyl group having 1 to 6 carbon atoms, an N,N-dialkylsulfamoyl group having 2 to 12 carbon atoms, and the like. Among these substituents, a halogen atom, a hydroxy group, an alkyl group having 1 to 6 carbon atoms, an alkoxy group having 1 to 6 carbon atoms, and a fluoroalkyl group having 1 to 6 carbon atoms are preferable, and a fluorine atom, a chlorine atom, a bromine atom, a hydroxy group, a methyl group, a methoxy group, and a fluoromethyl group are more preferable.

It is preferable that $Z_1$ and $Z_2$ be each independently a hydrogen atom or an aliphatic hydrocarbon group which has 1 to 20 carbon atoms and may have a substituent, or $Z_1$ and $Z_2$ be bonded to each other to form an aromatic hydrocarbon ring which may have a substituent. It is more preferable that $Z_1$ and $Z_2$ be each independently a hydrogen atom or a methyl group, or $Z_1$ and $Z_2$ be bonded to each other to form a benzene ring.

It is preferable that $Z_3$ and $Z_4$ be each independently a hydrogen atom or an aliphatic hydrocarbon group which has 1 to 20 carbon atoms and may have a substituent, and it is more preferable that $Z_3$ and $Z_4$ be each independently a hydrogen atom or a methyl group.

In General Formulas A2-1 and A2-2 and General Formulas A2-4 and A2-5, $T_1$, $T_2$, $T_5$, and $T_6$ represent monovalent groups and each independently represent a halogen atom, a cyano group, a nitro group, -L$_6$-Sp$_6$-Pol$_6$, an alicyclic hydrocarbon group which has 3 to 20 carbon atoms and may have a substituent, an aromatic hydrocarbon group which has 6 to 20 carbon atoms and may have a substituent, an aromatic heterocyclic group which may have a substituent, NR$_{12}$R$_{13}$, or SR$_{12}$.

L$_6$ is synonymous with L, but the left side is bonded to a quinoxaline ring or a quinazoline ring, and the right side is bonded to Sp$_6$ in the description of a linking group to be exemplified. L$_6$ is preferably a single bond, —O—, —OC(=O)—, or —C(=O)O—, and is more preferably a single bond.

Sp$_6$ represents a single bond, or a linking group selected from the group consisting of a linear alkylene group which has 1 to 30 carbon atoms and may have a substituent, and a group in which one or two or more non-adjacent —CH$_2$—'s are substituted by —O—, —S—, —C(=O)—, —OC(=O)—, —C(=O)O—, —OC(=O)O—, —NR$_{201}$C(=O)—, —C(=O)NR$_{202}$—, —OC(=O)NR$_{203}$—, —NR$_{204}$C(=O)O—, —SC(=O)—, or —C(=O)S— in a linear alkylene group which has 2 to 30 carbon atoms and may have a substituent. R$_{201}$, R$_{202}$, R$_{203}$, and R$_{204}$ each independently represent -Sp$_4$-Pol$_4$ or a halogen atom; Sp$_4$ represents a single bond or a divalent linking group; and Pol$_4$ and Pol$_6$ are each independently synonymous with Pol.

Sp$_6$ is preferably a linking group selected from the group consisting of a linear alkylene group which has 1 to 10 carbon atoms and may have a substituent, and a group in which one or two or more non-adjacent —CH$_2$—'s are substituted by —O—, —C(=O)—, —OC(=O)—, —C(=O)O—, or —OC(=O)O— in the linear alkylene group which has 1 to 10 carbon atoms and may have a substituent.

Examples of polymerizable groups represented by Pol$_6$ include the same polymerizable groups as those for Pol to be described later, and a preferable range of polymerizable groups is also the same. A hydrogen atom is preferable as Pol$_6$.

Examples of -L$_6$-Sp$_6$-Pol$_6$ include a hydrogen atom, examples to be described later as a group represented by -L-Sp-Pol, and a group selected from the group consisting of an aliphatic hydrocarbon group which has 1 to 20 carbon atoms and may have a substituent and an alkoxy group which has 1 to 20 carbon atoms and may have a substituent, or a group having a polymerizable group at a terminal of these groups.

It is preferable that $T_1$ and $T_2$ be each independently an aromatic hydrocarbon group which has 6 to 20 carbon atoms and may have a substituent, an aromatic heterocyclic group which may have a substituent, an aliphatic hydrocarbon group which has 1 to 20 carbon atoms and may have a substituent, or the examples to be described later as the group represented by -L-Sp-Pol. It is more preferable that $T_1$ and $T_2$ be each independently a phenyl group which may have a substituent, a biphenyl group, a naphthyl group, an alkyl group having 1 to 6 carbon atoms, a furyl group, or a thienyl group. It is even more preferable that $T_1$ and $T_2$ be each independently a phenyl group, a 4-biphenyl group, a 1-naphthyl group, a 2-naphthyl group, an alkyl group having 1 to 6 carbon atoms, a 2-furyl group, or a 2-thienyl group. It is particularly preferable that $T_1$ and $T_2$ be each independently a phenyl group.

$T_1$ and $T_2$ may be the same as or different from each other, but they are preferably the same as each other. However, it is also preferable that one of $T_1$ or $T_2$ be a phenyl group which may have a substituent and the other be a hydrogen atom or an alkyl group having 1 to 4 carbon atoms.

At least one of $T_1$ or $T_2$ is preferably not a hydrogen atom. In addition, at least one of $T_1$ or $T_2$ is preferably an aromatic hydrocarbon group which has 6 to 20 carbon atoms and may have a substituent, or an aromatic heterocyclic group which may have a substituent.

$T_1$ and $T_2$ may be bonded to each other to form an aromatic hydrocarbon ring which may have a substituent or an aromatic heterocyclic ring which may have a substituent. In this case, $T_1$ and $T_2$ are preferably bonded to each other to form an aromatic hydrocarbon ring which may have a substituent, are more preferably bonded to each other to form benzene which may have a substituent, naphthylene which may have a substituent, anthracene which may have a substituent, or phenanthrene which may have a substituent, and are even more preferably bonded to each other to form benzene or phenanthrene.

It is preferable that $T_5$ and $T_6$ be each independently an aromatic hydrocarbon group which has 6 to 20 carbon atoms and may have a substituent, an aromatic heterocyclic group which may have a substituent, an aliphatic hydrocarbon group which has 1 to 20 carbon atoms and may have a substituent, or the examples to be described later as the group represented by -L-Sp-Pol. It is more preferable that $T_5$ and $T_6$ be each independently a hydrogen atom, a phenyl group which may have a substituent, a biphenyl group, a naphthyl group, an alkyl group having 1 to 6 carbon atoms, a furyl group, or a thienyl group. It is even more preferable that $T_5$ and $T_6$ be each independently a hydrogen atom, a phenyl group, a 4-biphenyl group, a 1-naphthyl group, a 2-naphthyl group, an alkyl group having 1 to 6 carbon atoms, a 2-furyl group, or a 2-thienyl group. It is particularly preferable that $T_5$ and $T_6$ be each independently a hydrogen atom or a phenyl group.

$T_5$ and $T_6$ may be the same as or different from each other. It is also preferable that $T_6$ be any of the above-mentioned preferable substituents and $T_5$ be a hydrogen atom.

At least one of $T_5$ or $T_6$ is preferably not a hydrogen atom. In addition, at least one of $T_5$ or $T_6$ is preferably an aromatic hydrocarbon group which has 6 to 20 carbon atoms and may have a substituent, or an aromatic heterocyclic group which may have a substituent.

In General Formula A2-3, $T_3$ and $T_4$ represent divalent linking groups, and each independently represent a divalent aromatic hydrocarbon group which has 6 to 12 carbon atoms and may have a substituent or a divalent aromatic heterocyclic group which may have a substituent. As $T_3$ and $T_4$, a divalent aromatic hydrocarbon group which has 6 to 12 carbon atoms and may have a substituent is preferable, a divalent aromatic hydrocarbon group having 6 to 10 carbon atoms is more preferable, a phenylene group is even more preferable, and a 1,4-phenylene group is particularly preferable.

$T_3$ and $T_4$ may be the same as or different from each other, but they are preferably the same as each other.

Ar, which is any group represented by General Formulas A2-1 to A2-5, is more preferably any group represented by General Formulas A2-1 to A2-3. The reason for this is because then, synthesis is easy and raw materials can be obtained at low costs.

In General Formula A, L's each independently represent a single bond, or a linking group selected from the group consisting of —O—, —S—, —C(=O)—, —OC(=O)—, —C(=O)O—, —OC(=O)O—, —NR$_{101}$C(=O)—, —C(=O)NR$_{102}$—, —OC(=O)NR$_{103}$—, —NR$_{104}$C(=O)O—, —SC(=O)—, and —C(=O)S—. In the description of the above-mentioned linking group, the left side is bonded to Ar, and the right side is bonded to Sp. R$_{101}$, R$_{102}$, R$_{103}$, and R$_{104}$ each independently represent -Sp$_3$-Pol$_3$ or a halogen atom. L's are each independently preferably —O—, —OC(=O)—, —C(=O)O—, —OC(=O)O—, —NR$_{101}$C(=O)—, —C(=O)NR$_{102}$—, —OC(=O)NR$_{103}$—, or —NR$_{104}$C(=O)O—, more preferably —O—, —OC(=O)—, —OC(=O)O—, or —OC(=O)NR$_{103}$—, and even more preferably —O— or —OC(=O)—. In a case where there are a plurality of L's, the plurality of L's may be the same as or different from each other, but they are preferably the same as each other.

Sp and Sp$_3$ each independently represent a single bond or a divalent linking group. Examples of divalent linking groups include the following linking groups, and linking groups selected from the group consisting of combinations of two or more linking groups of the following linking groups.

That is, examples of Sp and Sp$_3$ which are divalent linking groups include a linear alkylene group that may have a substituent; a cycloalkylene group that may have a substituent; a divalent aromatic hydrocarbon group that may have a substituent; a divalent aromatic heterocyclic group that may have a substituent; a linking group in which two or more linking groups selected from the group consisting of a linear alkylene group that may have a substituent, a cycloalkylene group that may have a substituent, a divalent aromatic hydrocarbon group that may have a substituent, and a divalent aromatic heterocyclic group that may have a substituent are bonded through a single bond or a linking group selected from the group consisting of —O—, —S—, —C(=O)—, —OC(=O)—, —C(=O)O—, —OC(=O)O—, —NR$_{201}$C(=O)—, —C(=O)NR$_{202}$—, —OC(=O)NR$_{203}$—, —NR$_{204}$C(=O)O—, —SC(=O)—, and —C(=O)S—; and the like.

In the description of the linking groups, the left side is bonded to L or N (in the case of Sp$_3$), and the right side is bonded to Pol or Pol$_3$ (in the case of Sp$_3$).

R$_{201}$, R$_{202}$, R$_{203}$, and R$_{204}$ each independently represent -Sp$_4$-Pol$_4$ or a halogen atom. Sp$_4$ and Pol$_4$ are respectively synonymous with Sp and Pol. Examples of polymerizable groups represented by Pol$_4$ include the same polymerizable groups as those for Pol to be described later, and a preferable range of the polymerizable groups is also the same. Pol$_4$ is preferably a hydrogen atom. -Sp$_4$-Pol$_4$ is preferably a hydrogen atom or an alkyl group which has 1 to 4 carbon atoms and may have a substituent, and is more preferably a hydrogen atom or an unsubstituted alkyl group having 1 to 4 carbon atoms.

R$_{201}$, R$_{202}$, R$_{203}$, and R$_{204}$ each independently preferably are a hydrogen atom, an unsubstituted alkyl group having 1 to 4 carbon atoms, or a halogen atom.

A substituent in a case of referring to the phrase "may have a substituent" regarding substituents in Sp and Sp$_3$ is not particularly limited as long as the substituent is not highly desorbable (easily decomposable) such as an acid chloride (—COCl) or -OTf(-O—SO$_2$CF$_3$). Examples thereof include an alkyl group, a cycloalkyl group, an alkoxy group, an acyl group, an acyloxy group, an alkoxycarbonyl group, an amide group, an amino group, a halogen atom, a nitro group, and a cyano group, and a substituent selected from the group consisting of groups composed of a combination of two or more substituents among the above-mentioned substituents. The substituent may be a group represented by -Sp$_5$-Pol$_5$. Sp$_5$ and Pol$_5$ are respectively synonymous with Sp and Pol, and preferable ranges thereof are also the same. The number of substituents is not particularly limited, and there may be 1 to 4 substituents. In a case where there are two or more substituents, the two or more substituents may be the same as or different from each other.

A divalent linking group represented by Sp is preferably a linking group selected from the group consisting of a linear alkylene group which has 1 to 30 carbon atoms and may have a substituent, a linking group in which the linear alkylene group which has 1 to 30 carbon atoms and may have a substituent and a cycloalkylene group which has 3 to 10 carbon atoms and may have a substituent are bonded to each other through a single bond, —O—, —C(=O)—, —OC(=O)—, —C(=O)O—, —OC(=O)O—, —NR$_{201}$C(=O)—, or —C(=O)NR$_{202}$—, and a group in which one or two or more non-adjacent —CH$_2$—'s are substituted by —O—, —S—, —C(=O)—, —OC(=O)—, —C(=O)O—, —OC(=O)O—, —NR$_{201}$C(=O)—, —C(=O)NR$_{202}$—, —OC(=O)NR$_{203}$—, —NR$_{204}$C(=O)O—, —SC(=O)—, or —C(=O)S— in a linear alkylene group which has 2 to 30 carbon atoms and may have a substituent.

In Sp which is a group in which —CH$_2$— is substituted by another divalent group selected from the group consisting of —O—, —S—, —C(=O)—, —OC(=O)—, —C(=O)O—, —OC(=O)O—, —NR$_{201}$C(=O)—, —C(=O)NR$_{202}$—, —OC(=O)NR$_{203}$—, —NR$_{204}$C(=O)O—, —SC(=O)—, and —C(=O)S— in a linear alkylene group having 2 to 30 carbon atoms, it is preferable that the other divalent group be not directly bonded to L. That is, a moiety substituted by the other divalent group is preferably not an L side terminal of Sp.

It is more preferable that the divalent linking group represented by Sp be a linking group selected from the group consisting of a linear alkylene group which has 1 to 20 carbon atoms and may have a substituent, a linking group in which the linear alkylene group which has 1 to 20 carbon atoms and may have a substituent and a cycloalkylene group which has 3 to 6 carbon atoms and may have a substituent are bonded to each other through —O—, —C(=O)—, —OC(=O)—, —C(=O)O—, or —OC(=O)O—, and a group in which one or two or more non-adjacent —CH$_2$—'s are substituted by —O—, —C(=O)—, —OC(=O)—, —C(=O)O—, —OC(=O)O—, —NR$_{201}$C(=O)—, —C(=O)NR$_{202}$—, —OC(=O)NR$_{203}$—, or —NR$_{204}$C(=O)O— in a linear alkylene group which has 2 to 20 carbon atoms and may have a substituent. It is even more preferable that the divalent linking group represented by Sp be a linking group selected from the group consisting of a linear alkylene group which has 1 to 10 carbon atoms and may have a substituent, a linking group in which the linear alkylene group which has 1 to 10 carbon atoms and may have a substituent and a cycloalkylene group which has 3 to 6 carbon atoms and may have a substituent are bonded to each other through —O—, —C(=O)—, —OC(=O)—, or —C(=O)O—, and a group in which one or two or more non-adjacent —CH$_2$—'s are substituted by —O—, —C(=O)—, —OC(=O)—, or —C(=O)O— in a linear alkylene group which has 2 to 10 carbon atoms and may have a substituent. It is particularly preferable that the divalent linking group represented by Sp be a linking group selected from the group consisting of a linear alkylene group which has 1 to 10 carbon atoms and has no substituent or has a methyl group as a substituent, a linking group in which the linear alkylene group which has 1 to 10 carbon atoms and has no substituent or has a methyl group as a substituent and an unsubstituted cycloalkylene group which has 3 to 6 carbon atoms are bonded to each other through —O—, —C(=O)—, —OC(=O)—, or —C(=O)O—, and a group in which one or two or more non-adjacent —CH$_2$—'s are substituted by —O—, —C(=O)—, —OC(=O)—, or —C(=O)O— in a linear alkylene group which has 2 to 10 carbon atoms and which has no substituent or has a methyl group as a substituent.

In a case where there are a plurality of Sp's, the plurality of Sp's may be the same as or different from each other, but they are preferably the same as each other.

In Pol-Sp-L-, Sp and L are preferably not a single bond at the same time, and both Sp and L are more preferably not a single bond.

In General Formula A, -L-Sp- is preferably —O-Sp$_{Alk1}$- or —O—C(=O)—Sp$_{Alk2}$-C(=O)—O—S$_{Alk3}$—, and is more preferably —O—C(=O)—Sp 2-C(=O)—O-Sp$_3$-. Sp$_{Alk1}$, Sp$_{Alk2}$, and Sp$_{Alk3}$ each independently represent a linear alkylene group which has 1 to 10 carbon atoms and has no substituent or has a methyl group as a substituent. Sp$_{Alk1}$, Sp$_{Alk2}$, and Sp$_{Alk3}$ are each preferably a linear alkylene group which has 2 to 6 carbon atoms and has no substituent or has a methyl group as a substituent, they are each more preferably a linear alkylene group which has 2 to 4 carbon atoms and has no substituent or has a methyl group as a substituent, and they are each particularly preferably an ethylene group which has no substituent or has a methyl group as a substituent.

A divalent linking group represented by Sp$_3$ is preferably a linear alkylene group which has 1 to 10 carbon atoms and may have a substituent, is more preferably a linear alkylene group which has 1 to 5 carbon atoms and may have a substituent, is even more preferably a linear alkylene group which has 1 to 3 carbon atoms and may have a substituent, and is particularly preferably an unsubstituted linear alkylene group having 1 to 3 carbon atoms.

Pol and Pol$_3$ each independently represent a hydrogen atom or a polymerizable group. Examples of polymerizable groups include polymerizable groups represented by Formulas Pol-1 to Pol-6.

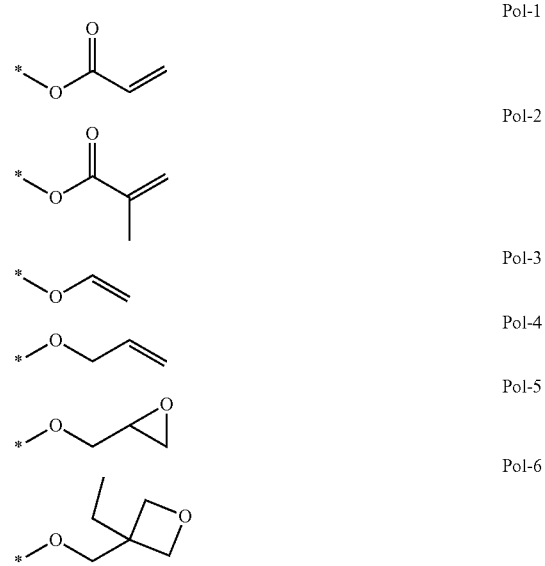

*indicates a bonding position

Among them, (meth)acryloyloxy groups (Pol-1 and Pol-2) are preferable.

Pol is preferably a polymerizable group, and is more preferably a (meth)acryloyloxy group. In particular, a lens formed from a curable composition containing a compound in which Pol is a methacryloyloxy group has high moisture-heat resistance.

In a case where there are a plurality of Pol's, the plurality of Pol's may be the same as or different from each other, but they are preferably the same as each other.

The compound represented by General Formula A has at least one polymerizable group. The compound represented by General Formula A preferably has at least two polymerizable groups. The compound represented by General Formula A preferably has a polymerizable group as at least Pol, and more preferably has a polymerizable group only as Pol.

Pol$_3$ is preferably a hydrogen atom.

-Sp$_3$-Pol$_3$ is preferably a hydrogen atom or an alkyl group which has 1 to 4 carbon atoms and may have a substituent, and is more preferably a hydrogen atom or an unsubstituted alkyl group having 1 to 4 carbon atoms.

Examples of specific structures of Pol-Sp-L- include the following structures.

In the compound represented by General Formula A, in a case where there are a plurality of Pol-Sp-L-'s, the plurality of Pol-Sp-L-'s may be the same as or different from each other, but they are preferably the same.

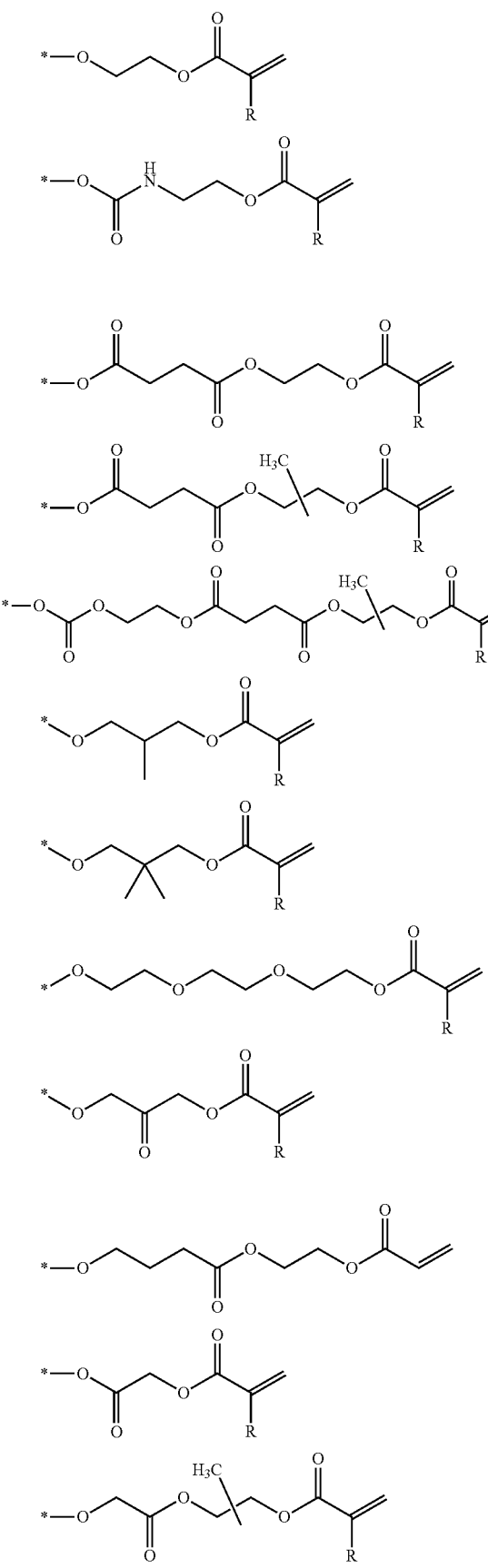

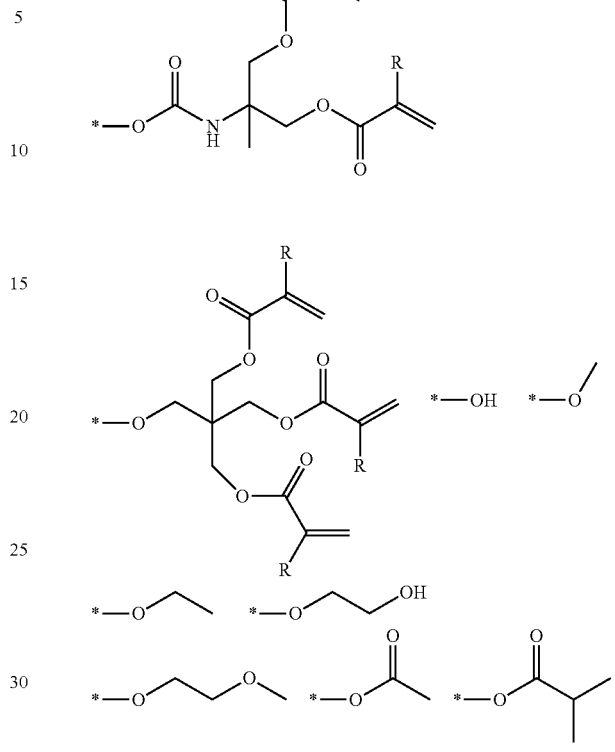

(R is a hydrogen atom or a methyl group. In addition, * indicates a bonding position with Ar.)

In the present specification, the following structures show that two partial structures in which methyl groups are respectively bonded to any one carbon of an ethylene group are mixed.

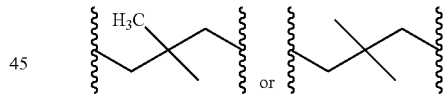

As described above, in a case where the compound represented by General Formula A has a structure in which a substituent is substituted on a linear alkylene group, structural isomers having different substitution positions of the substituent may be present. The compound represented by General Formula A may be a mixture of such structural isomers.

The compound represented by General Formula A is preferably a non-liquid crystalline compound.

Specific examples of the compound represented by General Formula A which is preferably used in the curable composition of the embodiment of the present invention are listed below, but examples are not limited to the following compounds. In the following structural formulas, Me represents a methyl group, Et represents an ethyl group, iPr represents an i-propyl group, nPr represents an n-propyl group, nBu represents an n-butyl group, and tBu represents a t-butyl group.

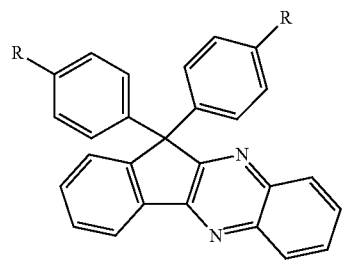
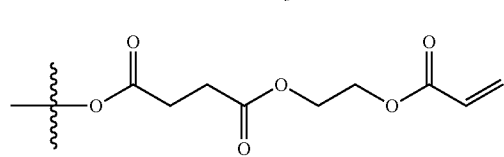 (A-1)
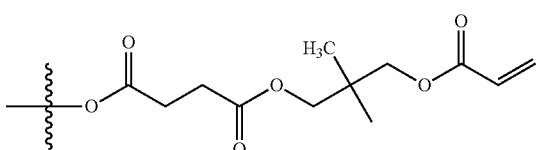 (A-2)
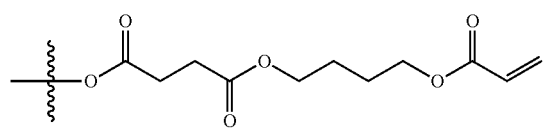 (A-3)
(A-4)
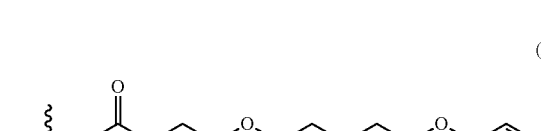 (A-5)
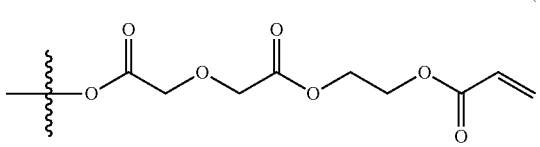 (A-6)
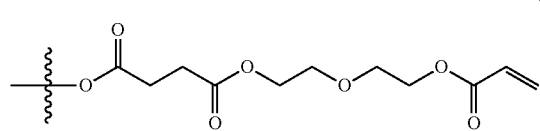 (A-7)
(A-8)
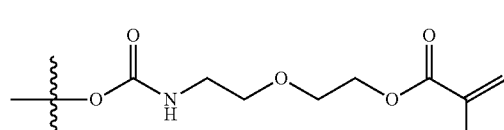 (A-9)
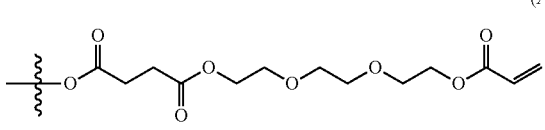 (A-10)
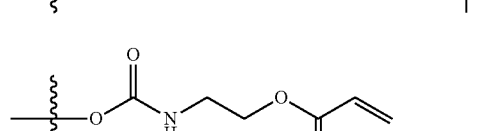 (A-11)
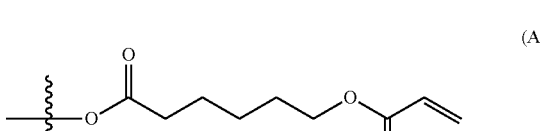 (A-12)
R = 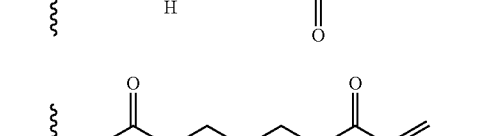 (A-13)
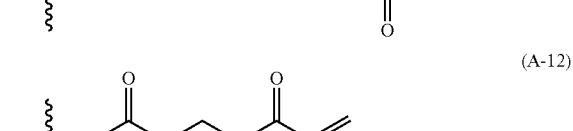 (A-14)
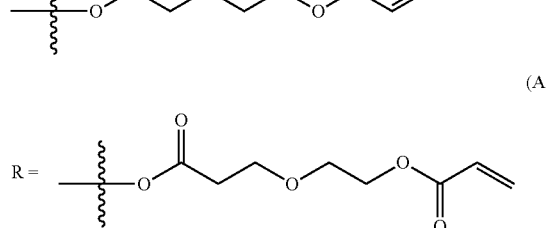 (A-15)
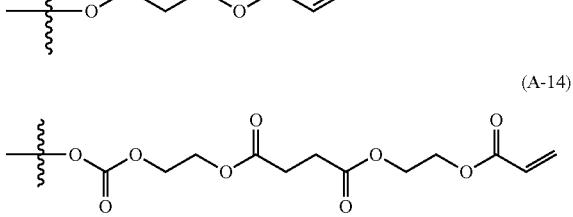 (A-16)
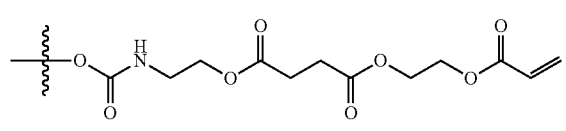 (A-17)
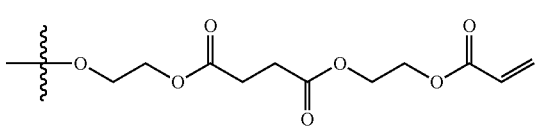 (A-18)
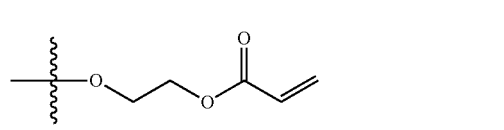

-continued
(A-19) 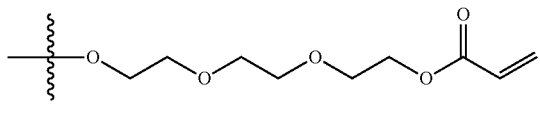
(A-20) 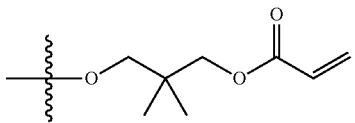
(A-21) 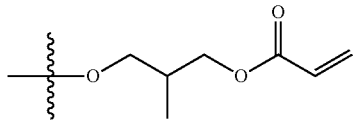
(A-22) 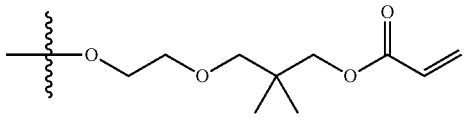
(A-23) 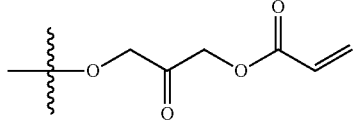
(A-24) 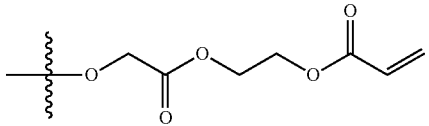
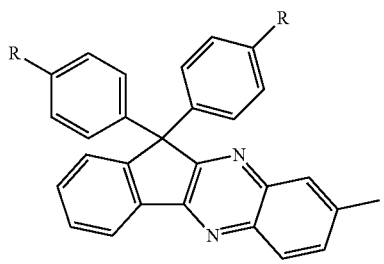
(A-25) R = 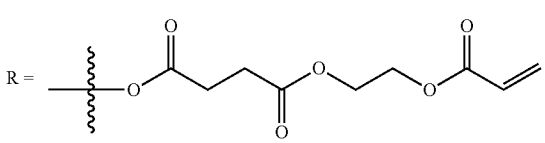
(A-26) R = 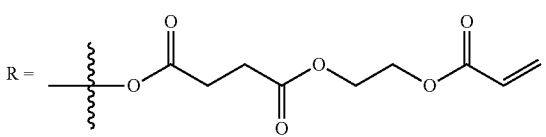
(A-27) R = 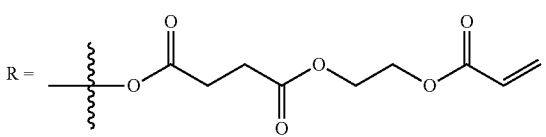
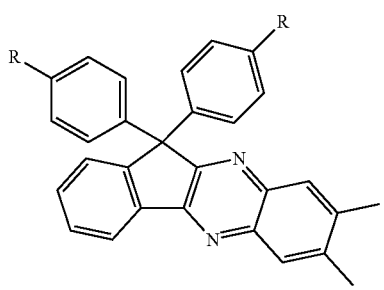
(A-28) R = 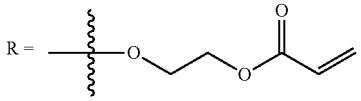
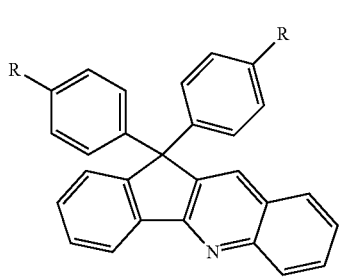

-continued
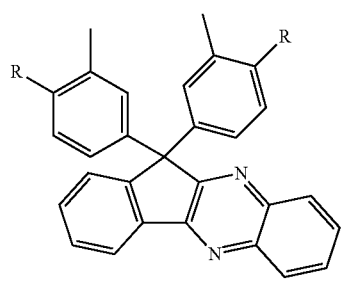
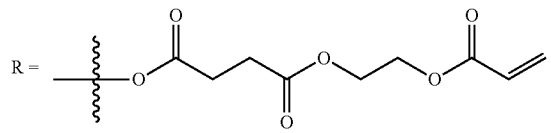
(A-29)
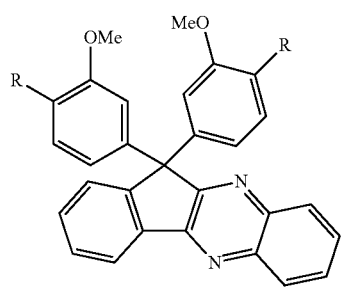
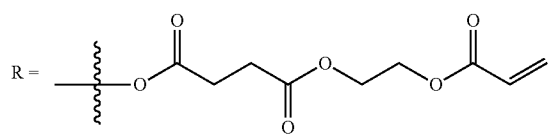
(A-30)
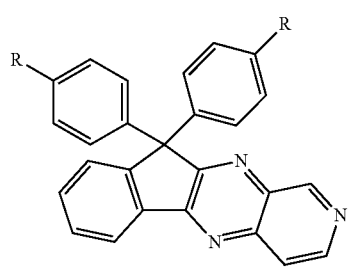
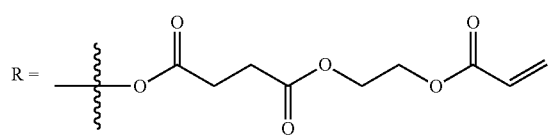
(A-31)
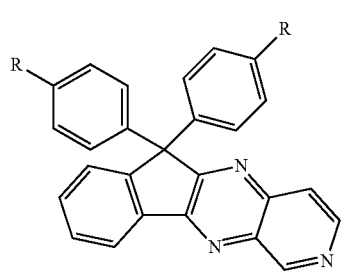
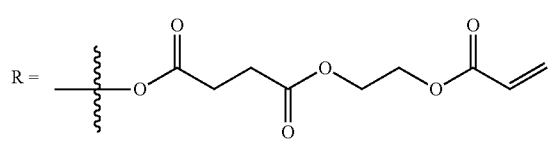
(A-32)
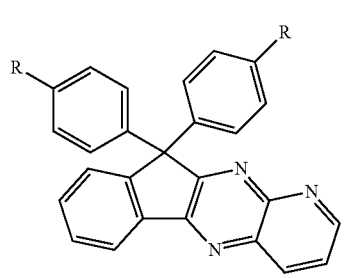
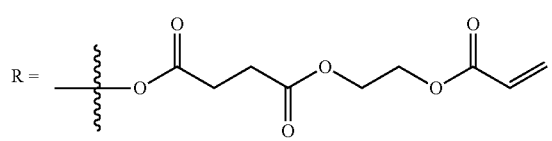
(A-33)

-continued
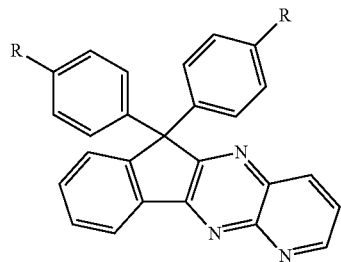
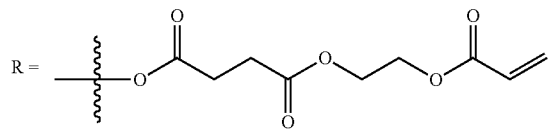
(A-34)
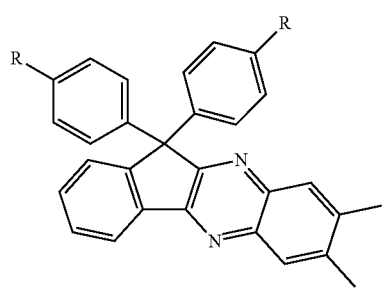
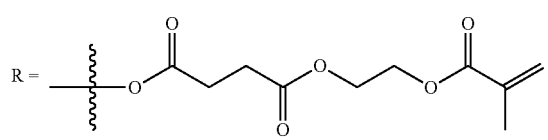
(A-35)
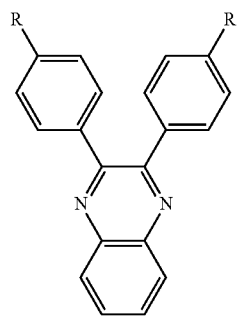
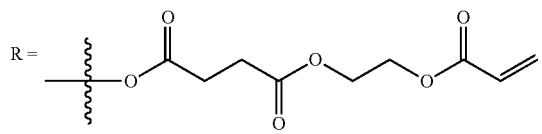
(I-1)   R =
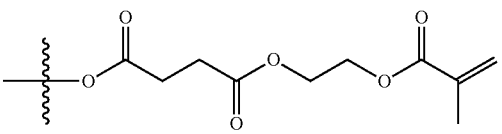
(I-2)
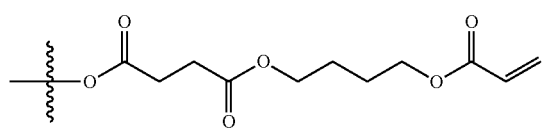
(I-3)
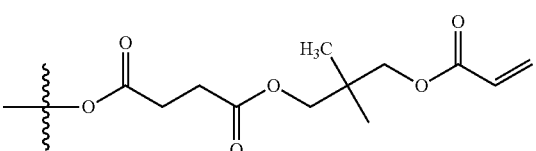
(I-4)
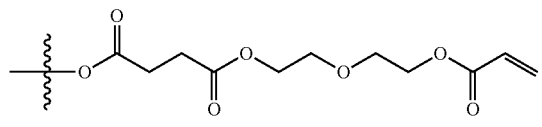
(I-5)
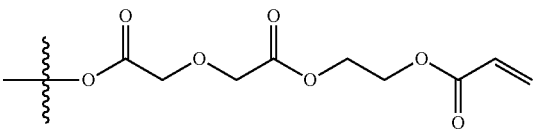
(I-6)
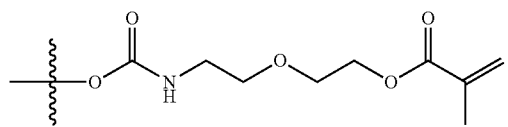
(I-7)
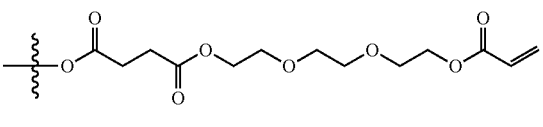
(I-8)

-continued
(I-9) 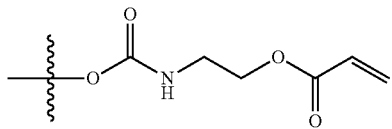
(I-10) 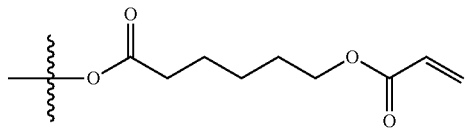
(I-11) 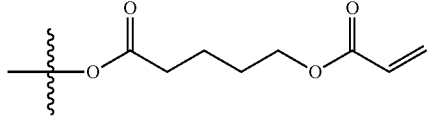
(I-12) 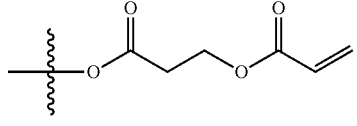
(I-13) R = 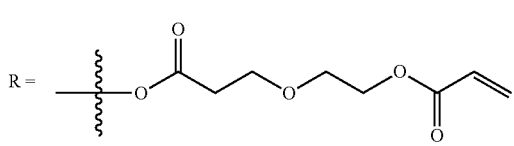
(I-14) 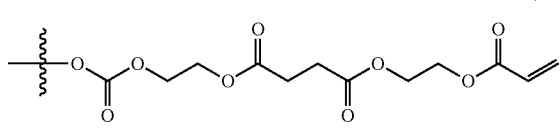
(I-15) 
(I-16) 
(I-17) 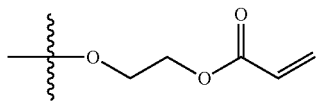
(I-18) 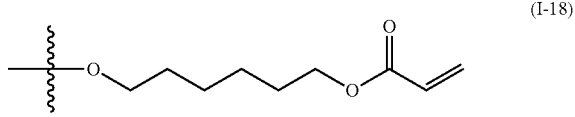
(I-19) 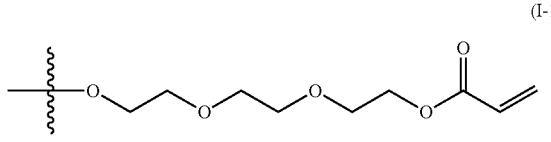
(I-20) 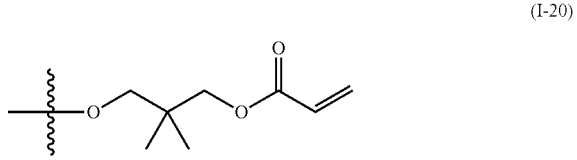
(I-21) 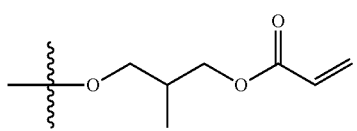
(I-22) 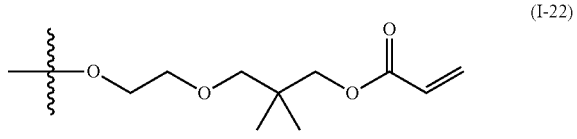
(I-23) 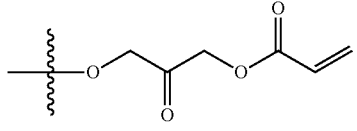
(I-24) 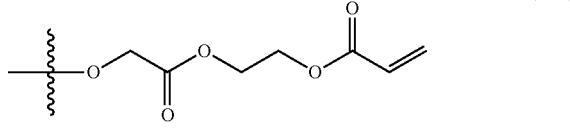
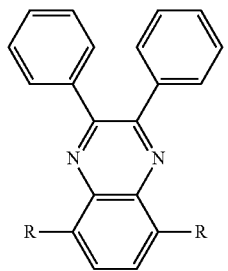
(II-1) R = 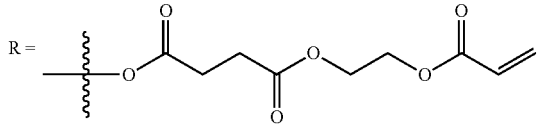
(II-2) 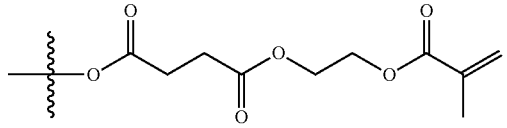

-continued
(II-3)
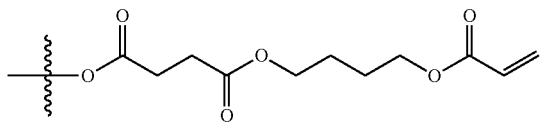
(II-4)
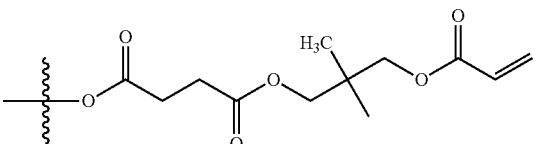
(II-5)
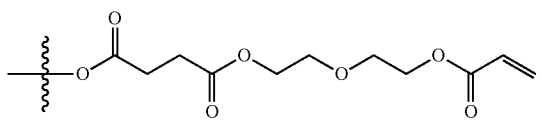
(II-6)
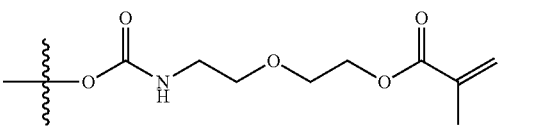
(II-7)
R = 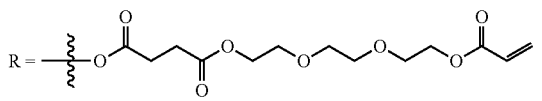
(II-8)
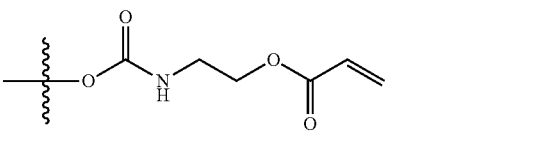
(II-9)
(II-10)
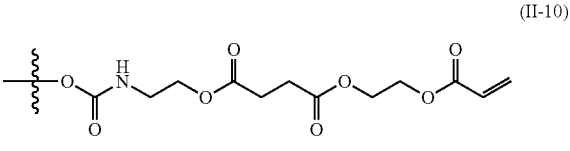
(II-11)
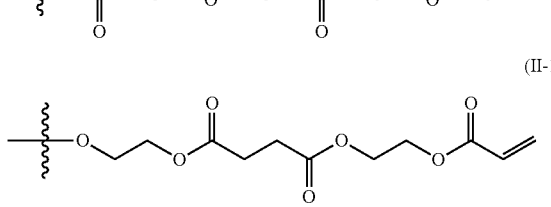
(II-12)
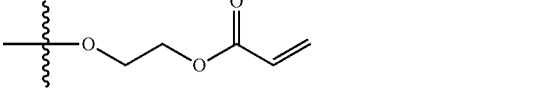
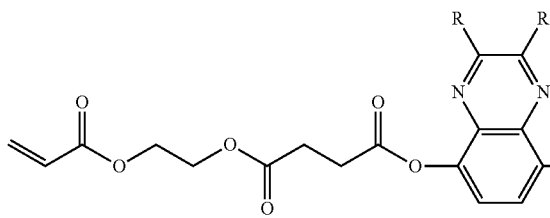
(III-1)
R = 
(III-2)
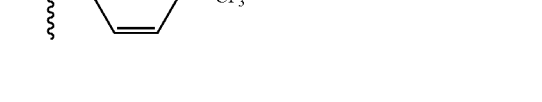
(III-3)
(III-4)
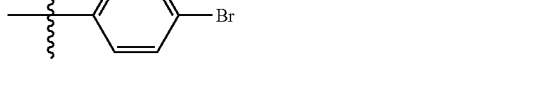
(III-5)
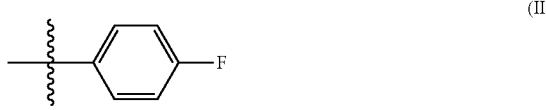
(III-6)
(III-7)
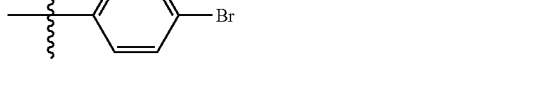
(III-8)
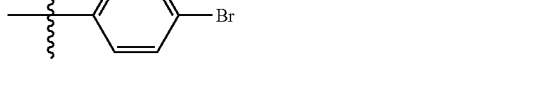

-continued (III-9), (III-10), (III-11), (III-13), (III-14), (III-15), (III-16), (III-17), (III-18), (III-19), (III-20), (III-12), (III-21)

(III-22)
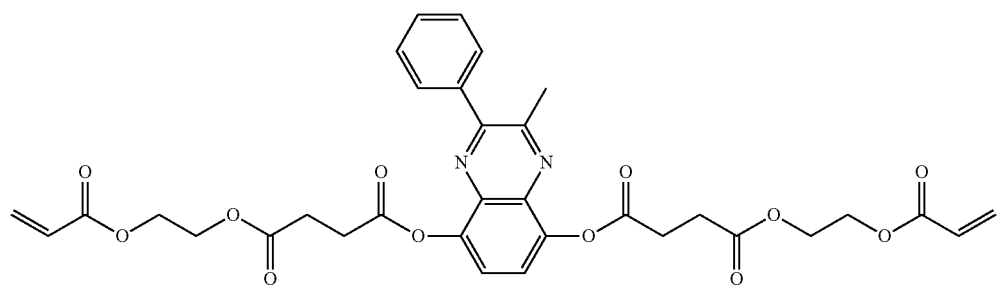
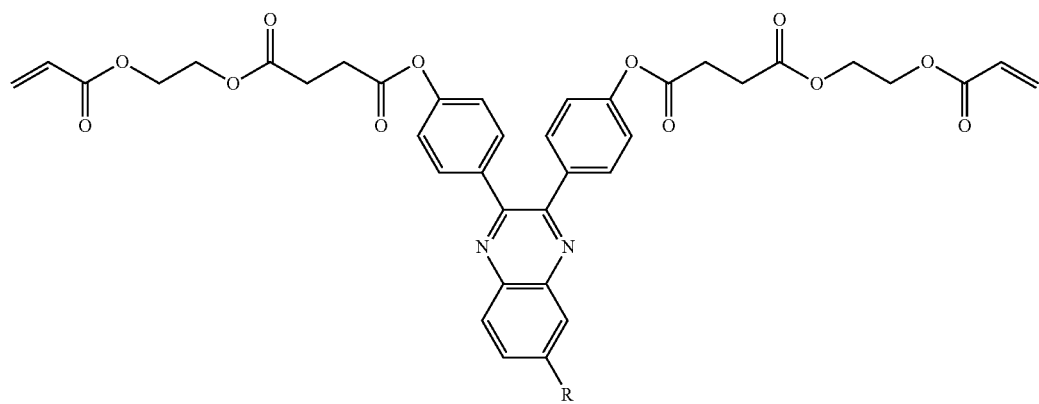
| | | | |
|---|---|---|---|
| (IV-1) 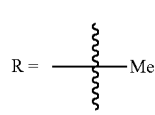 R = —Me | | (IV-2) 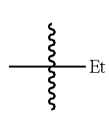 —Et | |
| (IV-3) 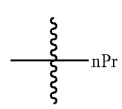 —nPr | | (IV-4) 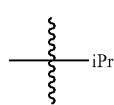 —iPr | |
| (IV-5) 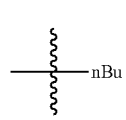 —nBu | | (IV-6) 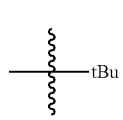 —tBu | |
| (IV-7) 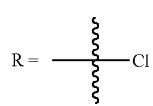 R = —Cl | | (IV-8) 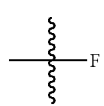 —F | |
| (IV-9) 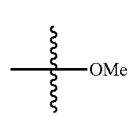 —OMe | | (IV-10) 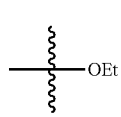 —OEt | |
| (IV-11) 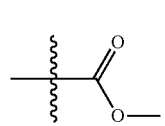 | | | |

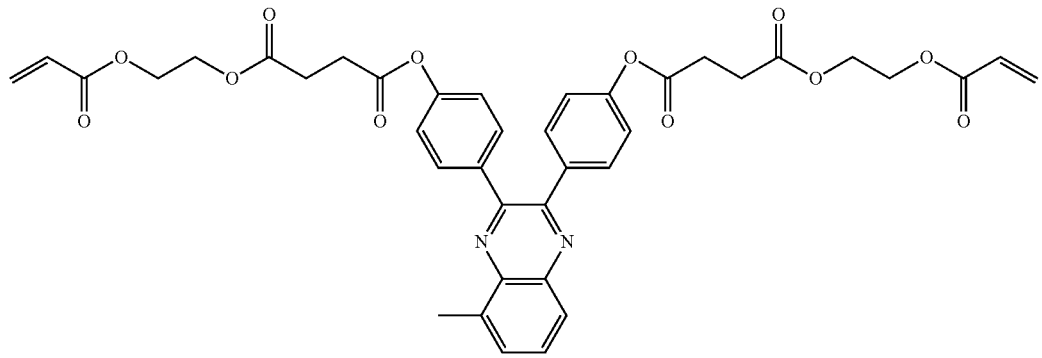
(IV-12)
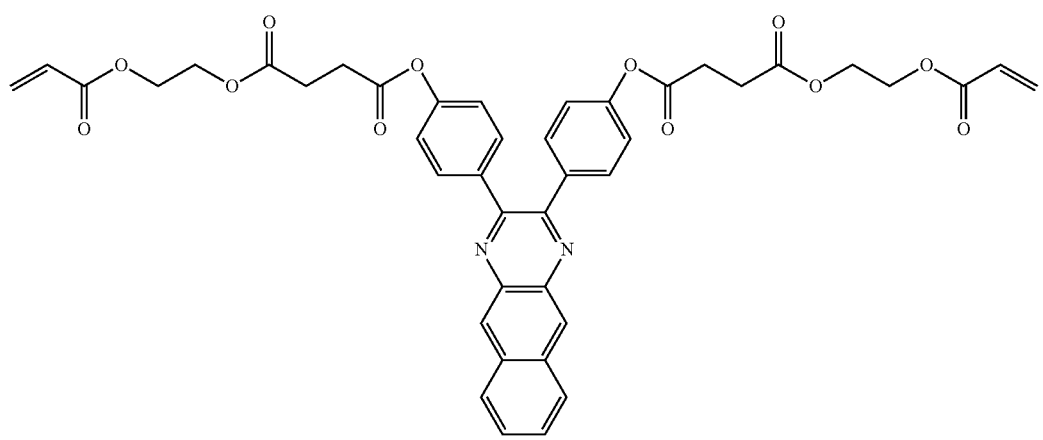
(IV-13)
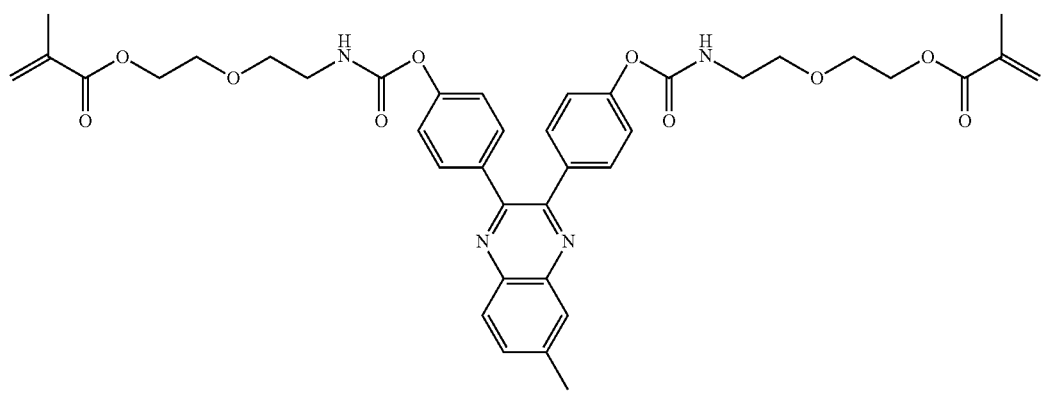
(IV-14)
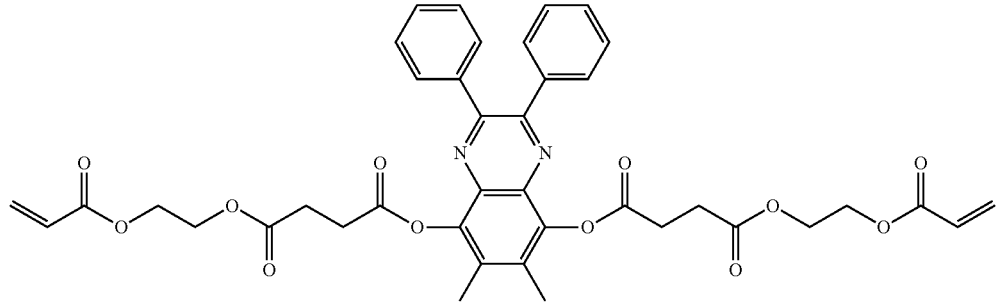
(IV-15)

-continued
(IV-16)
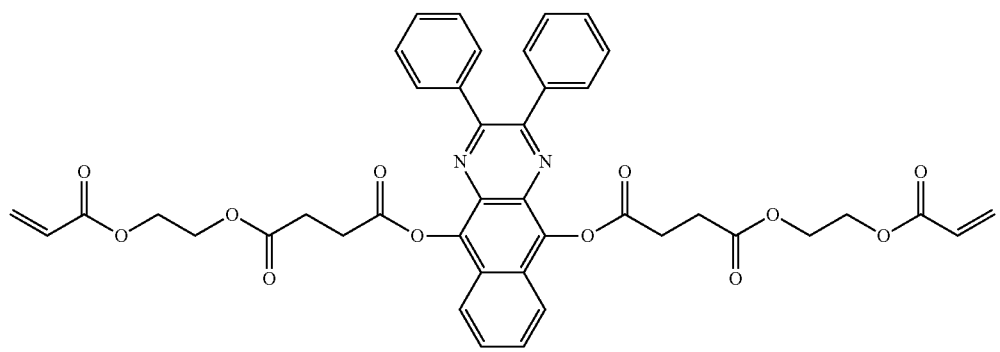
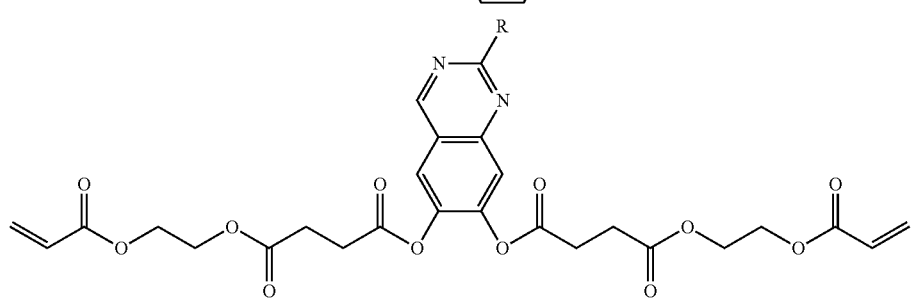
(V-1) 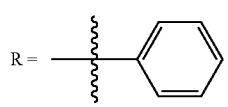 R =
(V-2) 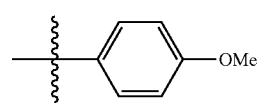
(V-3) 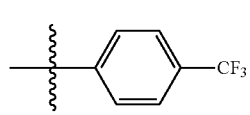
(V-4) 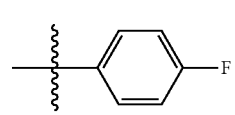
(V-5) 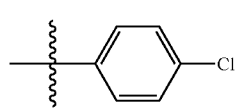
(V-6) 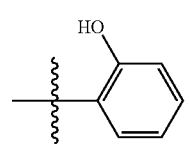
(V-7) 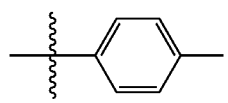
(V-8) 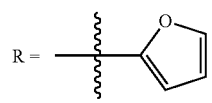 R =
(V-9) 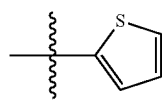
(V-10) 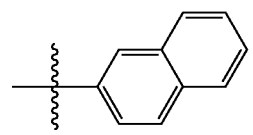
(V-11) 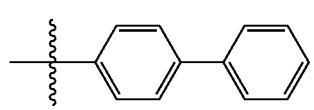
(V-12) 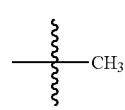
(V-13) 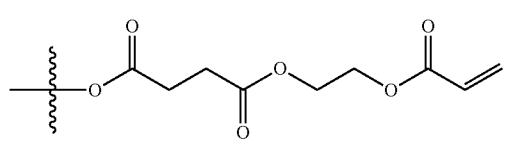

(VI-1)

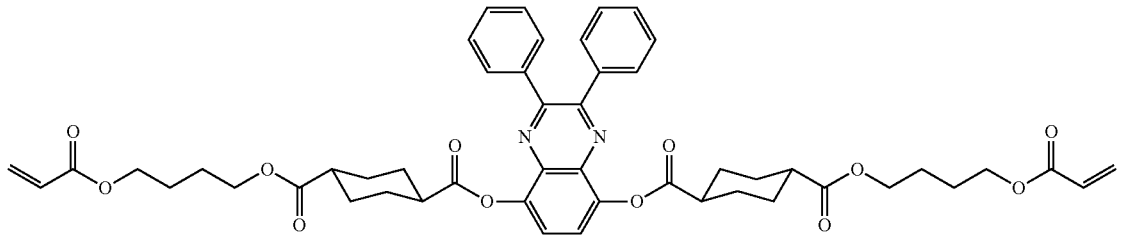

(VI-2)

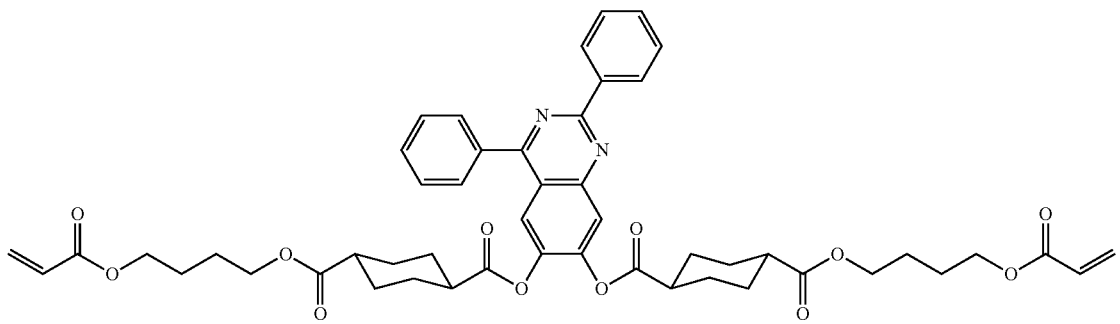

The compound represented by General Formula A has one or two or more asymmetrical carbon atoms in some cases, and stereochemical labels of such asymmetrical carbon atoms each independently may be any of rectus (R) or sinister (S). In addition, the compound represented by General Formula A may be a mixture of stereoisomers such as optical isomers or diastereoisomers. In other words, the compound represented by General Formula A may be any kind of stereoisomer, may be any mixture of stereoisomers, or may be a racemate.

A content of the compound represented by General Formula A in the curable composition is preferably 30% to 95% by mass, is more preferably 35% by mass to 90% by mass, and is even more preferably 40% to 80% by mass with respect to a total mass of the curable composition. In a case where the content of the compound represented by General Formula A is within the above-mentioned range, a partial dispersion ratio (θg, F) higher than a predicted partial dispersion ratio (θg, F) is easily achieved in a cured product having a predetermined Abbe number.

Two or more compounds represented by General Formula A may be contained in the curable composition. In a case where two or more compounds represented by General Formula A are contained, a total content thereof is preferably within the above-mentioned range.

[Compound Represented by General Formula A10]

The present invention provides a novel compound represented by General Formula A10. The compound represented by General Formula A10 is an example of the compound represented by General Formula A.

(A10)

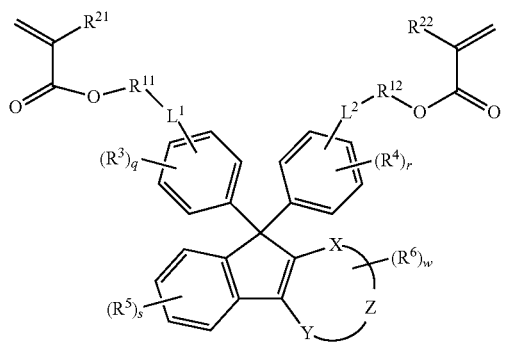

In General Formula A10, X and Y are each independently an oxygen atom, a sulfur atom, a nitrogen atom, or a carbon atom, and at least one of X or Y is an oxygen atom, a sulfur atom, or a nitrogen atom. In X and Y, it is sufficient for a hydrogen atom to be bonded to a carbon atom to which $R^6$ is not bonded to form CH.

It is preferable that X and Y be each independently a nitrogen atom or a carbon atom, it is more preferable that at least one selected from X or Y be a nitrogen atom, and it is even more preferable that both X and Y be nitrogen atoms.

In General Formula A10, Z is an atomic group forming a 5- to 7-membered ring together with X—C=C—Y, and represents an atomic group containing at least one selected from a carbon atom or a heteroatom. Z is preferably an atomic group forming a 5- or 6-membered ring together with X—C=C—Y, and is more preferably an atomic group forming a 6-membered ring. In addition, it is sufficient for Z to be an atomic group containing at least one selected from a carbon atom or a heteroatom, and Z is preferably an atomic group containing a carbon atom, and is more preferably an atomic group consisting of carbon atoms. In Z, it is sufficient for a hydrogen atom to be bonded to a carbon atom to which $R^6$ is not bonded to form CH.

$R^3$ to $R^6$, q, r, and s are respectively synonymous with $R^3$ to $R^6$, q, r, and s in General Formula (A1), and preferable ranges thereof are also the same. w is an integer of 0 or more, and the maximum number of w is the maximum number of substituents that may be substituted on the ring formed by X—C=C—Y and Z.

$L^1$ and $L^2$ represent an ester bond. The ester bond may be any of —O—C(=O)— or —C(=O)—O—, but oxygen is preferably bonded to a phenyl group side to which $L^1$ and $L^2$ are respectively bonded.

Positions at which $L^1$ and $L^2$ are bonded to in a phenyl group are not particularly limited, but both are preferably in a para position with respect to a bonding position of a spiro carbon atom.

$R^{11}$ and $R^{12}$ each independently represent a linear alkylene group having 2 to 20 carbon atoms, or a group in which one or two or more non-adjacent —CH$_2$—'s are substituted by —O—, —C(=O)—, —OC(=O)—, —C(=O)O—, —OC(=)O—, or —NH— in the linear alkylene group having 2 to 20 carbon atoms. $R^{11}$ and $R^{12}$ are each independently preferably a linear alkylene group having 2 to 10 carbon atoms, or a group in which one or two or more non-adjacent —CH$_2$—'s are substituted by —O—, —C(=O)—, —OC(=O)—, —C(=O)O—, or —NH— in the linear alkylene group having 3 to 15 carbon atoms.

In General Formula A10, -$L^1$-$R^{11}$— and -$L^2$-$R^{12}$— are preferably —O—$R_{Alk1}$— or —O—C(=O)—$R_{Alk2}$—C(=O)—O—$R_{Alk3}$—, and are more preferably —O—C(=O)—$R_{Alk2}$—C(=O)—O—$R_{Alk3}$—. $R_{Alk1}$, $R_{Alk2}$, and $R_{Alk3}$ each independently represent a linear alkylene group which has 2 to 10 carbon atoms and does not have a substituent. $R_{Alk1}$, $R_{Alk2}$, and $R_{Alk3}$ are each preferably a linear alkylene group which has 2 to 6 carbon atoms and does not have a substituent, they are each more preferably a linear alkylene group which has 2 to 4 carbon atoms and does not have a substituent, and they are each even more preferably an ethylene group and does not have a substituent.

-$L^1$-$R^{11}$— and -$L^2$-$R^{12}$— may be the same as or different from each other, but they are preferably the same. Both -$L^1$-$R^{11}$— and -$L^2$-$R^{12}$— are particularly preferably —OC(=O)—C$_2$H$_4$—C(=O)—O—C$_2$H$_4$—.

$R^{21}$ and $R^{22}$ each independently represent a hydrogen atom or a methyl group.

The compound represented by General Formula A10 is preferably a compound represented by General Formula A10-1.

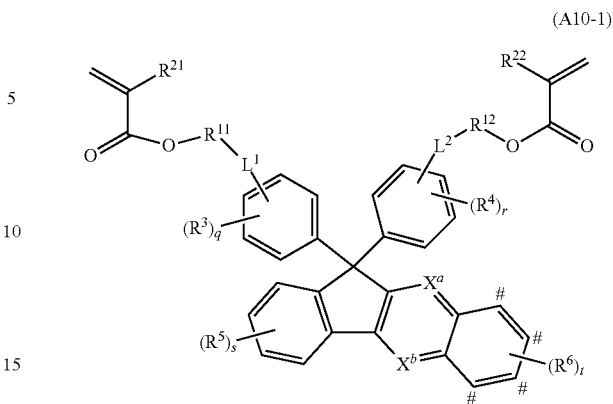

(A10-1)

In General Formula A10-1, $X^a$, $X^b$, t, and # are respectively synonymous with $X^a$, $X^b$, t, and # in General Formula A1.

Both $X^a$ and $X^b$ are preferably N. Furthermore, neither of CH's at positions # is preferably N. It is more preferable that both $X^a$ and $X^b$ be N, and neither of CH's at positions # be N. In this case, it is even more preferable that $R^6$ be a methyl group and t be 1 or 2. In a case where both $X^a$ and $X^b$ are N, a substitution position in a case where t is 1 is preferably a 6-position or 7-position of a formed quinoxaline ring, and substitution positions in a case where t is 2 are preferably a 6-position and a 7-position of a formed quinoxaline ring.

[Compound Represented by General Formula B]

The compound represented by General Formula B is an unsaturated carbonyl compound, and has a diene structure or a double bond directly bonded to an aromatic ring. The inventors of the present invention have found that light stability is high in a cured product formed from a curable composition containing the compound represented by General Formula B together with a polymerizable compound having a nitrogen-containing fused aromatic ring represented by General Formula A as a partial structure. Without being restricted to any particular theory, it is thought that, in the cured product obtained from the curable composition of the embodiment of the present invention, a light reaction (deterioration by light) of the compound represented by General Formula A is inhibited because energy transfer, which is excited by absorbing light, occurs from the compound represented by General Formula A to the compound represented by General Formula B, and thereby the compound represented by General Formula A returns to a ground state. That is, in the curable composition of the embodiment of the present invention, the compound represented by General Formula B is presumed to act as a quencher.

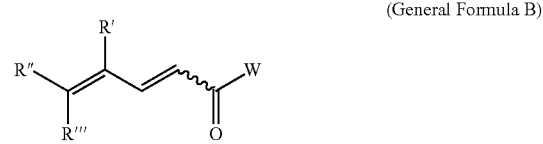

(General Formula B)

In General Formula B, R', R", and R''' each independently represent a hydrogen atom or a substituent; R' and R" or R" and R''' may be bonded to each other to form a ring that may have a substituent; and W is a hydrogen atom or a substituent.

Examples of substituents in a case where R', R", and R'" are each a substituent include an alkyl group which may have a substituent, an alkenyl group which may have a substituent, an aromatic hydrocarbon group which may have a substituent, an aromatic heterocyclic group which may have a substituent, an aliphatic ring group which may have a substituent, an alkoxy group which may have a substituent, an alkenyloxy group which may have a substituent, an aryloxy group which may have a substituent, and the like. The number of carbon atoms of an alkyl group (including an alkyl group in a functional group containing an alkyl group) in the substituents respectively represented by R', R", and R'" is preferably 1 to 6, more preferably 1 to 4, and even more preferably 1 or 2. In the above-mentioned examples of the substituents represented by R', R", and R'", examples of the substituent in the above descriptions of "may have a substituent" include an alkoxy group having 1 to 6 carbon atoms, a halogen atom, a hydroxy group, a cyano group, a nitro group, a nitroso group, a carboxy group, an alkoxycarbonyl group having 1 to 6 carbon atoms, an alkylcarbonyloxy group having 1 to 6 carbon atoms, an alkylcarbonyl group having 1 to 6 carbon atoms, crosslinkable groups, and the like.

In a case where the compound represented by General Formula B contains a crosslinkable group, examples of crosslinkable groups include groups mentioned above as the polymerizable group represented by Pol, a (meth)acryloyloxy group, a (meta)acryloyl amino group, a vinyl group, and the like.

R' and R" or R" and R'" may be bonded to each other to form a ring. It is particularly preferable that R' and R" be bonded to each other to form a ring. Examples of rings formed by bonding of R' and R" to each other include an aromatic hydrocarbon ring, an aromatic heterocyclic ring, an unsaturated hydrocarbon ring, where a benzene ring is preferable. The ring formed by bonding of R' and R" or R" and R'" to each other may have a substituent. Examples of substituents on this ring include an alkyl group which may have a substituent, an alkenyl group which may have a substituent, an aromatic hydrocarbon group which may have a substituent, an aromatic heterocyclic group which may have a substituent, an aliphatic ring group which may have a substituent, an alkoxy group which may have a substituent, an alkenyloxy group which may have a substituent, an aryloxy group which may have a substituent, a hydroxy group, a halogen atom (a fluorine atom, a chlorine atom, a bromine atom, and the like), a crosslinkable group, and the like. The number of carbon atoms of an alkyl group (including an alkyl group in a functional group containing an alkyl group) in a substituent is preferably 1 to 6, more preferably 1 to 4, and even more preferably 1 or 2. In the examples of substituents that may be included in a ring formed by bonding of R' and R" or R" and R'" to each other, examples of substituents that may be included in the ring include an alkoxy group having 1 to 6 carbon atoms, a halogen atom, a hydroxy group, a crosslinkable group, and the like.

In a case where W is a substituent, examples of substituents include an alkyl group which may have a substituent, an alkoxy group which may have a substituent, an alkenyloxy group which may have a substituent, a hydroxy group, a crosslinkable group, and the like. The number of carbon atoms of an alkyl group (including an alkyl group in a functional group containing an alkyl group) in a substituent represented by W is preferably 1 to 6, more preferably 1 to 4, and even more preferably 1 or 2. Examples of substituents in an alkyl group which may have a substituent, an alkoxy group which may have a substituent, and an alkenyloxy group which may have a substituent include an alkoxy group having 1 to 6 carbon atoms, a halogen atom, a hydroxy group, a crosslinkable group, and the like.

The compound represented by General Formula B may have a cis structure or a trans structure, but a trans structure is preferable. That is, the compound represented by General Formula B is preferably a compound represented by General Formula (B1).

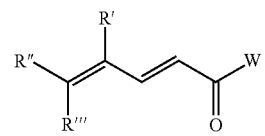

General Formula (B1)

The compound represented by General Formula B is more preferably a compound represented by General Formula (B2).

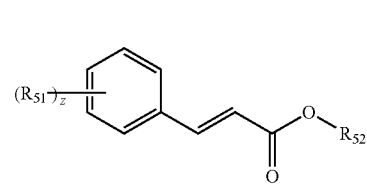

General Formula (B2)

In General Formula (B2), $R_{51}$ represents a substituent, $R_{52}$ represents a hydrogen atom or a substituent, and z represents an integer of 0 to 5.

Examples of $R_{51}$ include an alkyl group, an alkenyl group, an aromatic hydrocarbon group, an aromatic heterocyclic group, an aliphatic ring group, an alkoxy group, an alkenyloxy group, an aryloxy group, a hydroxy group, and the like. Furthermore, these groups may further be substituted by a crosslinkable group. In a case where z is 2 or more, a plurality of $R_{51}$'s may be the same as or different from each other.

In a case where $R_{52}$ is a substituent, examples of substituents include an alkyl group, an alkenyl group, an aromatic hydrocarbon group, an aromatic heterocyclic group, an aliphatic ring group, and the like. These groups may further be substituted by a crosslinkable group.

z represents an integer of 0 to 5, preferably represents an integer of 0 to 2, and more preferably represents an integer of 0 or 1.

The compound represented by General Formula B may be a polymer obtained by polymerization via a crosslinkable group contained in R', R", and R'". The polymer in this case may be a polymer formed from a single monomer or may be a copolymer formed from a plurality of monomers.

Specific examples of the compound represented by General Formula B which is preferably used in the curable composition of the embodiment of the present invention are listed below, but examples are not limited to the following compounds.

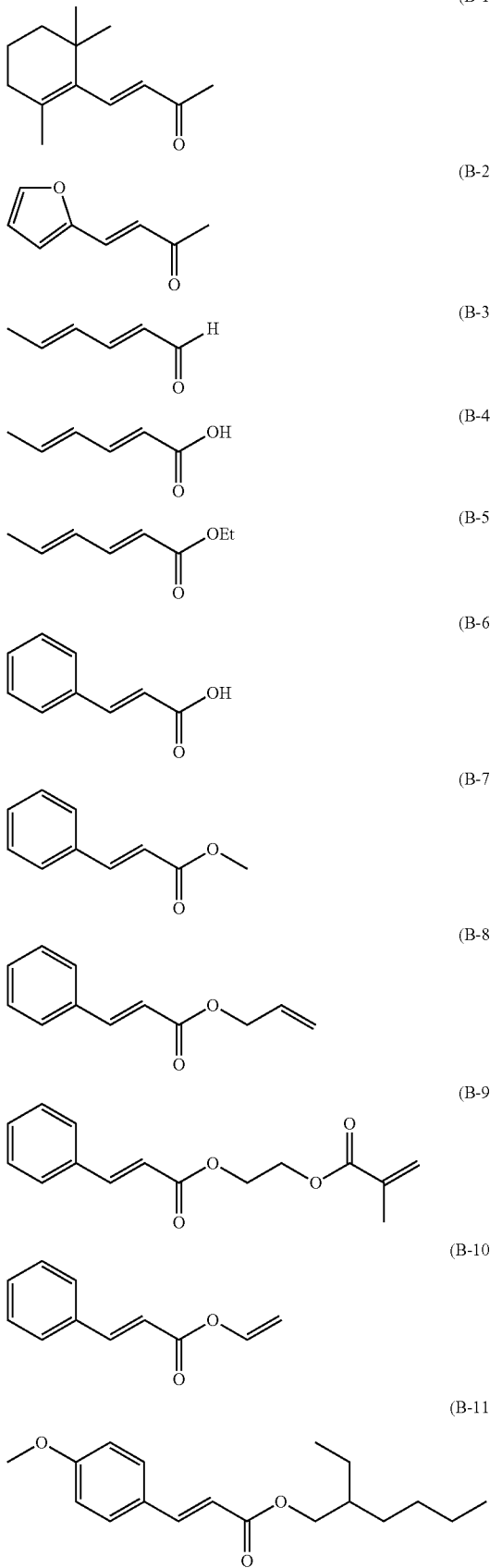

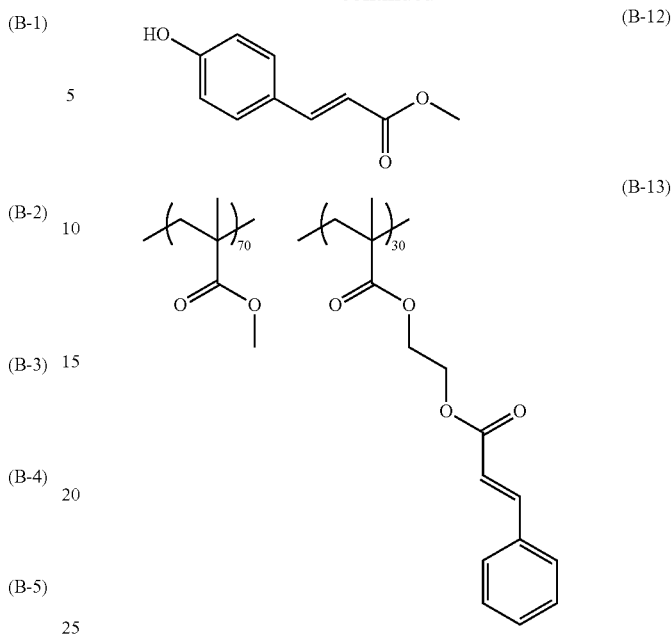

A content of the compound represented by General Formula B in the curable composition is preferably 1% to 30% by mass, is more preferably 2% to 25% by mass, is even more preferably 3% to 20% by mass, and is particularly preferably 3% to 10% by mass with respect to a total mass of the curable composition. In a case where the content of the compound represented by General Formula B is set to 1% by mass or more, it is possible to ensure sufficient light stability of a cured product, and in a case where the content thereof is set to 30% by mass or less, it is possible to maintain a small Abbe number and a large partial dispersion ratio in a cured product.

In addition, a content of the compound represented by General Formula B in the curable composition is preferably 1% to 40% by mass, is more preferably 2% to 30% by mass, and is even more preferably 3% to 25% by mass with respect to a content of the compound represented by General Formula A.

<(Meth)acrylate Monomer>

The curable composition may contain a (meth)acrylate monomer. The (meth)acrylate monomer may be a polyfunctional (meth)acrylate monomer having two or more (meth)acryloyl groups in a molecule, or may be a monofunctional (meth)acrylate monomer having one (meth)acryloyl group in a molecule.

Examples of (meth)acrylate monomers used in the present invention include a monomer 1 (phenoxyethyl acrylate), a monomer 2 (benzyl methacrylate), a monomer 3 (tricyclodecanedimethanol diacrylate), a monomer 4 (dicyclopentanyl acrylate), a monomer 5 (1,6-hexanediol diacrylate), a monomer 6 (1,6-hexanediol dimethacrylate), a monomer 7 (benzyl acrylate), a monomer 8 (isobornyl methacrylate), a monomer 9 (dicyclopentanyl methacrylate), a monomer 10 (dodecyl methacrylate), and the like, which are described below. Furthermore, in addition to the above examples, specific examples of (meth)acrylate monomers include a (meth)acrylate monomer described in paragraphs 0037 to 0046 of JP2012-107191A.

A molecular weight of the (meth)acrylate monomer is preferably 100 to 500.

Monomer 1

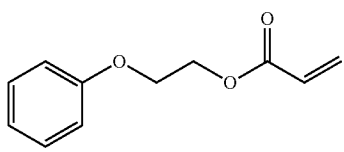

Monomer 2

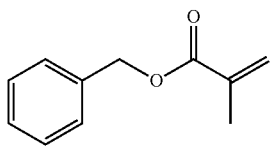

Monomer 3

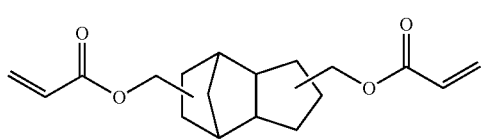

Monomer 4

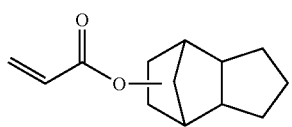

Monomer 5

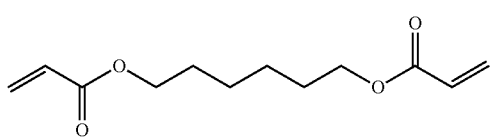

Monomer 6

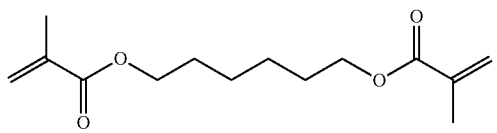

Monomer 7

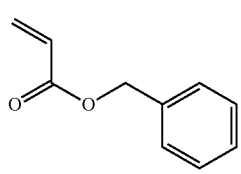

Monomer 8

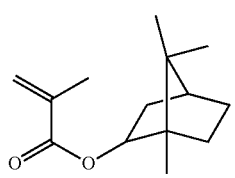

Monomer 9

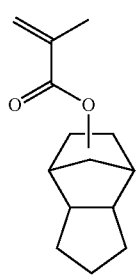

-continued

Monomer 10

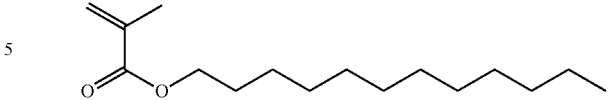

A method of obtaining a (meth)acrylate monomer is not particularly limited, and a commercially available monomer may be used, or it may be manufactured by synthesis. In a case of obtaining a commercially available monomer, for example, it is possible to preferably use VISCOAT #192 PEA (monomer 1) (manufactured by OSAKA ORGANIC CHEMICAL INDUSTRY LTD.), LIGHT ESTER Bz (monomer 2)(manufactured by KYOEISHA CHEMICAL Co., LTD.), A-DCP (monomer 3) (manufactured by Shin-Nakamura Chemical Co., Ltd.), FA-513AS (monomer 4) (manufactured by Hitachi Chemical Co., Ltd.), A-HD-N (monomer 5) (manufactured by Shin-Nakamura Chemical Co., Ltd.), HD-N (monomer 6) (manufactured by Shin-Nakamura Chemical Co., Ltd.), FA-BZA (monomer 7) (manufactured by Hitachi Chemical Co., Ltd.), LIGHT ESTER IB-X (monomer 8) (manufactured by KYOEISHA CHEMICAL Co., LTD.), FA-513M (monomer 9) (manufactured by Hitachi Chemical Co., Ltd.), and LIGHT ESTER L (monomer 10) (manufactured by Kyoeisha Chemical Co., Ltd.).

In a case where the curable composition contains a (meth)acrylate monomer, a content of the (meth)acrylate monomer is preferably 1% to 80% by mass, more preferably 2% to 50% by mass, and even more preferably 3% to 40% by mass, with respect to a total mass of the curable composition. By adjusting an amount of the (meth)acrylate monomer in the curable composition, it is possible to adjust a function of a cured product to relieve stress in a case of heat change.

<Polymer Having Radically Polymerizable Group in Side Chain>

The curable composition of the embodiment of the present invention may further contain a polymer having a radically polymerizable group in a side chain, in addition to the above-described compound. Because the polymer having a radically polymerizable group in a side chain functions to increase a viscosity of the curable composition, it can also be called a thickener or a thickening polymer. The polymer having a radically polymerizable group in a side chain can be added for adjusting a viscosity of the curable composition.

The polymer having a radically polymerizable group in a side chain may be a homopolymer or may be a copolymer. Among them, the polymer having a radically polymerizable group in a side chain is preferably a copolymer. In a case where the polymer having a radically polymerizable group in a side chain is a copolymer, it is sufficient for a copolymer component on at least one side to have a radically polymerizable group. In addition, in a case where the polymer having a radically polymerizable group in a side chain is a copolymer, the polymer is more preferably a copolymer containing a monomer unit having a radically polymerizable group in the side chain and a monomer unit having an aromatic hydrocarbon group in the side chain.

Examples of radically polymerizable groups include a (meth)acrylate group, a vinyl group, a styryl group, an allyl group, and the like. The polymer having a radically polymerizable group in a side chain preferably contains 5% to 100% by mass, more preferably contains 10% to 90% by mass, and even more preferably contains 20% to 80% by mass of repeating units having a radically polymerizable group.

Specific examples of the polymer having a radically polymerizable group in a side chain which is preferably used in the present invention are listed below, but the polymer having a radically polymerizable group in a side chain is not limited to the following structures. Each of the specific examples shown below is a copolymer, and each copolymer includes adjacent structural units which are illustrated secondly or thirdly therefrom. For example, a specific example described at the top is an allyl methacrylate-benzyl methacrylate copolymer.

In the structural formulas below, Ra and Rb each independently represent hydrogen or a methyl group. A plurality of Ra's in one polymer may be the same as or different from each other. In addition, n represents an integer of 0 to 10, preferably represents 0 to 2, and more preferably represents 0 or 1.

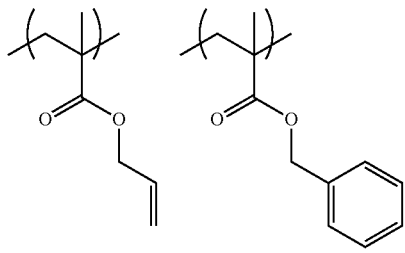
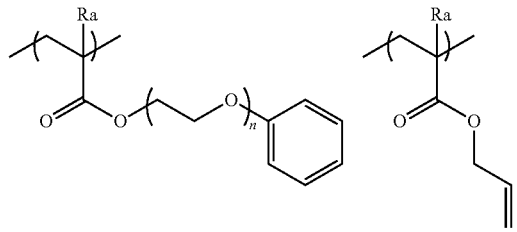
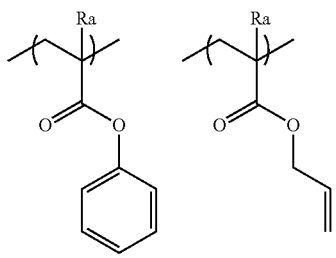
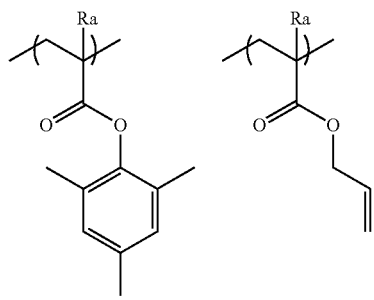
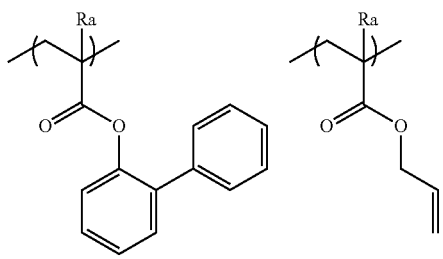
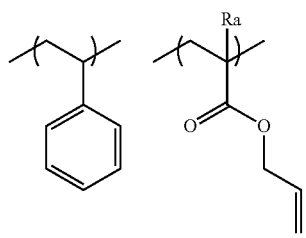
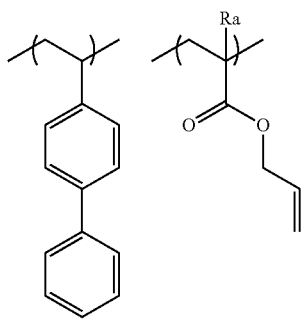
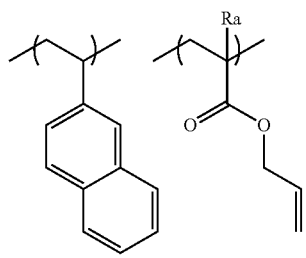
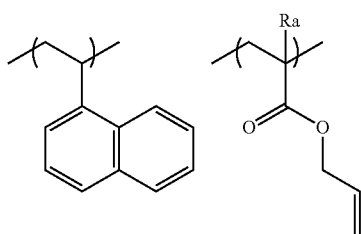
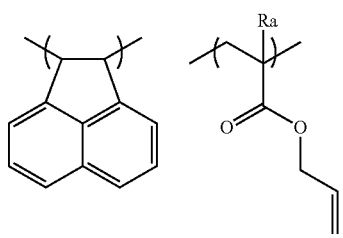

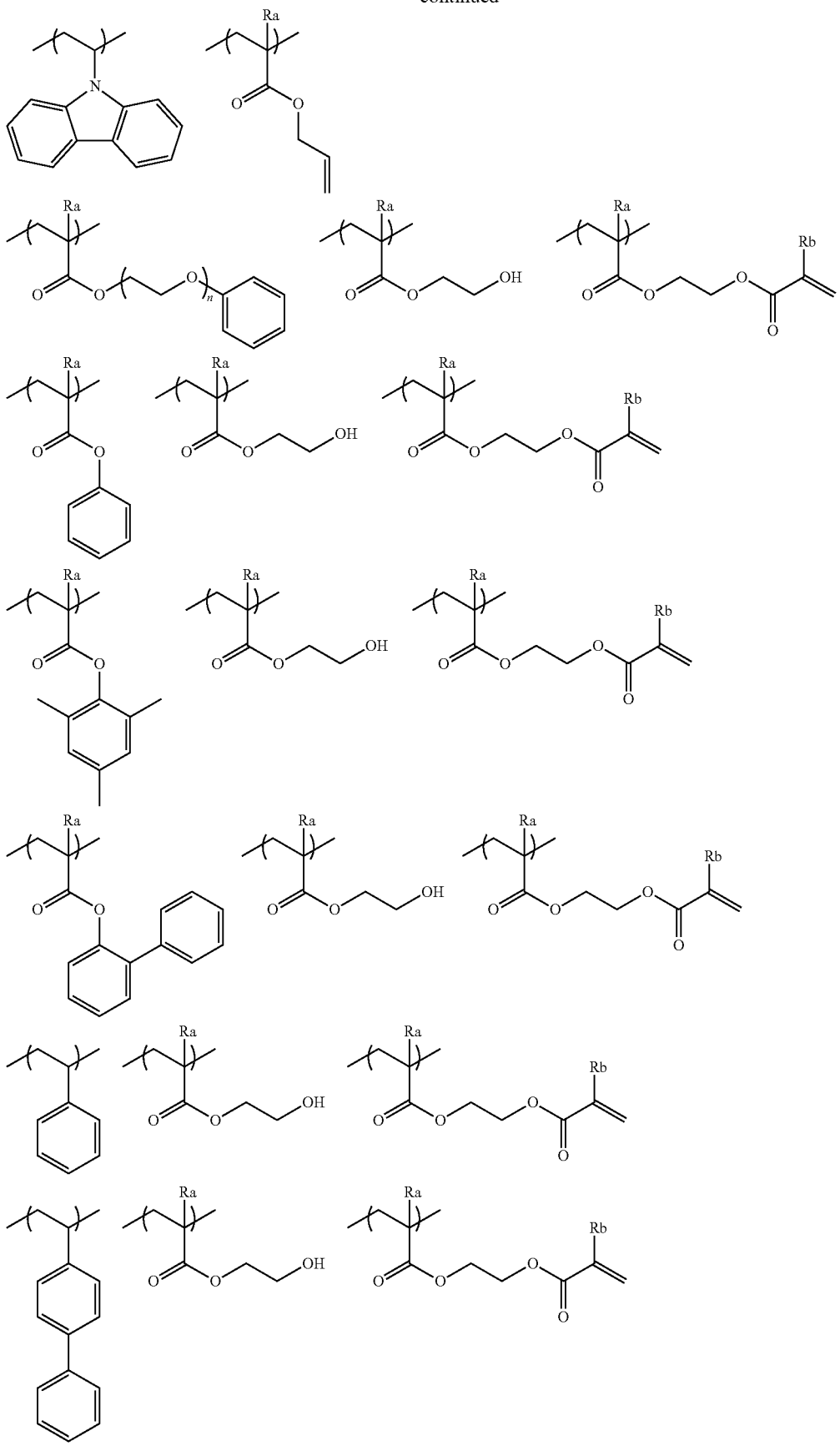

-continued
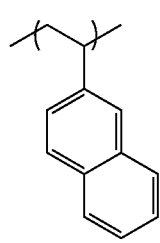 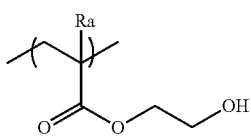 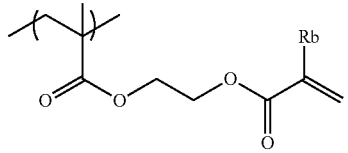
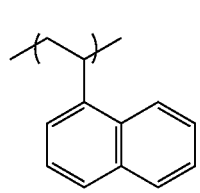 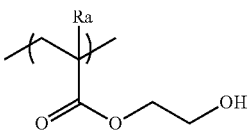 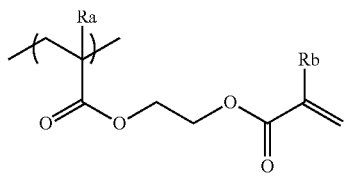
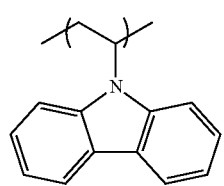 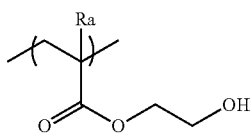 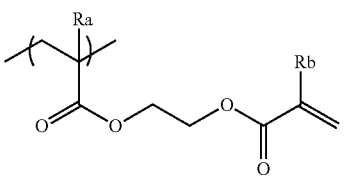
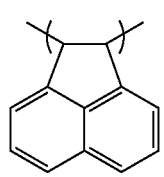 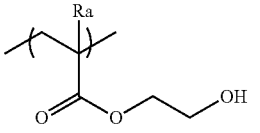 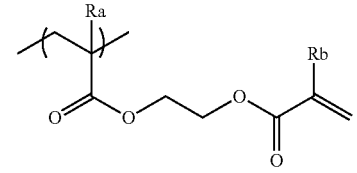
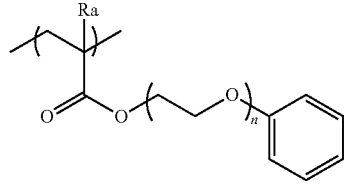 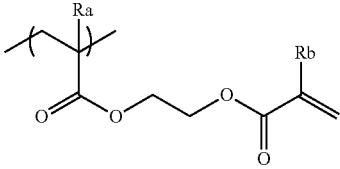
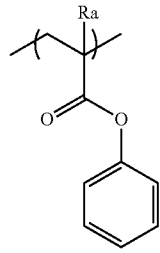 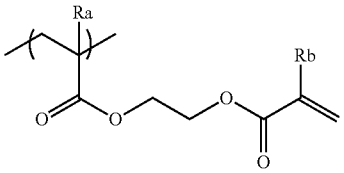 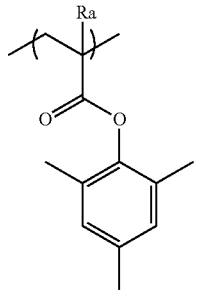 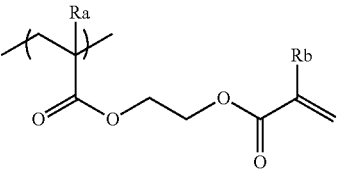
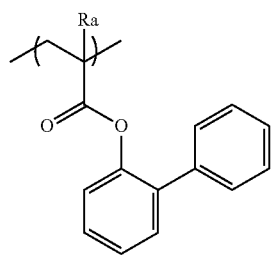 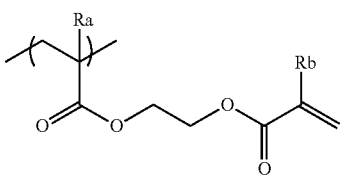

-continued

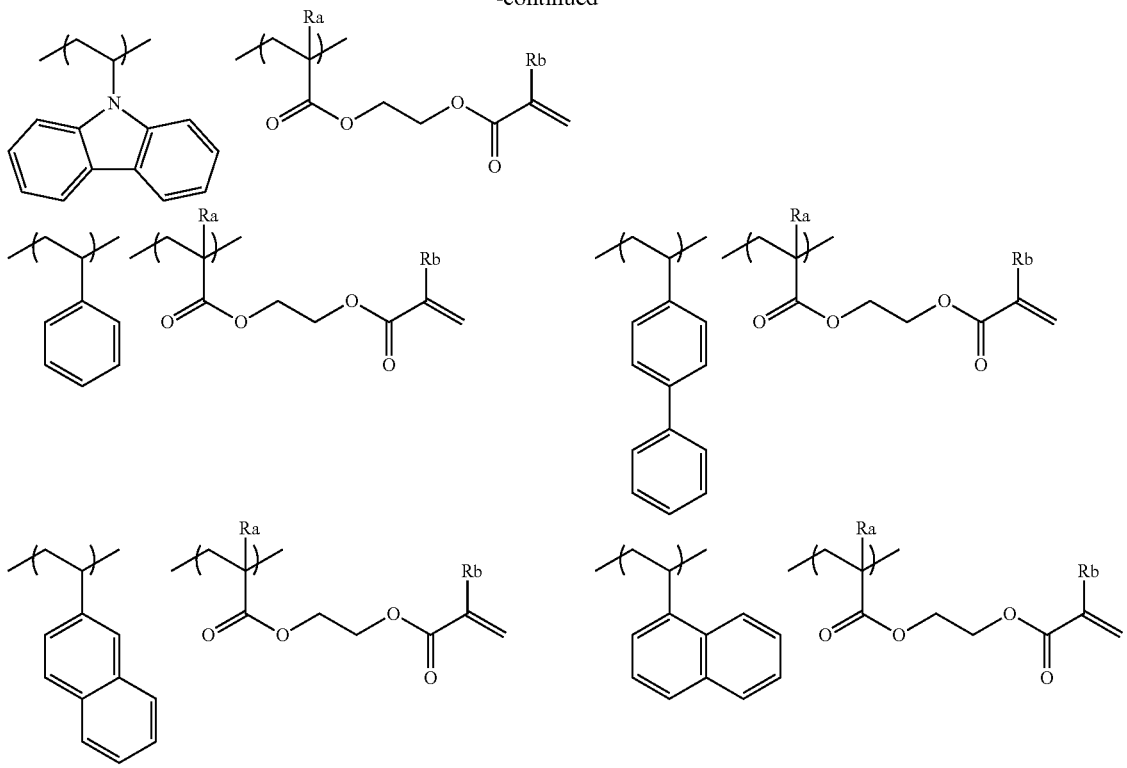

A molecular weight (weight-average molecular weight) of the polymer having a radically polymerizable group in a side chain is preferably 1,000 to 10,000,000, more preferably 5,000 to 300,000, and even more preferably 10,000 to 200,000. In addition, a glass transition temperature of the polymer having a radically polymerizable group in a side chain is preferably 50° C. to 400° C., more preferably 70° C. to 350° C., and even more preferably 100° C. to 300° C.

A content of the polymer having a radically polymerizable group in a side chain is preferably 40% by mass or less, more preferably 30% by mass or less, and even more preferably 25% by mass or less with respect to a total mass of the curable composition. A content of the polymer having a radically polymerizable group in a side chain may be 0% by mass, and an aspect in which the polymer having a radically polymerizable group in a side chain is not added is also preferable.

[Polymerization Initiator]

The curable composition of the embodiment of the present invention preferably contains at least one selected from a photoradical polymerization initiator or a thermal radical polymerization initiator.

(Thermal Radical Polymerization Initiator)

The curable composition preferably contains a thermal radical polymerization initiator. By thermally polymerizing the curable composition according to this action, it is possible to mold a cured product having high heat resistance.

Specifically, the following compounds can be used as the thermal radical polymerization initiator. Examples of thermal radical polymerization initiators include 1,1-di(t-hexylperoxy)cyclohexane, 1,1-di(t-butylperoxy)cyclohexane, 2,2-di(4,4-di-(t-butylperoxy)cyclohexyl)propane, t-hexylperoxyisopropyl monocarbonate, t-butylperoxy-3,5,5-trimethylhexanoate, t-butylperoxy laurate, dicumyl peroxide, di-t-butyl peroxide, t-butylperoxy-2-ethylhexanoate, t-hexylperoxy-2-ethylhexanoate, cumene hydroperoxide, t-butyl hydroperoxide, t-butylperoxy-2-ethylhexyl, 2,3-dimethyl-2,3-diphenylbutane, and the like.

A content of the thermal radical polymerization initiator is preferably 0.01% to 10% by mass, more preferably 0.05% to 5% by mass, and even more preferably 0.05% to 2% by mass, with respect to a total mass of the curable composition.

(Photoradical Polymerization Initiator)

The curable composition preferably contains a photoradical polymerization initiator. Specifically, the following compounds can be used as the photoradical polymerization initiator. Examples of photoradical polymerization initiators include bis(2,6-dimethoxybenzoyl)-2,4,4-trimethylpentylphosphine oxide, bis(2,6-dimethylbenzoyl)-2,4,4-trimethylpentylphosphine oxide, bis(2,4,6-trimethylbenzoyl)-2,4,4-trimethylpentylphosphine oxide, bis(2,6-dichlorobenzoyl)-2,4,4-trimethylpentylphosphine oxide, 1-phenyl-2-hydroxy-2-methylpropan-1-one, 1-hydroxycyclohexyl phenyl ketone, 1-(4-isopropylphenyl)-2-hydroxy-2-methylpropan-1-one, 1,2-diphenylethanedione, methylphenyl glyoxylate, 1-[4-(2-hydroxyethoxy)-phenyl]-2-hydroxy-2-methyl-1-propan-1-one, 2-hydroxy-1-{4-[4-(2-hydroxy-2-methyl-propionyl)-benzyl]phenyl}-2-methyl-propan-1-one, 2,2-dimethoxy-1,2-diphenylethan-1-one, 2-methyl-1-(4-methylthiophenyl)-2-morpholinopropan-1-one, 2-benzyl-2-dimethylamino-1-(4-morpholinophenyl)-butanone-1,2,4,6-trimethylbenzoyl-diphenyl-phosphine oxide, bis(2,4,6-trimethylbenzoyl)-phenylphosphine oxide, and the like.

Among them, as a photoradical polymerization initiator in the present invention, it is possible to preferably use IRGACURE 184 (1-hydroxycyclohexyl phenyl ketone), IRGA- CURE 819 (bis(2,4,6-trimethylbenzoyl)-phenylphosphine oxide), and IRGACURE 651 (2,2-dimethoxy-1,2-diphenylethan-1-one), which are manufactured by BASF SE, 1-[4-(2-hydroxyethoxy)-phenyl]-2-hydroxy-2-methyl-1-propan-1-one, or 2-methyl-1-(4-methylthiophenyl)-2-morpholinopropan-1-one.

A content of the photoradical polymerization initiator is preferably 0.01% to 5.0% by mass, more preferably 0.05% to 1.0% by mass, and even more preferably 0.05% to 0.5% by mass, with respect to a total mass of the curable composition.

The curable composition preferably contains both photoradical polymerization initiator and thermal radical polymerization initiator, and in this case, a total content of the photoradical polymerization initiator and the thermal radical polymerization initiator is preferably 0.01% to 5% by mass, more preferably 0.05% to 1.0% by mass, and even more preferably 0.05% to 0.5% by mass, with respect to a total mass of the curable composition.

[Other Additives and the Like]

Unless contrary to the gist of the present invention, the curable composition of the embodiment of the present invention may contain polymers and monomers which are other than the components described above, and additives such as dispersants, plasticizers, thermal stabilizers, and mold release agents.

A viscosity of the curable composition of the embodiment of the present invention is preferably 20,000 mPa·s or less, is more preferably 15,000 mPa·s or less, is even more preferably 13,000 mPa·s or less, and is particularly preferably 10,000 mPa·s or less. In a case where the viscosity of the curable composition is within the above-mentioned range, it is possible to improve handleability in a case of molding a cured product, and thereby it is possible to mold a high-quality cured product. A viscosity of the curable composition is preferably 2,000 mPa·s or more, is more preferably 3,000 mPa·s or more, is even more preferably 4,000 mPa·s or more, and is particularly preferably 5,000 mPa·s or more.

<Cured Product>

By curing the curable composition of the embodiment of the present invention, it is possible to obtain a cured product having a small Abbe number and a large partial dispersion ratio.

An Abbe number (vd) and a partial dispersion ratio (θg, F) of the cured product are values measured using a Kalnew precision refractometer KPR-2000 (manufactured by Shimadzu Device Corporation). Specifically, the curable composition is poured into a transparent glass mold having a diameter of 20 mm and a thickness of 2 mm, and heated at 200° C. in an atmosphere having an oxygen concentration of 1% or less to mold a cured product (a heating step), and an Abbe number (vd) and a partial dispersion ratio (θg, F) of this cured product are measured. An Abbe number (vd) and a partial dispersion ratio (θg, F) of the cured product are calculated by the following expression. In a case of molding a cured product, an ultraviolet irradiation step may be employed instead of the above-described heating step, or both of the heating step and the ultraviolet irradiation step may be employed.

$$vd=(nd-1)/(nF-nC)$$

$$\theta g, F=(ng-nF)/(nF-nC)$$

Provided that nd represents a refractive index at a wavelength of 587.56 nm, nF represents a refractive index at a wavelength of 486.13 nm, nC represents a refractive index at a wavelength of 656.27 nm, and ng represents a refractive index at a wavelength of 435.83 nm.

An Abbe number of the cured product of the embodiment of the present invention is not particularly limited, but it is preferably 35 or less, more preferably 30 or less, even more preferably 29 or less, and particularly preferably 28 or less. In addition, an Abbe number of the cured product of the embodiment of the present invention is not particularly limited, but it is preferably 1 or more, is more preferably 3 or more, is even more preferably 5 or more, and is particularly preferably 7 or more.

A partial dispersion ratio (θg, F) of the cured product of the embodiment of the present invention is not particularly limited, but it is preferably 0.65 or more, is more preferably 0.70 or more, and is even more preferably 0.75 or more. In addition, a partial dispersion ratio (θg, F) of the cured product of the embodiment of the present invention is not particularly limited, but it is preferably 2 or less, is more preferably 1.8 or less, and is even more preferably 1.7 or less.

[Method for Manufacturing Cured Product]

The cured product can be manufactured by a method including a step of photocuring the curable composition of the embodiment of the present invention, and/or a step of thermally curing the same. A method for manufacturing a cured product preferably includes a step of forming a semi-cured product by irradiating the curable composition with light or heating the curable composition; and a step of forming a cured product by irradiating the obtained semi-cured product with light or heating the obtained semi-cured product.

[Step of Forming Semi-Cured Product]

The step of forming a semi-cured product preferably includes a transfer step. The transfer step is a step of pressing a metallic mold against the curable composition mentioned above. In the transfer step, the other metallic mold is pressed against the curable composition injected into the one of the pair of metallic molds to spread the curable composition.

The metallic mold used in the method for manufacturing a cured product is preferably a metallic mold that has been subjected to a chromium nitride treatment. Thereby, a favorable mold releasability can be obtained in a release step to be performed in subsequent steps, and manufacture efficiency of an optical member can be increased.

Examples of chromium nitride treatments include a method of forming a chromium nitride film on a metallic mold surface. Examples of methods of forming a chromium nitride film on a metallic mold surface include a Chemical Vapor Deposition (CVD) method and a Physical Vapor Deposition (PVD) method. The CVD method is a method of forming a chromium nitride film on a substrate surface by reacting a source gas containing chromium and a source gas containing nitrogen at a high temperature. In addition, the PVD method is a method of forming a chromium nitride film on a substrate surface by utilizing an arc discharge (arc type vacuum deposition method). In this arc type vacuum deposition method, a cathode (evaporation source) made of chromium, for example, is placed in the vacuum vessel, an arc discharge is caused between the cathode and the wall of the vacuum vessel via a trigger, ionization of the metal by arc plasma is performed at the same time as vaporizing the cathode, a negative voltage is applied to the substrate, and about several tens of mTorr (1.33 Pa) of a reaction gas (for example, a nitrogen gas) is put into the vacuum vessel, and thereby the ionized metal and the reaction gas are reacted on the surface of the substrate to form a compound film. In the present invention, the chromium nitride treatment on a metallic mold surface is performed by the CVD method or the PVD method.

In general, a metallic mold can be heated while applying pressure to contents by combining two metallic molds, and in a case where a low-viscosity composition is injected into the metallic mold, leakage into the mold clearance is caused. For this reason, a curable composition to be injected into a metallic mold preferably has a viscosity of a certain level or higher level. In order to adjust a viscosity of a curable composition, the above-described polymer having a radically polymerizable group in a side chain may be added to the curable composition.

After the step of pressing the metallic mold, a step of forming a semi-cured product is provided. The semi-cured product can be obtained by semi-curing the curable composition injected into the metallic mold. In the step of forming a semi-cured product, light irradiation or heating is performed. In the present specification, such a step can also be called a semi-curing step.

In the semi-curing step, the curable composition of the embodiment of the present invention is subjected to at least one of light irradiation or heating. In the semi-curing, there is generally no difference in Abbe number and partial dispersion ratio (θg, F) of a finally obtained cured product, regardless of whether light irradiation is performed or heating is performed. In the semi-curing step, it is preferable to form a semi-cured product in which a complex viscosity at 25° C. and a frequency of 10 Hz is $10^5$ to $10^8$ mPa·s.

The term "semi-cured product" in the present specification refers to a product obtained by polymerizing a curable composition, and it is in a state of not being completely solid but having fluidity to some extent. In a case where a complex viscosity of a polymer of a curable composition is $10^5$ to $10^8$ mPa·s at 25° C. and a frequency of 10 Hz, this polymer is a semi-cured product. That is, polymers in which an upper limit value of a complex viscosity at 25° C. and a frequency of 10 Hz is less than $1.0 \times 10^9$ mPa·s are considered to fall within a range of semi-cured products. On the other hand, the term "cured product" refers to a product obtained by curing a curable composition by polymerization, and it is in a state of being completely solid.

Light used in the light irradiation is preferably ultraviolet rays or visible light, and is more preferably ultraviolet rays. For example, a metal halide lamp, a low pressure mercury lamp, a high pressure mercury lamp, an ultrahigh pressure mercury lamp, a germicidal lamp, a xenon lamp, a light emitting diode (LED) light source lamp, and the like are suitably used. An atmosphere during light irradiation is preferably air or an inert-gas-purged atmosphere, and is more preferably an atmosphere in which air is purged with nitrogen until an oxygen concentration reached 1% or less.

In a case of providing a heating and semi-curing step in the semi-curing step, heating and semi-curing are preferably carried out such that a complex viscosity of a semi-cured product after heating is $10^5$ to $10^8$ mPa·s at 25° C. and a frequency of 10 Hz.

The present invention may relate to a semi-cured product manufactured by the above-described method. Such a semi-cured product can be preferably used for a method for manufacturing a cured product to be described later. A preferred range of the complex viscosity of the semi-cured product is the same as the preferred range of the complex viscosity of the semi-cured product in the above-described step of forming a semi-cured product.

After the light irradiation step, a photoradical polymerization initiator may not be contained in the semi-cured product at all because it has been completely consumed, or a photoradical polymerization initiator may remain in the semi-cured product.

In addition, a glass transition temperature of the semi-cured product is preferably −150° C. to 0° C., more preferably −50° C. to 0° C., and particularly preferably −20° C. to 0° C.

[Step of Forming Cured Product]

The step of forming a cured product preferably includes a polymerization step of obtaining a cured product by thermal polymerization in which the semi-cured product is put into a molding mold for deformation under pressure and heating is performed, or by photopolymerization in which the semi-cured product is irradiated with light. In the present specification, such a step can also be called a curing step. Light irradiation conditions and heating conditions in the step of forming a cured product are the same as the conditions in the semi-curing step described above.

In a case where the curing step is the thermal polymerization step, a molding mold used in the polymerization step is also referred to as a thermoforming mold. In general, the thermoforming mold preferably has a configuration in which two molding molds can be heated while applying pressure to contents by combining the two molding molds. In addition, in the method for manufacturing a cured product, it is more preferable to use a metallic mold as the molding mold in the thermal polymerization step of obtaining a cured product. As such a thermoforming mold, it is possible to use a mold described in, for example, JP2009-126011A. In addition, the metallic mold is preferably a mold that has been subjected to a chromium nitride treatment.

In the thermal polymerization step, the semi-cured product put into a molding mold is deformed under pressure, and heated for thermal polymerization, and thereby a cured product is obtained. Deformation under pressure and heating may be performed at the same time, heating may be performed after deformation under pressure, or deformation under pressure may be performed after heating. Among them, it is preferable to perform deformation under pressure and heating at the same time. In addition, it is also preferable to further perform heating at a high temperature after a pressure applied has become stable, after deformation under pressure and heating are performed at the same time.

In the thermal polymerization step, the semi-cured product is heated at a temperature of 150° C. or higher and cured, and thereby a cured product is obtained.

A heating temperature is 150° C. or higher, is preferably 160° C. to 270° C., is more preferably 165° C. to 250° C., and is even more preferably 170° C. to 230° C.

In this curing step, it is preferable to perform deformation under pressure together with heating. Thereby, an inverted shape of an inner surface of the metallic mold can be accurately transferred to the cured product.

A pressure for the deformation under pressure is preferably 0.098 MPa to 9.8 MPa, more preferably 0.294 MPa to 4.9 MPa, and particularly preferably 0.294 MPa to 2.94 MPa.

A time of the thermal polymerization is preferably 30 to 1,000 seconds, more preferably 30 to 500 seconds, and particularly preferably 60 to 300 seconds. An atmosphere in the thermal polymerization is preferably air or an inert-gas-purged atmosphere, and is more preferably an atmosphere in which air is purged with nitrogen until an oxygen concentration reached 1% or less.

A release step is provided after the curing step. In a case where the thermal polymerization is performed in the curing step, the metallic mold is preferably separated from the cured product within a temperature range of 150° C. to 250° C. in the release step. By setting the temperature in the release step within the above-mentioned range, the metallic mold can be easily separated from the cured product, and manufacture efficiency can be increased.

Hereinbefore, although the example of the method for manufacturing a cured product of the embodiment of the present invention was described, the configuration of the present invention is not restricted thereto, and it can be suitably changed within the range which does not deviate from the present invention. For example, a metallic mold used in the transfer step and the semi-curing step may be used as it is in the curing step; or the metallic mold may be pulled away from the semi-cured product to be separated after performing the semi-curing step, and the semi-cured product may be moved into another metallic mold (thermoforming mold) to perform the curing step. In this case, the metallic mold used in the semi-curing step and the curing step is preferably subjected to the above-described chromium treatment.

Furthermore, in the semi-curing step, the curable composition in the metallic mold may be irradiated with light and also may be heated. Thereby, a semi-cured product having a desired degree of curing can be obtained reliably.

[Semi-Cured Product]

The semi-cured product can be formed by semi-curing the curable composition. The semi-cured product is preferably a semi-cured product manufactured by a method for manufacturing a semi-cured product. In addition, in the semi-cured product, a complex viscosity at 25° C. and a frequency of 10 Hz is preferably $10^5$ to $10^8$ mPa·s.

The cured product of the embodiment of the present invention may be formed by curing the semi-cured product described above.

<Optical Member>

The cured product of the embodiment of the present invention can be preferably used for an optical member.

The type of optical member is not particularly limited, but the cured product of the embodiment of the present invention can be suitably used especially for light-transmissive optical members (so-called passive optical members). Examples of optically-functional devices including such optical members include various types of display devices (a liquid crystal display, a plasma display, and the like), various types of projector devices (an overhead projector (OHP), a liquid crystal projector, and the like), optical fiber communication devices (an optical waveguide, a light amplifier, and the like), image-capturing devices such as a camera and a video, and the like.

Examples of passive optical members include lenses, prisms, prism sheets, panels (plate-like molded objects), films, optical waveguides (a film-like optical waveguide, a fiber-like optical waveguide, and the like), optical discs, LED sealants, and the like. The passive optical member may have an arbitrary coating layer or an arbitrary additional functional layer, if necessary. For example, the passive optical member may have a protective layer for preventing mechanical damage of a coating surface caused by friction or abrasion; a light-absorbing layer for absorbing a light having an undesirable wavelength which is a cause of degradation of inorganic particles, base materials, and the like; a permeation blocking layer for inhibiting or preventing permeation of reactive small molecules such as moisture or oxygen gas; an antiglare layer; an antireflection layer; a layer of low refractive index; and the like. Specific examples of coating layers include a transparent conductive film or gas barrier film consisting of an inorganic oxide coating layer or inorganic nitride coating layer, a gas barrier film or hard coating film consisting of an organic coating layer, and the like. As a coating method for forming the coating layer, it is possible to use a known coating method such as a vacuum deposition method, a CVD method, a sputtering method, a dip coating method, and a spin coating method.

[Lens Base Material]

The optical member may be a lens base material. That is, a lens base material can be manufactured using the curable composition of the embodiment of the present invention. In the present specification, the "lens base material" refers to a single member capable of exhibiting a lens function. The lens base material manufactured using the curable composition of the embodiment of the present invention exhibits a small Abbe number and a high partial dispersion ratio. Preferably, by suitably adjusting the type of monomer constituting the curable composition, it is possible to control a refractive index of the lens base material in an arbitrary value, and furthermore, it is possible to obtain the lens base material having high refractive properties, light transmittance, and lightweight properties.

A film and a member may be provided on a surface and the periphery of the lens base material depending on use environments and usage applications of lenses. For example, a protective film, an antireflection film, a hard coating film, or the like may be formed on the surface of the lens base material. In addition, a lens base material manufactured using the cured product of the embodiment of the present invention can be made into a compound lens laminated with one or more other lens base materials selected from a glass lens base material and a plastic lens base material.

The periphery of the lens base material may be fitted to be fixed in a base-material-holding frame or the like. However, these films, frames, and the like are members added to the lens base material, and therefore they are distinguished from the lens base material itself referred to in the present specification.

In a case of using the lens base material for lenses, the lens base material alone may be used as a lens as it is, or the above-mentioned films, frames, other lens base materials, and the like may be added and used as a lens. The type and a shape of a lens formed of the lens base material are not particularly limited, but the maximum thickness thereof is preferably 0.1 to 10 mm. The maximum thickness is more preferably 0.1 to 5 mm, and is particularly preferably 0.15 to 3 mm. In addition, the lens base material is preferably a circular shape having the maximum diameter of 1 to 1,000 mm. The maximum diameter is more preferably 2 to 200 mm, and is particularly preferably 2.5 to 100 mm.

The lens base material is preferably used for lenses for imaging devices such as mobile phones or digital cameras; lenses for capturing devices such as TV or video cameras; lenses for in-vehicle devices; and endoscope lenses.

<Cemented Lens>

A cemented lens can be manufactured by allowing a lens base material or lens manufactured using the curable composition of the embodiment of the present invention to adhere to another lens using a lens adhesive.

[Other Lenses]

The type of other lenses is not particularly limited, and examples thereof include a disk-shaped convex lens, a concave lens, a meniscus lens, an aspheric lens, and a cylindrical lens having a cylindrical lens surface, a ball lens, a rod lens, and the like. In addition, a material of the other lenses is not particularly limited as long as the other lens is a glass lens, a resin lens, or a compound lens.

(Glass Lens)

As a glass lens, known glass lenses can be used without limitation. Examples of commercially available glass lenses include BK7 manufactured by Ohara Corporation.

Similar glass lenses can be used also in a case where a compound lens includes a glass lens.

(Resin Lens and Compound Lens)

A resin lens means a lens made of a resin cured product.

In the present specification, a compound lens means a lens having a layer made of glass and a resin layer. The resin layer is a layer made of a resin cured product. Each layer included in the compound lens may be a lens (single lens), and in this case, optical axes of each of the single lens (a line connecting curvature centers of both spherical surfaces) preferably coincide with each other. The compound lens may have a resin layer on a surface or inner side thereof.

[Lens Adhesive]

As a lens adhesive, known lens adhesives can be used without limitation.

As the lens adhesive, it is particularly preferable to use a lens adhesive containing the compound represented by General Formula 1. The lens adhesive containing the compound represented by General Formula 1 absorbs ultraviolet rays, but is still excellent in fastness with respect to ultraviolet irradiation. Accordingly, by using this lens adhesive, it is possible to obtain a cured product having high light stability as a cemented lens. Furthermore, an adhesive layer formed from the lens adhesive containing the compound represented by General Formula 1 has high heat shock resistance.

(Compound Represented by General Formula 1)

$Pol_1-Sp_1-L_1-Ar_{21}-L_2-SP_2-Pol_2$  (General Formula 1)

In the formula, $Ar_{21}$ is any aromatic ring group represented by General Formulas 21-1 to 21-4.

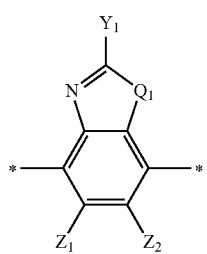

General Formula 21-1

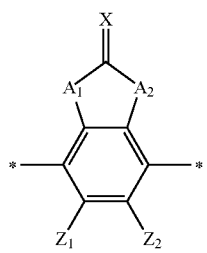

General Formula 21-2

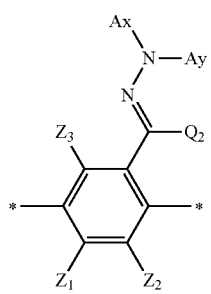

General Formula 21-3

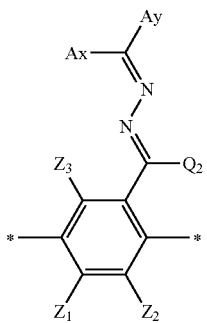

General Formula 21-4

In General Formulas 21-1 to 21-4, $Q_1$ represents —S—, —O—, or $NR_{11}$—, and $R_{11}$ represents a hydrogen atom or an alkyl group having 1 to 6 carbon atoms, $Y_1$ represents an alkyl group which has 1 to 6 carbon atoms and may have a substituent, an aromatic hydrocarbon group which has 6 to 12 carbon atoms and may have a substituent, or an aromatic heterocyclic group which has 3 to 12 carbon atoms and may have a substituent, $Z_1$, $Z_2$, and $Z_3$ each independently represent a hydrogen atom, an aliphatic hydrocarbon group which has 1 to 20 carbon atoms and may have a substituent, an alkoxy group which has 1 to 20 carbon atoms and may have a substituent, an alicyclic hydrocarbon group which has 3 to 20 carbon atoms and may have a substituent, a monovalent aromatic hydrocarbon group which has 6 to 20 carbon atoms and may have a substituent, a halogen atom, a cyano group, a nitro group, —$NR_{12}R_{13}$, or $SR_{12}$; $Z_1$ and $Z_2$ may be bonded to each other to form an aromatic hydrocarbon ring which may have a substituent or an aromatic heterocyclic ring which may have a substituent; and $R_{12}$ and $R_{13}$ each independently represent a hydrogen atom or an alkyl group having 1 to 6 carbon atoms, $A_1$ and $A_2$ each independently represent a group selected from the group consisting of —O—, —$NR_{21}$— (where $R_{21}$ represents a hydrogen atom or a substituent), —S—, and —C(=O)—; and X represents O, S, C to which a hydrogen atom or a substituent is bonded, or N to which a hydrogen atom or a substituent is bonded, Ax represents an organic group which has 1 to 30 carbon atoms and has at least one aromatic ring selected from the group consisting of an aromatic hydrocarbon ring and an aromatic heterocyclic ring; Ay represents a hydrogen atom, an alkyl group which has 1 to 6 carbon atoms and may have a substituent, or an organic group which has 1 to 30 carbon atoms and has at least one aromatic ring selected from the group consisting of an aromatic hydrocarbon ring and an aromatic heterocyclic ring; the aromatic ring included in Ax and Ay may have a substituent; and Ax and Ay may be bonded to each other to form a ring which may have a substituent, and $Q_2$ represents a hydrogen atom, or an alkyl group which has 1 to 6 carbon atoms and may have a substituent.

The symbol * indicates a bonding position with $L_1$ or $L_2$.

Regarding definitions and preferable ranges of respective substituents in General Formulas 21-1 to 21-4, descriptions of Y, $Q^1$, and $Q^2$ which relate to a compound (A) described in JP2012-021068A can be respectively referred to for $Y_1$, $Z_1$, and $Z_2$; descriptions of $A_1$, $A_2$, and X which relate to a compound represented by General Formula (I) described in JP2008-107767A can be respectively referred to for $A_1$, $A_2$, and X; descriptions of $A^x$, $A^y$, and $Q^1$ which relate to a compound represented by General Formula (I) described in WO2013/018526A can be respectively referred to for Ax, Ay, and $Q_2$ of General Formula 21-3; and descriptions of $A^a$, $A^b$, and $Q^{11}$ which relate to a compound represented by General Formula (II) described in WO2013/018526A can be respectively referred to for Ax, Ay, and Q of General Formula 21-4. A description of $Q^1$ relating to a compound (A) described in JP2012-021068A can be referred to for $Z_3$.

X in General Formula 21-2 is preferably C to which two substituents are bonded, and both $A_1$ and $A_2$ are preferably —S—. In General Formula 21-3, as a ring in a case where Ax and Ay are bonded to each other to form a ring which may have a substituent, the ring is preferably an alicyclic hydrocarbon ring, an aromatic hydrocarbon ring, or an aromatic heterocyclic ring, and is more preferably an aromatic heterocyclic ring. In General Formula 21-4, as a ring in a case where Ax and Ay are bonded to each other to form a ring which may have a substituent, the ring is preferably an unsaturated hydrocarbon ring.

$Ar_{21}$ in General Formula 1 is preferably an aromatic ring group represented by General Formula 21-2.

The aromatic ring group represented by General Formula 21-2 is particularly preferably an aromatic ring group represented by General Formula 21-2-1.

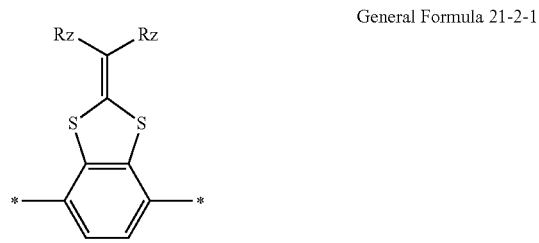

General Formula 21-2-1

In the formula, Rz represents a substituent. Examples of substituents represented by Rz include a substituent exemplified as a substituent of $Sp_1$ to be described later, and the like. Two Rz's may be the same as or different from each other. In addition, two Rz's may be bonded to each other to form a ring. The ring formed in this case is preferably a 5-membered ring or 6-membered ring, and is more preferably a 5-membered ring or 6-membered ring containing nitrogen or oxygen as an element constituting the ring. The ring is particularly preferably a ring represented by any of the following formulas.

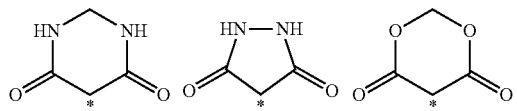

In the above formula, the symbol * each represent a position of a carbon atom to which two Rz's are bonded in General Formula 21-2-1. In addition, the ring represented by the above formula may have a substituent in nitrogen or carbon. In this case, the substituent is preferably an alkyl group having 1 to 6 carbon atoms, and is more preferably a linear alkyl group having 1 to 4 carbon atoms.

The aromatic ring group represented by General Formula 21-2-1 is preferably an aromatic ring group in which at least one of Rz's is a cyano group, or an aromatic ring group in which two Rz's are bonded to form a ring, and is more preferably an aromatic ring group in which two Rz's are both cyano groups.

The reason for this is because, in the lens adhesive including the compound represented by General Formula 1 having such an aromatic ring group, it is possible to obtain a more remarkable effect of increasing absorption in an ultraviolet range while maintaining high transitivity in a visible light region.

In General Formula 1, $L_1$ and $L_2$ are each independently synonymous with L described above, and preferable ranges thereof are also the same.

In General Formula 1, $Sp_1$ and $Sp_2$ are each independently synonymous with Sp described above, and preferable ranges thereof are also the same.

In General Formula 1, $Pol_1$ and $Pol_2$ are each independently synonymous with Pol described above, and preferable ranges thereof are also the same.

Examples of specific structures of $Pol_1$-$Sp_1$-$L_1$- or $Pol_2$-$Sp_2$-$L_2$- include the same examples as the examples for Pol-Sp-L- described above.

Specific examples of the compound represented by General Formula 1 which is preferably used in the lens adhesive of the present invention are listed below, but examples are not limited to the following compounds. In the following structural formulas, Me represents a methyl group, Et represents an ethyl group, nPr represents an n-propyl group, iPr represents an isopropyl group, nBu represents an n-butyl group, and tBu represents a t-butyl group.

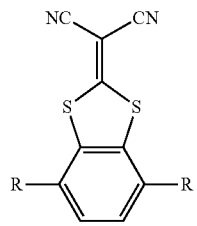

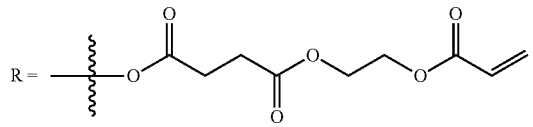

(I$_x$-1)

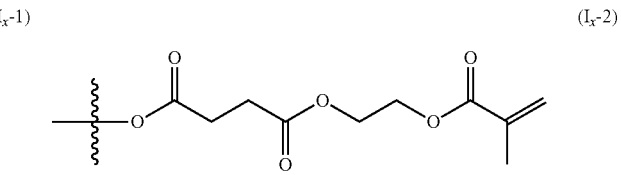

(I$_x$-2)

-continued
(I$_x$-3)
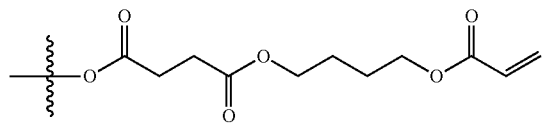
(I$_x$-4)
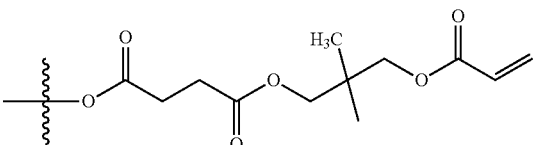
(I$_x$-5)
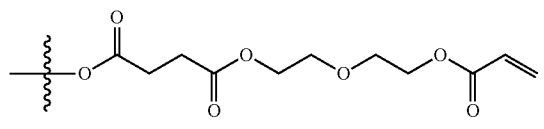
(I$_x$-6)
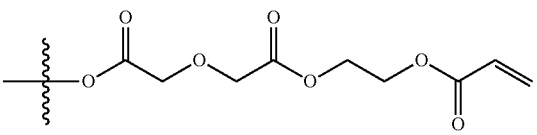
(I$_x$-7)
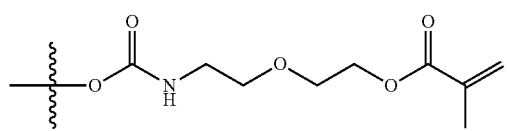
(I$_x$-8)
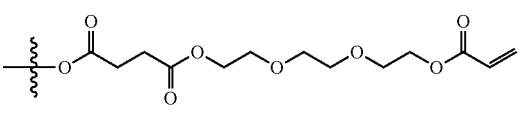
(I$_x$-9)
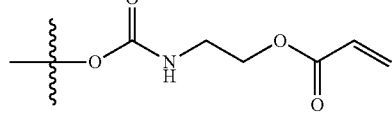
(I$_x$-10)
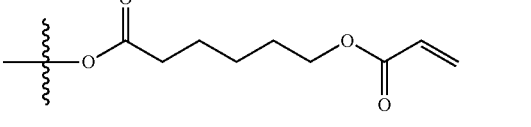
(I$_x$-11)
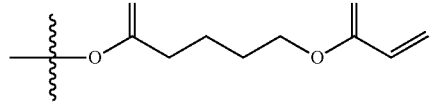
(I$_x$-12)
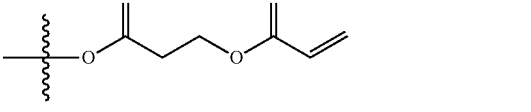
(I$_x$-13)
R = 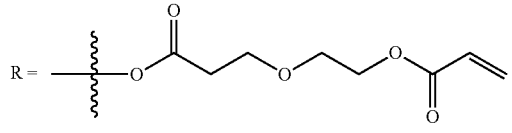
(I$_x$-14)
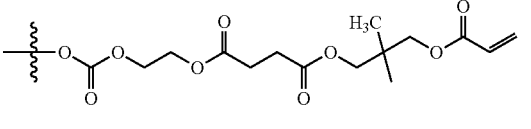
(I$_x$-15)
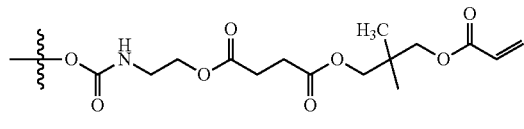
(I$_x$-16)
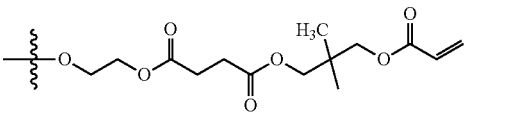
(I$_x$-17)
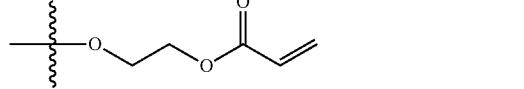
(I$_x$-18)
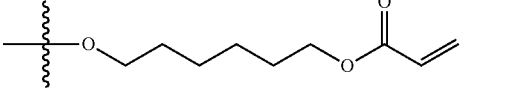
(I$_x$-19)
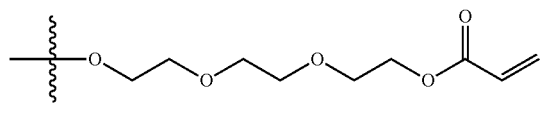
(I$_x$-20)
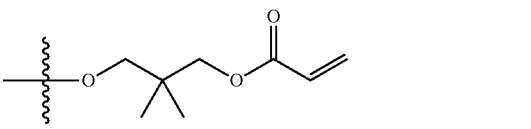
(I$_x$-21)
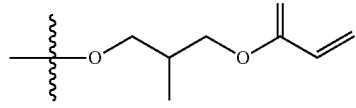
(I$_x$-22)
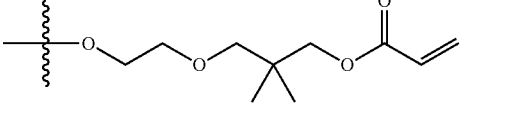

-continued
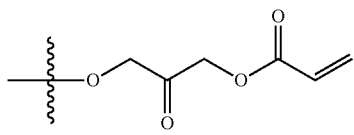
(I_x-23)
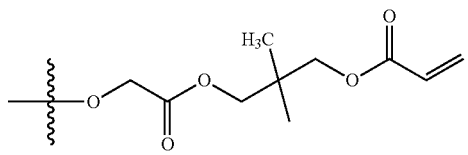
(I_x-24)
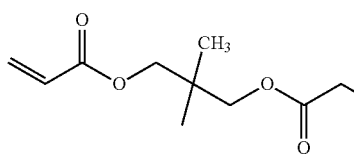
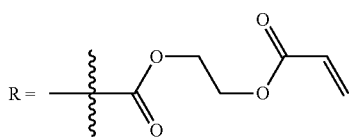
R =
(III_x-1)
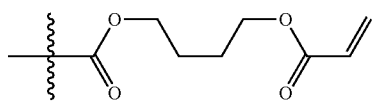
(III_x-2)
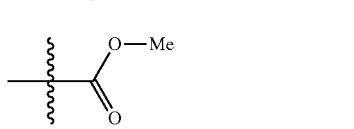
(III_x-3)
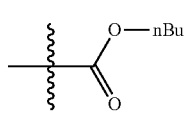
(III_x-4)
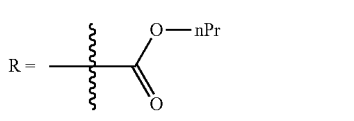
(III_x-5)
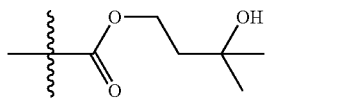
(III_x-6)
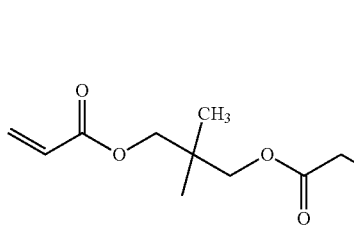
(III_x-7)
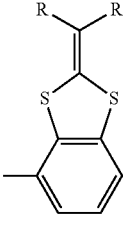
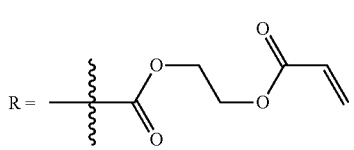
R =
(III_x-8)
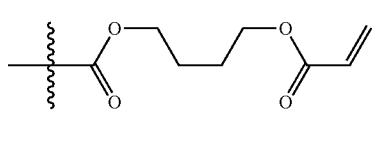
(III_x-9)
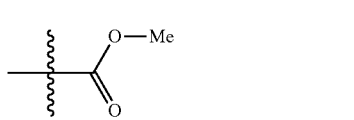
(III_x-10)
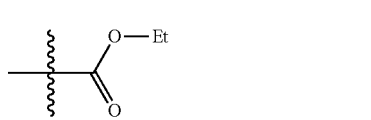
(III_x-11)
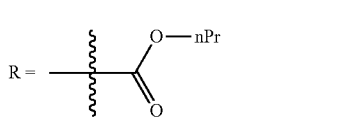
R =
(III_x-12)
(III_x-13)
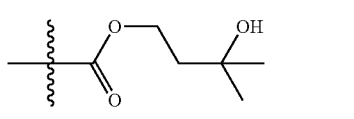
(III_x-14)

-continued
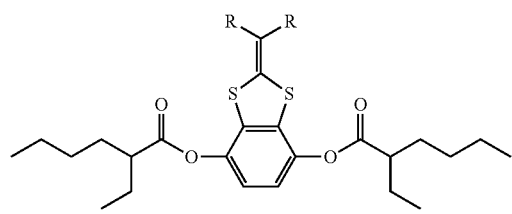
(III$_x$-15)
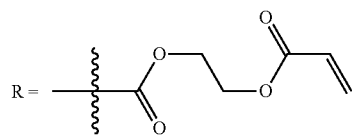
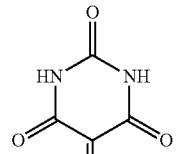
(III$_x$-16)
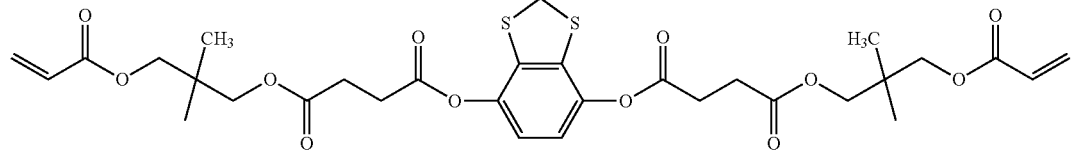
(III$_x$-17)
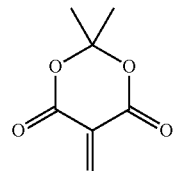
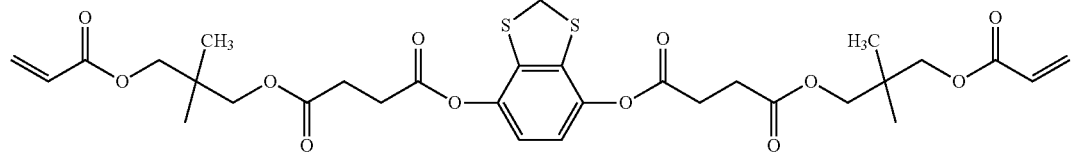
(III$_x$-18)
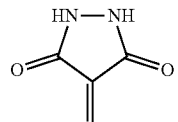
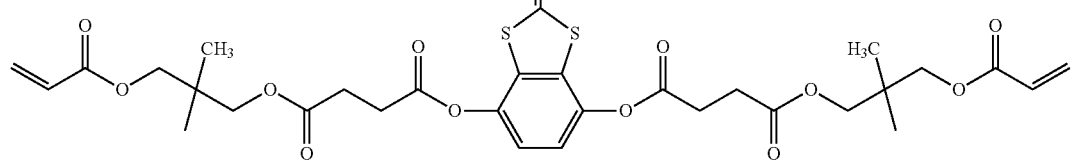
(III$_x$-19)
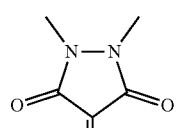
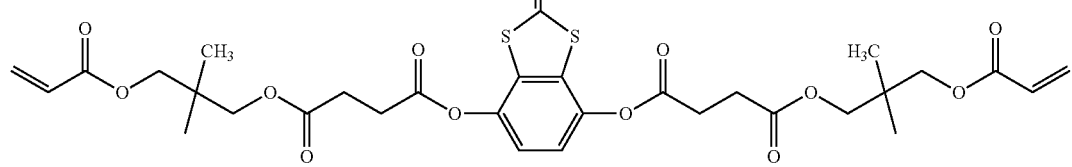
(III$_x$-20)

-continued
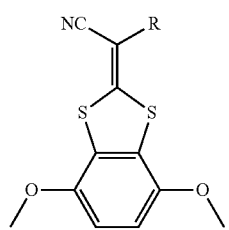
(III$_x$-21)
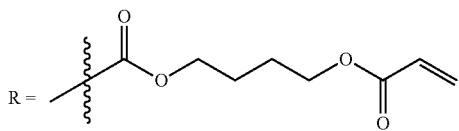
(III$_x$-22)
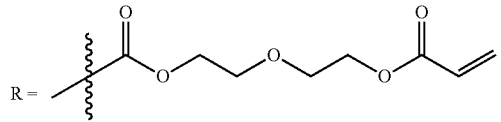
(III$_x$-23)
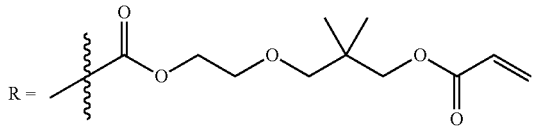
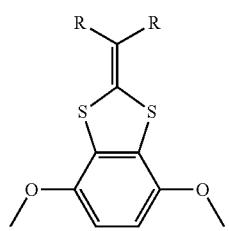
(III$_x$-24)
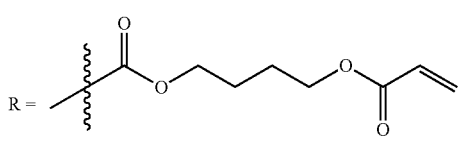
(III$_x$-25)
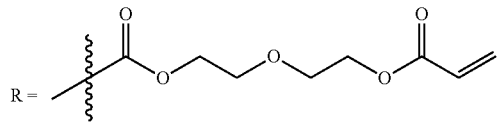
(III$_x$-26)
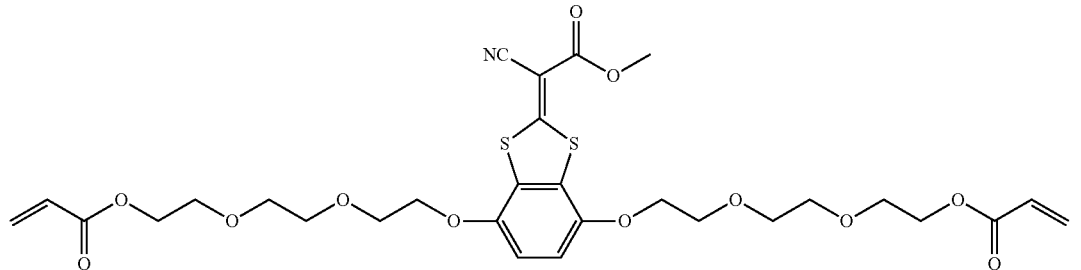
(III$_x$-27)
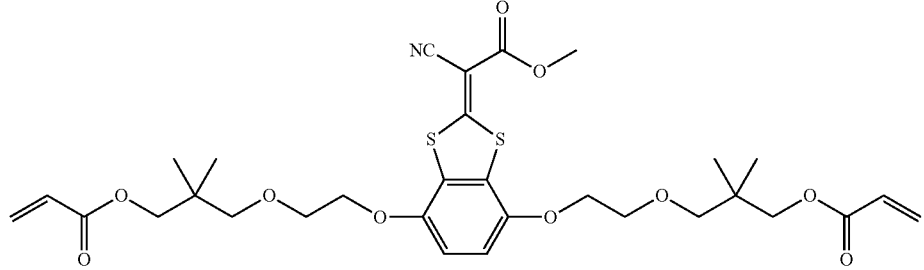
(III$_x$-28)
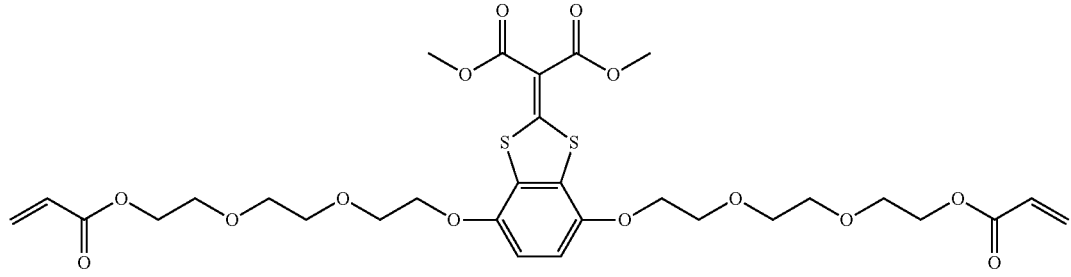

-continued
(III$_x$-30)
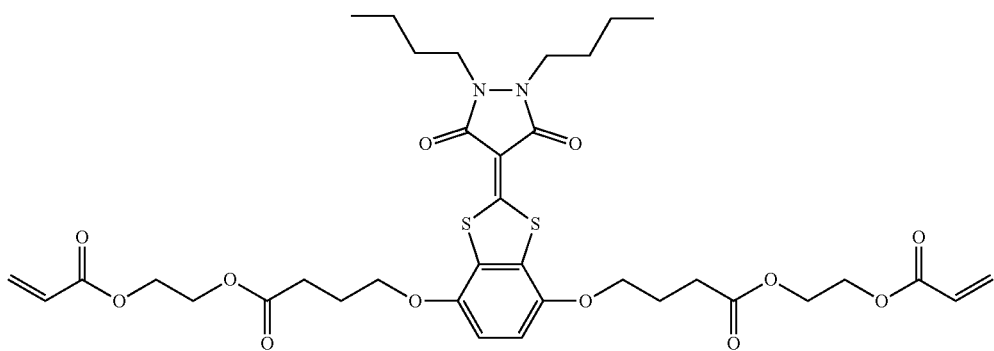
(III$_x$-31)
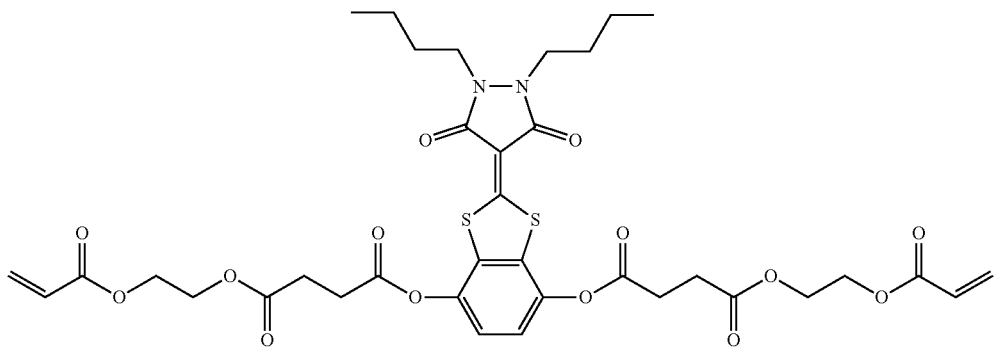
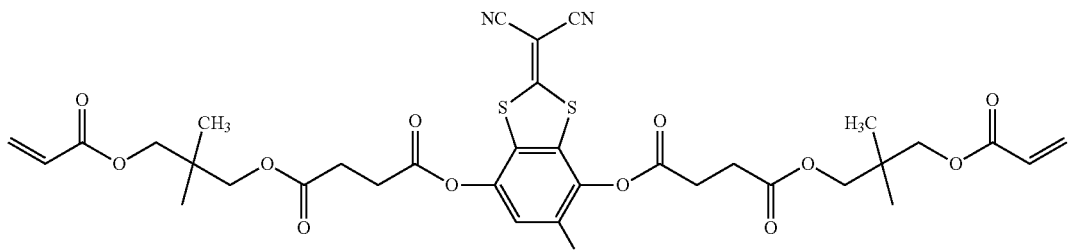
R = 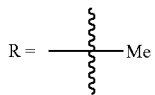 Me (IV$_x$-1)      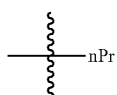 Et (IV$_x$-2)
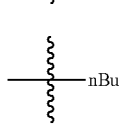 nPr (IV$_x$-3)     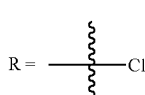 iPr (IV$_x$-4)
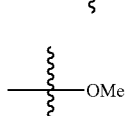 nBu (IV$_x$-5)     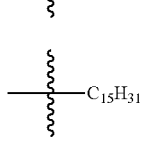 tBu (IV$_x$-6)
R = 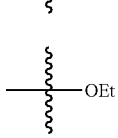 Cl (IV$_x$-7)     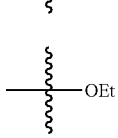 F (IV$_x$-8)
—OMe (IV$_x$-9)     —OEt (IV$_x$-10)
—C$_{15}$H$_{31}$ (IV$_x$-11)

-continued
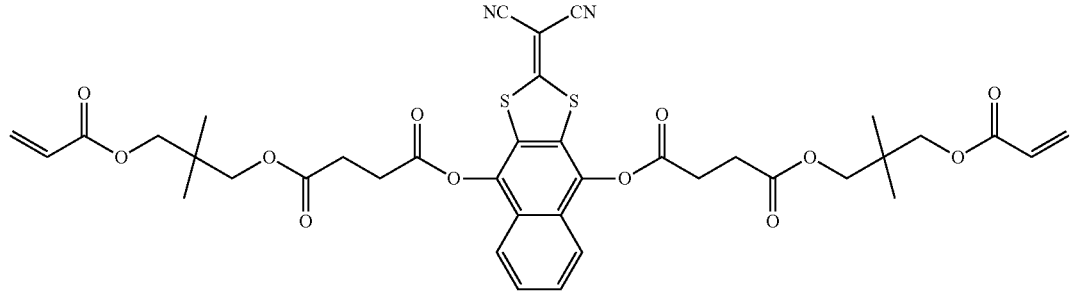
(IV$_x$-12)
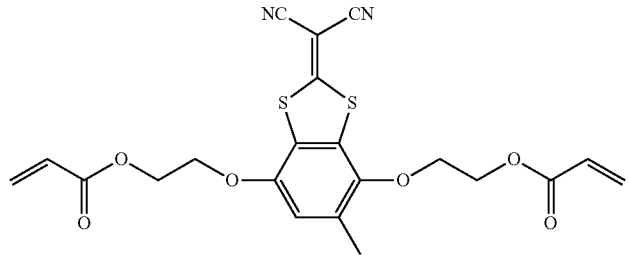
(IV$_x$-13)
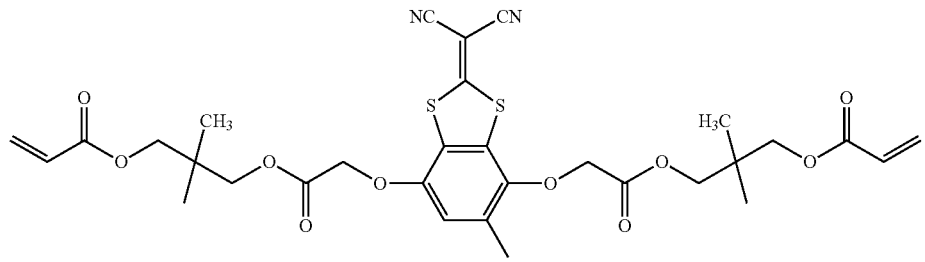
(IV$_x$-14)
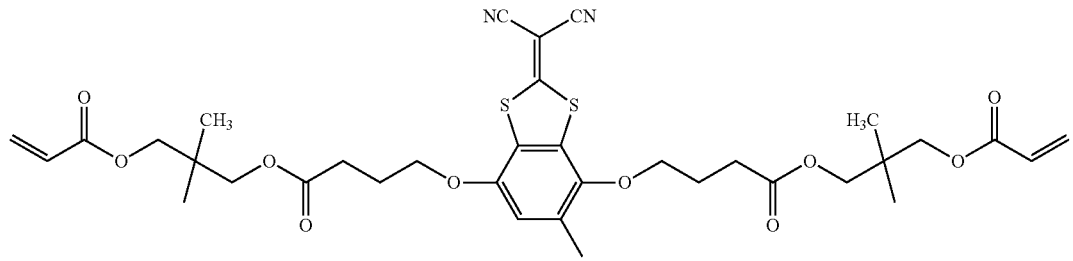
(IV$_x$-15)
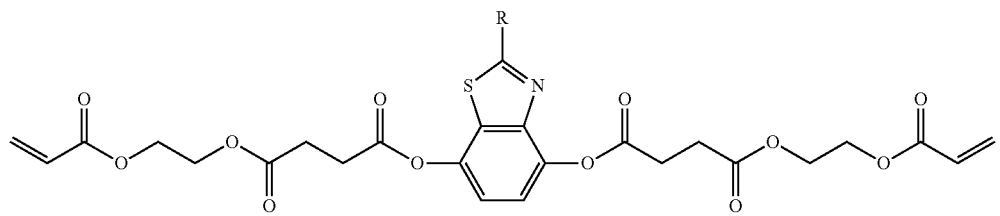
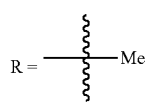
(V$_x$-1)
R = —Me
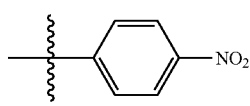
(V$_x$-2)
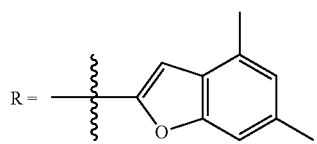
(V$_x$-3)
R =
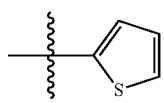
(V$_x$-4)

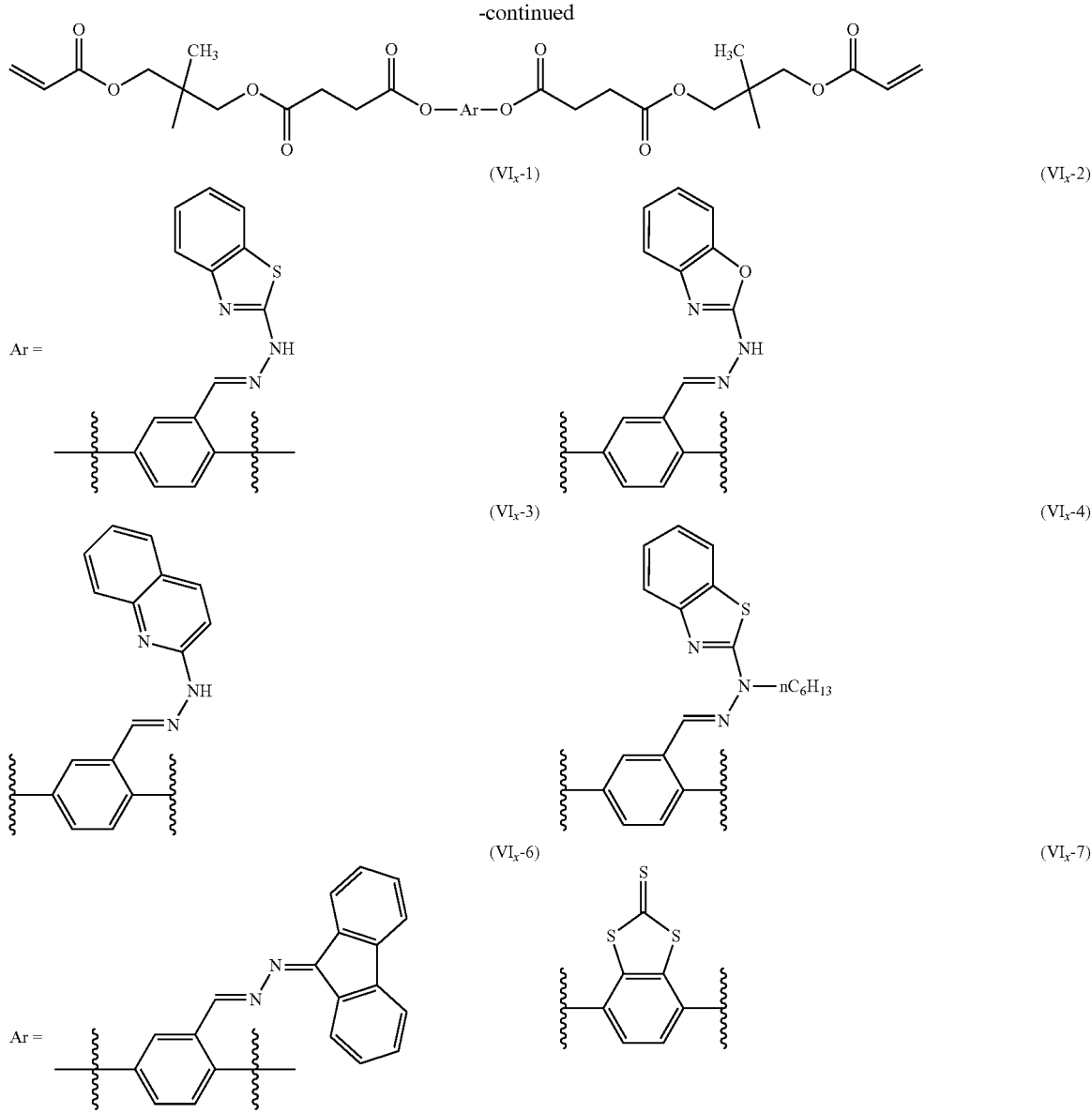

The compound represented by General Formula 1 has one or two or more asymmetrical carbon atoms in some cases, and stereochemical labels of such asymmetrical carbon atoms each independently may be any of rectus (R) or sinister (S). In addition, the compound represented by Formula (A) may be a mixture of stereoisomers such as optical isomers or diastereoisomers. In other words, the compound represented by Formula (A) may be any kind of stereoisomer, may be any mixture of stereoisomers, or may be a racemate.

A content of the compound represented by General Formula 1 in the lens adhesive is preferably 10% by mass to 90% by mass, is more preferably 15% by mass to 85% by mass, and is even more preferably 20% by mass to 80% by mass with respect to a total mass of the lens adhesive. By setting the content thereof to 90% by mass or less, a viscosity can be set within a preferable range.

Two or more compounds represented by General Formula 1 may be contained in the lens adhesive. In a case where two or more compounds represented by General Formula 1 are contained, a total content thereof is preferably within the above-mentioned range.

(Polymer)

The lens adhesive may include a polymer or an oligomer (hereinafter also referred to as a "polymer") for the purpose of adjusting a viscosity or a Young's modulus of a cured product. The polymer is not particularly limited, but it is preferably a polymer having an ethylenically unsaturated group. The ethylenically unsaturated group may be contained in any of the inside of a main chain, a terminal of the main chain, or a side chain of the polymer. The ethylenically unsaturated group is not particularly limited, but it is preferably an ethylenically unsaturated bond derived from butadiene or isoprene, or a (meth)acryloyl group.

The polymer contained in the lens adhesive is preferably a polymer selected from the group consisting of a conjugated diene polymer and a polyurethane resin having an ethylenically unsaturated group, and is more preferably a polymer having a polybutadiene structure, a polymer having a polyisoprene structure, and a polymer selected from the group consisting of urethane (meth)acrylates.

Commercially available products of a polymer having a polybutadiene structure include, for example, NIPOL BR series (manufactured by Zeon Corporation), UBEPOL BR series (manufactured by UBE INDUSTRIES, LTD.), NISSO-PB series (manufactured by Nippon Soda Co., Ltd.), KURARAY LIQUID RUBBER LBR series and KURARAY LIQUID RUBBER L-SBR series (manufactured by Kuraray Co., Ltd.), and the like.

Commercially available products of a polymer having a polyisoprene structure include, for example, NIPOL IR series (manufactured by Zeon Corporation), KURARAY LIQUID RUBBER LIR series and KURARAY LIQUID RUBBER UC series (manufactured by Kuraray Co., Ltd.), and the like.

Commercially available products of urethane (meth)acrylate include, for example, UV-3200, UV-3000B, UV-3700B, UV-3210EA, UV-2000B, and UV-3630 of SHIKOH (registered trademark) series (all of which are manufactured by Nippon Synthetic Chemical Industry Co., Ltd.), EBECRYL 230 and EBECRYL 9227EA (which are manufactured by Daicel Psytech Co., Ltd.), AU-3040, AU-3050, AU-3090, AU-3110, and AU-3120 of Hi-Cope AU (registered trademark) series (all of which are manufactured by TOKUSHIKI CO., Ltd.), and the like.

A molecular weight of the polymer is preferably 1,000 or more, more preferably 3,000 or more, and even more preferably 5,000 or more in terms of weight-average molecular weight (GPC, in terms of polystyrene). In addition, a molecular weight of the polymer is preferably 500,000 or less, more preferably 300,000 or less, and even more preferably 100,000 or less in terms of weight-average molecular weight (GPC, in terms of polystyrene).

A content of the polymer is preferably 50% by mass or less, more preferably 40% by mass or less, and even more preferably 30% by mass or less with respect to a total mass of the lens adhesive.

((Meth)Acrylate Monomer)

The lens adhesive may include a (meth)acrylate monomer. As the (meth)acrylate monomer, the same monomer as those exemplified for the above-described curable composition can be used.

Preferred examples of (meth)acrylate monomers contained in the lens adhesive include a monofunctional (meth) acrylate monomer having an aromatic ring such as phenoxyethyl acrylate (the above-mentioned monomer 1) or benzyl acrylate; and a (meth)acrylate monomer having an aliphatic group, such as a monomer a (2-ethylhexyl acrylate), a monomer b (1,6-hexanediol diacrylate), or a monomer c (1,6-hexanediol dimethacrylate); and a (meth)acrylate monomer having a hydroxy group such as a monomer d (2-hydroxyethyl acrylate), a monomer e (hydroxypropyl acrylate), or a monomer f (4-hydroxybutyl acrylate).

Monomer a

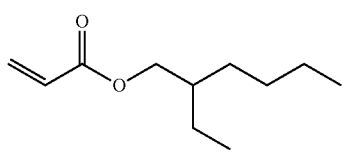

Monomer b

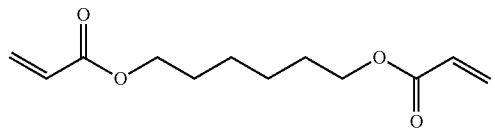

Monomer c

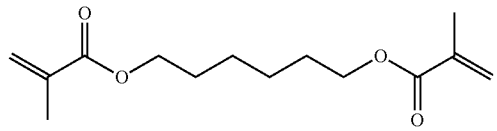

Monomer d

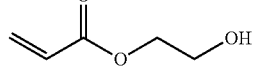

Monomer e

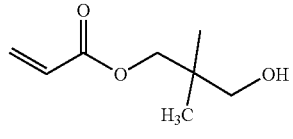

Monomer f

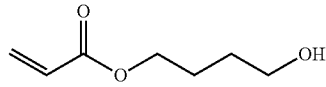

A method of obtaining a (meth)acrylate monomer is not particularly limited, and a commercially available monomer may be used, or it may be manufactured by synthesis. In a case where the compound is commercially available, for example, it is possible to preferably use VISCOAT #192 PEA (phenoxyethyl acrylate) (manufactured by OSAKA ORGANIC CHEMICAL INDUSTRY LTD.), VISCOAT #160 BZA (benzyl acrylate) (manufactured by OSAKA ORGANIC CHEMICAL INDUSTRY LTD.), 2EHA (monomer a) (manufactured by Toagosei Co., Ltd.), A-HD-N (monomer b) (manufactured by Shin-Nakamura Chemical Co., Ltd.), HD-N (monomer c) (manufactured by Shin-Nakamura Chemical Co., Ltd.), HEA (monomer d) (manufactured by OSAKA ORGANIC CHEMICAL INDUSTRY LTD.), LIGHT ESTER HOP-A (N) (monomer e) (manufactured by KYOEISHA CHEMICAL Co., LTD.), and 4-HBA (monomer f) (manufactured by OSAKA ORGANIC CHEMICAL INDUSTRY LTD.).

In a case where the lens adhesive of the embodiment of the present invention contains a (meth)acrylate monomer, a content of the (meth)acrylate monomer is preferably 5% to 90% by mass, more preferably 10% to 85% by mass, and even more preferably 20% to 80% by mass, with respect to a total mass of the lens adhesive. By adjusting an amount of (meth)acrylate monomer in the lens adhesive, it is possible to adjust a function of relaxing stress when a cured product is deformed by heat.

(Polymerization Initiator)

The lens adhesive preferably contains a photoradical polymerization initiator. As the photoradical polymerization initiator, the same initiator as those exemplified for the above-described curable composition can be used in the same amount.

Furthermore, the lens adhesive may include a thermal radical polymerization initiator in addition to the photoradical polymerization initiator. By further including a thermal radical polymerization initiator, it is possible to promote curing of a region where light does not reach. As the thermal radical polymerization initiator, the same initiator as those exemplified for the above-described curable composition can be used in the same amount.

[Manufacture of Cemented Lenses]

The cemented lens can be obtained by superimposing two lenses using the lens adhesive, and then curing the adhesive to form the adhesive layer as described later. The curing is preferably performed after removing air bubbles mixed into the adhesive after the superimposition.

Curing of the adhesive can be performed by light irradiation or heating. The curing is preferably performed by carrying out at least light irradiation. In addition, a step of further heating may be performed after light irradiation.

A thickness of the adhesive layer is preferably 10 to 50 μm, and more preferably 20 to 30 μm. In a case where the thickness is 10 μm or more, an effect of absorbing ultraviolet rays can be sufficiently obtained. In addition, in a case where the thickness is 50 μm or less, it is possible to improve transmittance in a short wavelength range (400 to 430 nm) of visible light while exhibiting high adhesiveness.

A refractive index of the adhesive layer at a wavelength of 587 nm is preferably 1.51 or more, more preferably 1.53 or more, and even more preferably 1.55 or more. The reason for this is because a difference in refractive indices from a lens to be cemented becomes small.

In addition, a cutoff wavelength of the adhesive layer having a thickness of 30 μm is preferably 380 nm or less, more preferably 385 nm or less, and even more preferably 390 nm or less. A wavelength at which transmittance of the adhesive layer becomes 0.5% or less is defined as a cutoff wavelength. The transmittance of the adhesive layer can be measured using a spectrophotometer (for example, UV-2550 manufactured by Shimadzu Corporation).

A refractive index and a cutoff wavelength of the adhesive layer can be adjusted within the above-mentioned range by an amount of the compound represented by General Formula 1 in the lens adhesive.

EXAMPLES

Hereinafter, the features of the present invention will be more specifically described with reference to examples and comparative examples. In the following examples, materials, amounts used, ratios, details of treatments, treatment procedures, and the like may be suitably modified without departing from the gist of the present invention. Accordingly, the scope of the present invention should not be limitedly interpreted by the following specific examples.

Synthesis Example 1

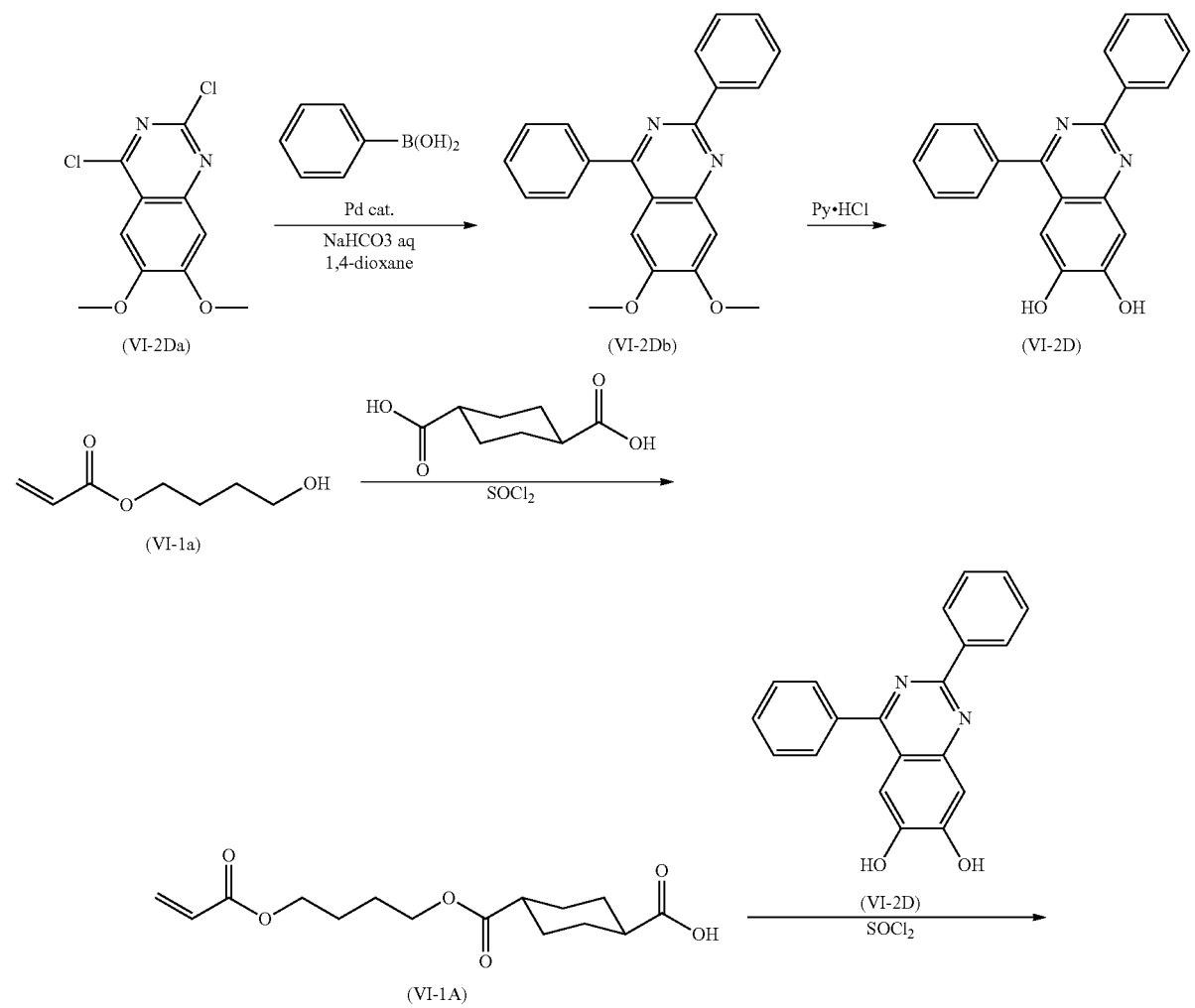

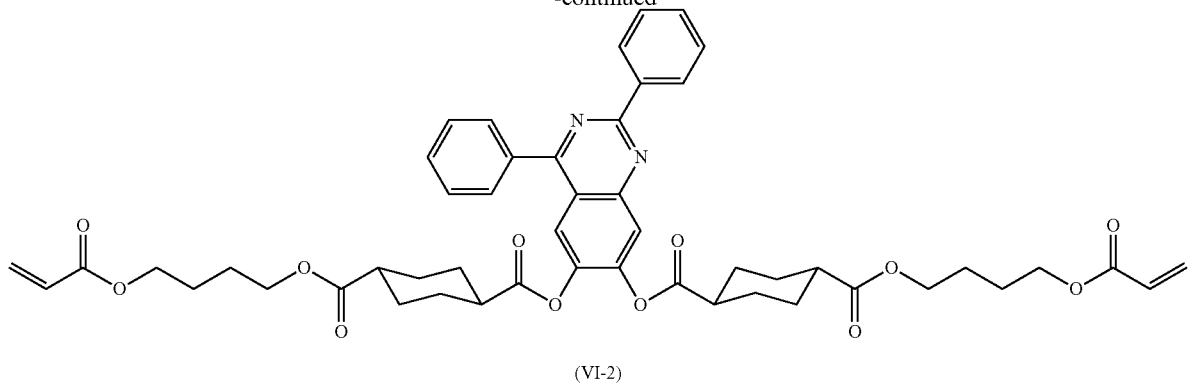

(VI-2)

Synthesis of Compound (VI-2db)

5.0 g (19.3 mmol) of 2,4-dichloro-6,7-dimethoxyquinazoline (VI-2 Da), 7.1 g (57.9 mmol) of phenylboronic acid, 1.1 g of dichlorobis[di-t-butyl(p-dimethylaminophenyl)phosphino]palladium (II), 100 mL of 1,4-dioxane, and 100 mL of an aqueous solution of saturated sodium bicarbonate were mixed under a nitrogen atmosphere. After stirring the mixture at an internal temperature of 85° C. for 2 hours, the mixture was cooled to 25° C., ethyl acetate (300 mL) and water (200 mL) were added thereto, and the mixture was washed and separated. Thereafter, the mixture was concentrated and purified by column chromatography (yield 77%).

Synthesis of Compound (VI-2D)

After mixing 5.0 g of the compound (VI-2db) and 50 g of pyridine hydrochloride, the mixture was stirred at 190° C. for 4 hours under a nitrogen atmosphere. Thereafter, 300 mL of water was added dropwise at 80° C. to precipitate a solid, and then the solid was cooled to 25° C. After the solid was filtered, it was washed with a water-methanol mixed solvent with a volume ratio of 3:1 (yield 95%).

Synthesis of Compound (VI-1A)

A compound (VI-1A) was synthesized according to a method described in paragraph 0113 of JP2016-053149A.

Synthesis of Compound (VI-2)

20.1 g (67.4 mmol) of the carboxylic acid compound (VI-1A), 185 mL of ethyl acetate, 46 mL of N,N-dimethylacetamide, and 60 mg of 2,6-di-t-butyl-4-methylphenol were mixed, and an internal temperature was cooled to 0° C. To the mixture, 7.75 g (65.1 mmol) of thionyl chloride was added dropwise at an internal temperature of 0° C. to 5° C. After stirring at 5° C. for 60 minutes, a solution of 8.7 g (27.6 mmol) of the compound (VI-2D) and 52 mL of THF was added dropwise at an internal temperature of 0° C. to 8° C.

Thereafter, 16.8 g of N,N-diisopropylethylamine was added dropwise at an internal temperature of 0° C. to 10° C. After stirring at an internal temperature of 20° C. to 25° C. for 1 hour, 40 mL of ethyl acetate, 165 mL of water, and 14 mL of concentrated hydrochloric acid were added and washed. The organic layer was washed with 140 mL of saturated saline and separated, and then washed with 100 mL of saturated saline and 10 mL of 7.5% by mass sodium bicarbonate water to be separated. Thereafter, concentration was performed to obtain an oily composition, which was then purified by column chromatography (yield 38%).

$^1$H-NMR (300 MHz, CDCl$_3$): δ (ppm) 1.40-1.60 (m, 8H), 1.60-1.80 (m, 8H), 2.00-2.20 (m, 8H), 2.20-2.40 (m, 4H), 4.15 (t, 4H), 4.24 (t, 4H), 5.84 (dd, 2H), 6.05-6.15 (m, 2H), 6.40 (dd, 2H), 7.35 (s, 2H), 7.45-7.55 (m, 6H), 7.60-7.70 (m, 4H)

Synthesis Example 2

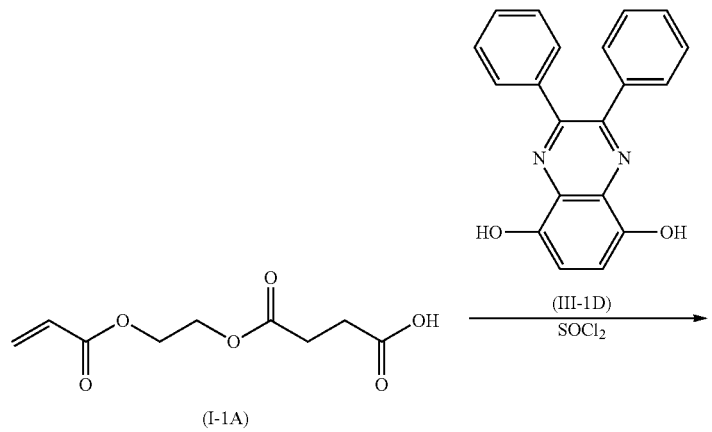

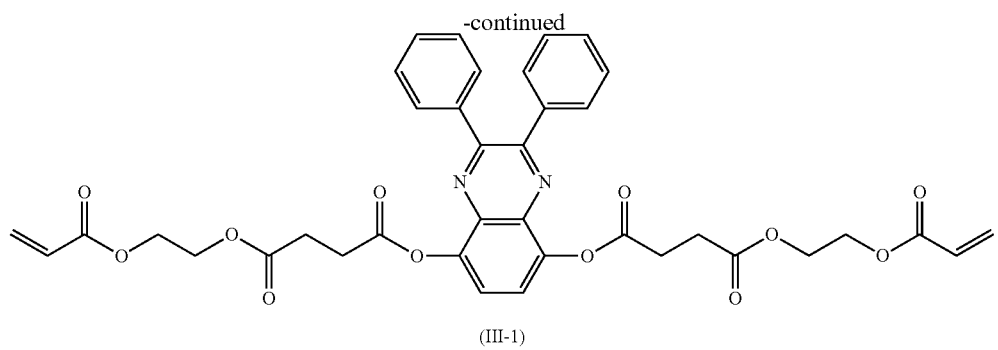

(III-1)

Synthesis of Compound (III-1D)

A compound (III-1D) was synthesized by the same method as in the synthesis of a compound (ex-2) described in Example 1 of JP2017-125009A, except that phenylglyoxal was changed to benzyl (yield 35%).

Synthesis of Compound (III-1)

7.3 g (33.7 mmol) of the carboxylic acid compound (I-1A), 93 mL of ethyl acetate, 23 mL of N,N-dimethylacetamide, and 30 mg of 2,6-di-t-butyl-4-methylphenol were mixed, and an internal temperature was cooled to 0° C. To the mixture, 3.88 g (32.6 mmol) of thionyl chloride was added dropwise at an internal temperature of 0° C. to 5° C. After stirring at 5° C. for 60 minutes, a solution of 4.3 g (13.8 mmol) of the compound (III-1D) and 26 mL of THF was added dropwise at an internal temperature of 0° C. to 8° C.

Thereafter, 8.4 g of N,N-diisopropylethylamine was added dropwise at an internal temperature of 0° C. to 10° C. After stirring at an internal temperature of 20° C. to 25° C. for 1 hour, 20 mL of ethyl acetate, 82.5 mL of water, and 7 mL of concentrated hydrochloric acid were added and washed. The organic layer was washed with 70 mL of saturated saline and separated, and then washed with 50 mL of saturated saline and 5 mL of 7.5% by mass sodium bicarbonate water to be separated. Thereafter, concentration was performed to obtain an oily composition, which was then purified by column chromatography (yield 81%).

$^1$H-NMR (300 MHz, CDCl$_3$): δ (ppm) 2.80 (t, 4H), 2.95 (t, 4H), 4.30-4.40 (m, 8H), 5.85 (d, 2H), 6.05-6.15 (m, 2H), 6.43 (d, 2H), 7.35 (s, 2H), 7.45-7.60 (m, 6H), 7.60-7.70 (m, 4H)

Synthesis Example 3

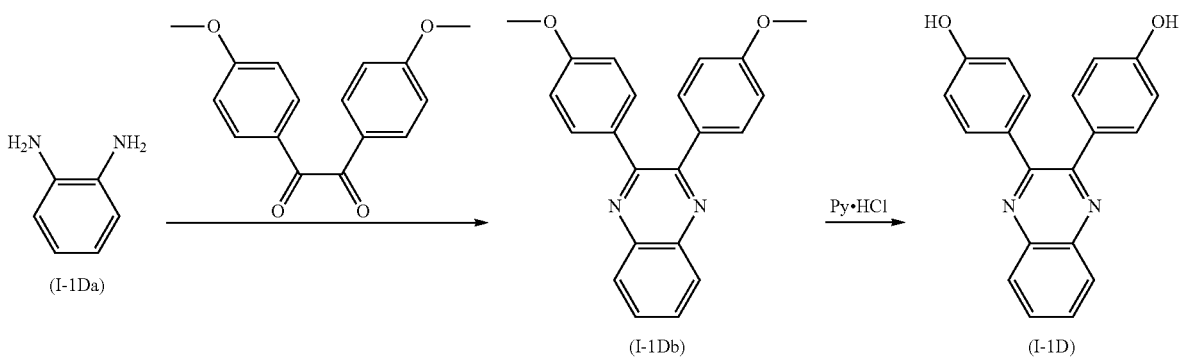

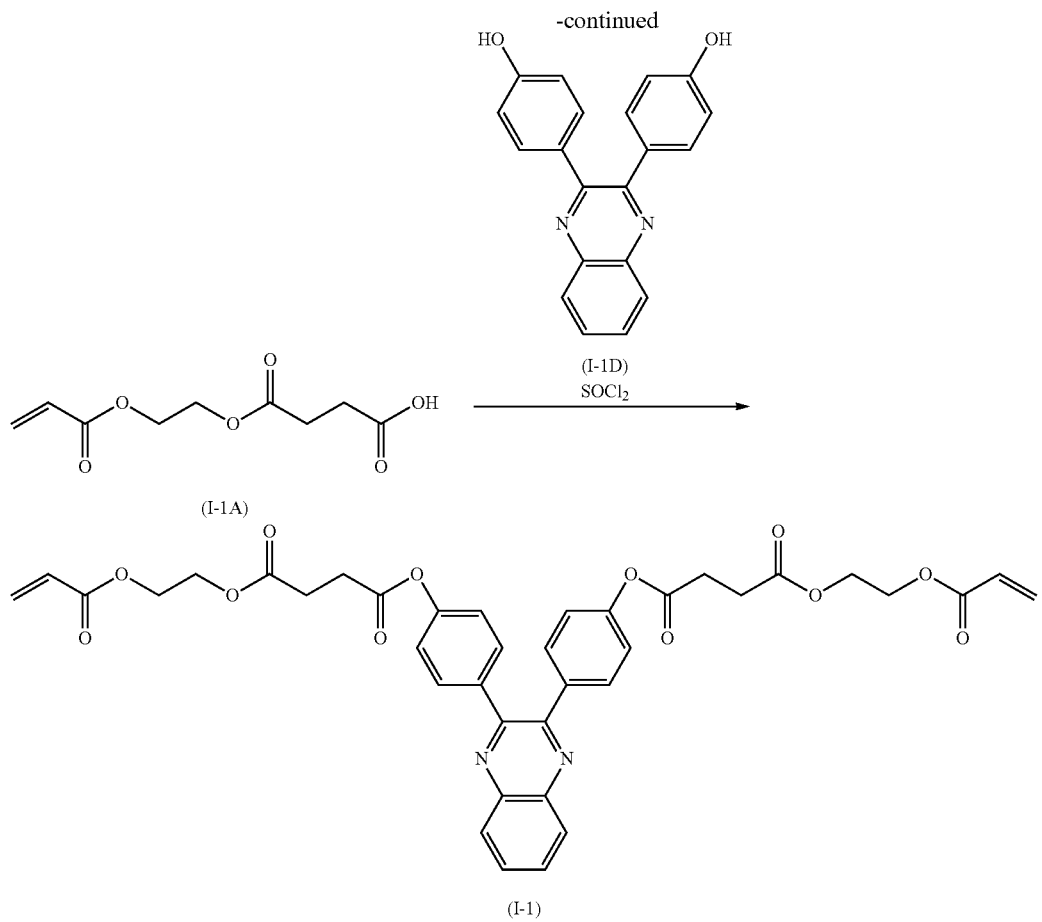

Synthesis of Compound (I-1db)

After mixing 5.0 g (46.2 mmol) of 1,2-phenylenediamine (I-1 Da), 12.5 g (46.2 mmol) of p-anisyl, and 80 mL of acetic acid, 125 mg of 2-iodoxybenzoic acid was added. After stirring the mixture at 25° C. for 2 hours, the precipitated compound (I-db) was filtered and washed with 50 mL of methanol (yield 65%).

Synthesis of Compound (I-1D)

A compound (I-1D) (yield 93%) was obtained by the same method except that the compound (VI-2db) in the synthesis of the compound (VI-2D) of Synthesis Example 1 was changed to the compound (I-db).

Synthesis of Compound (I-1)

A compound (I-1) (yield 75%) was obtained in the same manner as in Synthesis Example 2, except that the compound (III-1D) described in Synthesis Example 2 was changed to the compound (I-1D).

$^1$H-NMR (300 MHz, CDCl$_3$): δ (ppm) 2.80 (t, 4H), 2.92 (t, 4H), 4.30-4.40 (m, 8H), 5.85 (d, 2H), 6.05-6.15 (m, 2H), 6.43 (d, 2H), 7.10 (d, 4H), 7.70 (d, 4H), 7.70-7.80 (m, 2H), 8.10-8.20 (m, 2H)

Synthesis Example 4

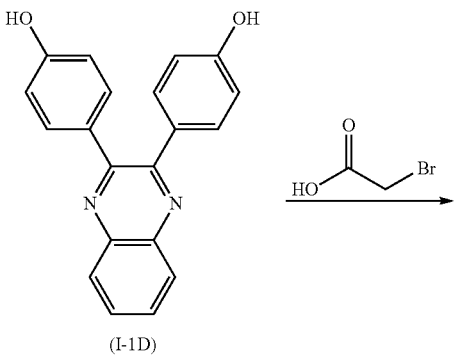

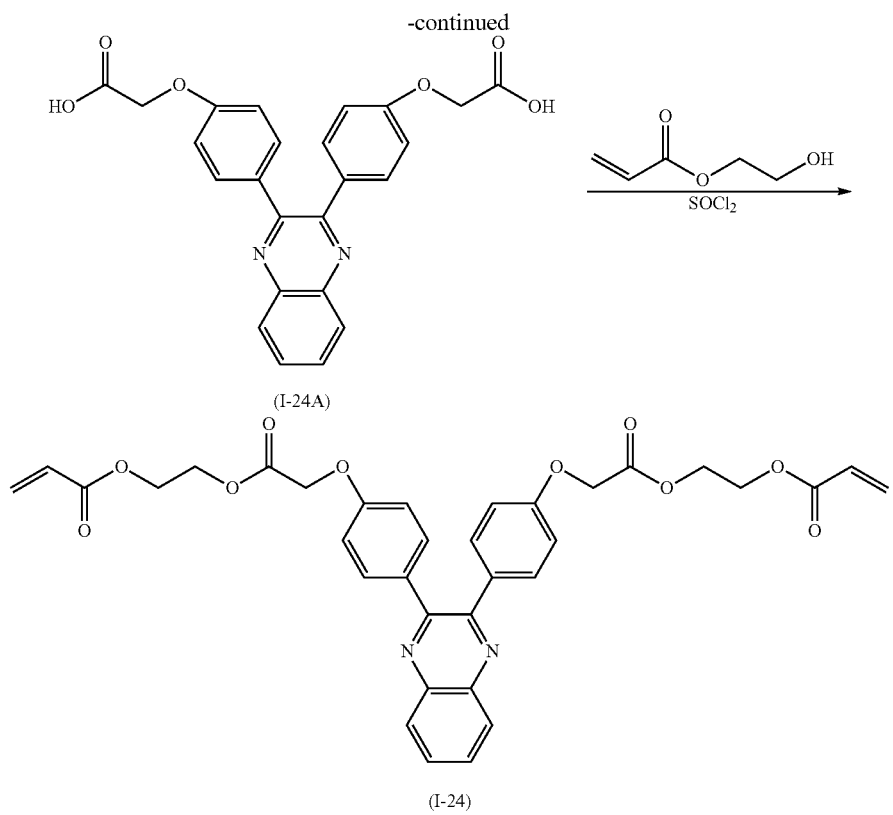

(I-24A)

(I-24)

Synthesis of Compound (I-24A)

After mixing 10.1 g (32.2 mmol) of the compound (I-1D), 10.3 g (74.1 mmol) of bromoacetic acid, 1 g of tetrabutylammonium bromide, 260 mL of THF, and 200 mL of N,N-dimethylacetamide, 23.6 g of potassium carbonate was added thereto in small portions. Thereafter, an internal temperature was raised to 80° C., and the mixture was stirred for 10 hours. Thereafter, after cooling to 25° C., the solution was added to 700 mL of 1N hydrochloric acid water, and the precipitated solid was filtered. The obtained solid was purified by column chromatography (yield 35%).

Synthesis of Compound (I-24)

7.3 g (16.9 mmol) of the carboxylic acid compound (I-24A), 93 mL of ethyl acetate, 30 mL of N,N-dimethylacetamide, and 30 mg of 2,6-di-t-butyl-4-methylphenol were mixed, and an internal temperature was cooled to 0° C. To the mixture, 3.88 g (32.6 mmol) of thionyl chloride was added dropwise at an internal temperature of 0° C. to 5° C. After stirring at 5° C. for 60 minutes, a solution of 4.3 g (37.2 mmol) of 2-hydroxyethyl acrylate and 26 mL of THF was added dropwise at an internal temperature of 0° C. to 8° C.

Thereafter, 8.4 g of N,N-diisopropylethylamine was added dropwise at an internal temperature of 0° C. to 10° C. After stirring at an internal temperature of 20° C. to 25° C. for 1 hour, 20 mL of ethyl acetate, 82.5 mL of water, and 7 mL of concentrated hydrochloric acid were added and washed. The organic layer was washed with 70 mL of saturated saline and separated, and then washed with 50 mL of saturated saline and 5 mL of 7.5% by mass sodium bicarbonate water to be separated. Thereafter, concentration was performed to obtain an oily composition, which was then purified by column chromatography (yield 73%).

$^1$H-NMR (300 MHz, CDCl$_3$): δ (ppm) 4.30-4.40 (m, 8H), 4.70 (s, 4H), 5.85 (d, 2H), 6.05-6.15 (m, 2H), 6.43 (d, 2H), 6.90 (d, 4H), 7.50 (d, 4H), 7.70-7.80 (m, 2H), 8.10-8.20 (m, 2H)

Synthesis Example 5

Synthesis of A-28

Synthesis was performed according to the description in paragraph 0139 of WO2017/115649A.

Synthesis Example 6

Synthesis of Intermediate 4

An intermediate 4 was synthesized according to the description in paragraph 0133 of WO2017/115649A.

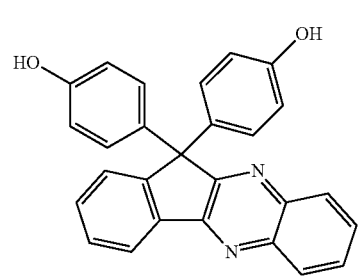

Intermediate 4

Synthesis of A-1

To a 200 mL three-neck flask, 4.8 g of an intermediate 4, 6.5 g of mono(2-acryloyloxyethyl) succinate, 140 mg of N,N-dimethylaminopyridine (DMAP), and 50 mL of dichloromethane were added and stirred in an ice bath for 10 minutes. 5.8 g of 1-(3-dimethylaminopropyl)-3-ethylcarbodiimide hydrochloride (EDAC·HCl) was added thereto, and the mixture was reacted at room temperature for 4 hours. The reaction solution was diluted with ethyl acetate, washed with water, an aqueous solution of saturated sodium bicarbonate, and saturated saline in this order, and then the organic layer was dried over magnesium sulfate. After removing magnesium sulfate by filtration, the residue was purified by silica gel column chromatography using hexane/ethyl acetate as a developing solvent, and thereby 7.5 g of a compound (A-1) was obtained. The $^1$H-NMR data of the compound (A-1) was as follows.

$^1$H-NMR (300 MHz, DMSO-$d_6$): δ2.60-2.70 ppm (m, 4H), 2.75-2.85 ppm (m, 4H), 4.25-4.35 ppm (m, 8H), 5.85-6.40 ppm (m, 6H), 7.00-7.10 ppm (d, 4H), 7.20-7.30 ppm (d, 4H), 7.55-7.70 ppm (m, 3H), 7.75-7.90 ppm (m, 2H), 8.05-8.15 ppm (d, 1H), 8.20-8.30 ppm (m, 2H)

Synthesis Example 7

Synthesis of A-2

A compound (A-2) was obtained by the same method as in the synthesis of the compound (A-1) of Synthesis Example 6 except that mono(2-acryloyloxyethyl) succinate was changed to mono(2-methacryloyloxyethyl) succinate.

$^1$H-NMR (300 MHz, DMSO-$d_6$): δ1.80 ppm (s, 6H), 2.60-2.70 ppm (m, 4H), 2.75-2.85 ppm (m, 4H), 4.25-4.35 ppm (m, 8H), 5.58 ppm (s, 2H), 5.97 ppm (s, 2H), 7.00-7.10 ppm (d, 4H), 7.20-7.30 ppm (d, 4H), 7.55-7.70 ppm (m, 3H), 7.75-7.90 ppm (m, 2H), 8.05-8.15 ppm (d, 1H), 8.20-8.30 ppm (m, 2H)

Synthesis Example 8

Synthesis of A-27

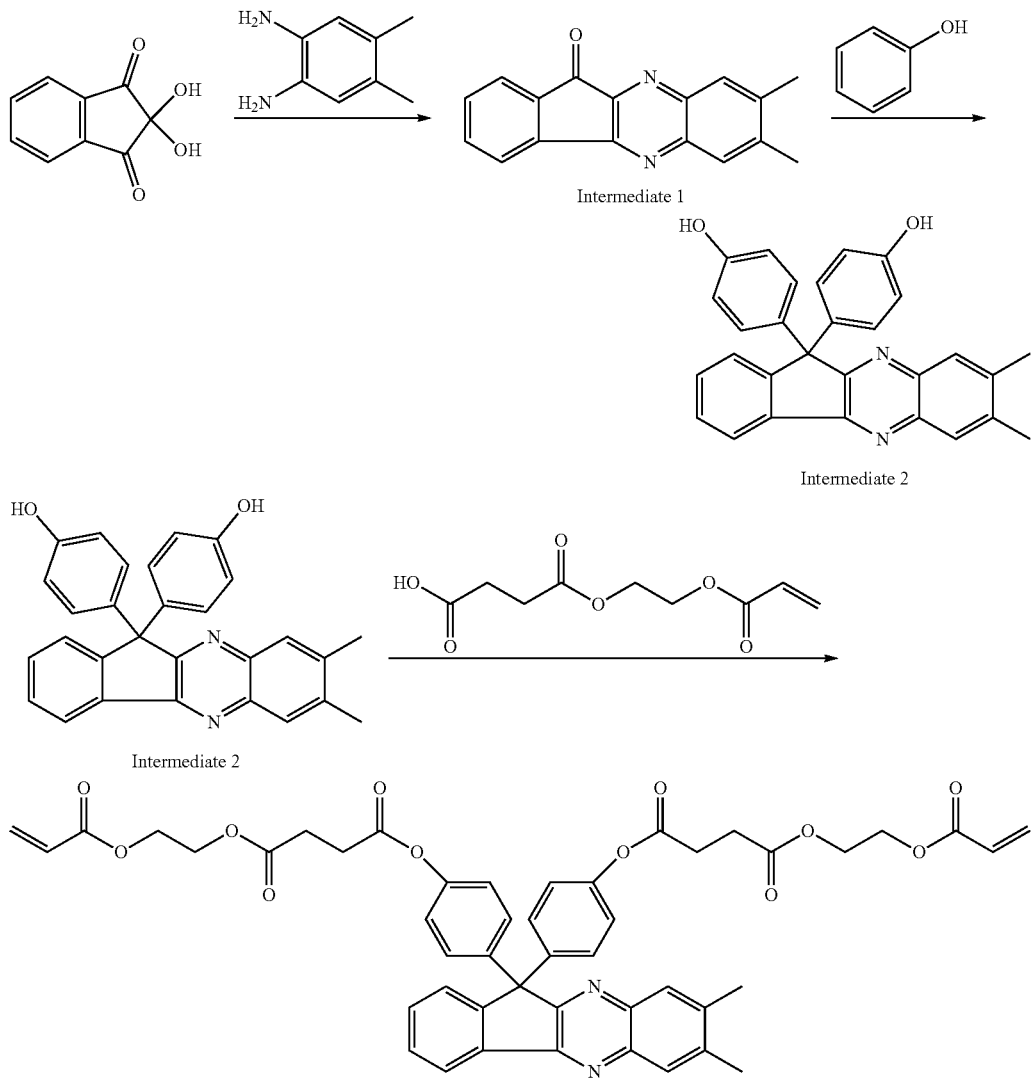

Synthesis of Intermediate 1

50 mL of ethanol and 10 mL of acetic acid were added to 25.6 g of 4,5-dimethyl-1,2-phenylenediamine and 35.6 g of ninhydrin, and the mixture was reacted at 70° C. for 3 hours. After cooling the reaction solution to room temperature, the precipitated crystals were collected by filtration, washed with ethanol, and dried, and thereby 41.1 g of an intermediate 1 was obtained.

$^1$H-NMR (300 MHz, CDCl$_3$): δ2.49 ppm (s, 3H), 2.51 ppm (s, 3H), 7.52-7.58 ppm (t, 1H), 7.71-7.76 ppm (t, 1H), 7.85-7.95 ppm (m, 3H), 8.02-8.08 ppm (d, 1H)

Synthesis of Intermediate 2

22 g of the intermediate 1 and 32 g of phenol were dissolved in 20 mL of methanesulfonic acid and 20 mL of acetonitrile. While the reaction solution was heated and kept at 90° C., 0.3 mL of 3-mercaptopropionic acid was added dropwise. After stirring the mixture for 3 hours, 200 mL of acetonitrile and 100 mL of water were added, and the reaction solution was stirred for 2 hours in an ice bath. The precipitated crystals were collected by filtration, washed with methanol, and dried, and thereby 26 g of an intermediate 2 was obtained.

$^1$H-NMR (300 MHz, DMSO-d$_6$): δ2.47 ppm (s, 3H), 2.49 ppm (s, 3H), 6.61-6.67 ppm (d, 4H), 6.95-7.01 ppm (d, 4H), 7.52-7.62 ppm (m, 3H), 7.84 ppm (s, 1H), 7.93 ppm (s, 1H), 8.12-8.14 ppm (d, 1H), 9.40 ppm (bs, 2H)

Synthesis of A-27

A compound (A-27) was obtained by the same method as in the synthesis of the compound (A-1) of Synthesis Example 6, except that the intermediate 4 was changed to the intermediate 2.

$^1$H-NMR (300 MHz, DMSO-d$_6$): δ2.47 ppm (s, 3H), 2.49 ppm (s, 3H), 2.62-2.72 ppm (m, 4H), 2.80-2.90 ppm (m, 4H), 4.25-4.35 ppm (m, 8H), 5.85-6.40 ppm (m, 6H), 7.00-7.10 ppm (d, 4H), 7.20-7.30 ppm (d, 4H), 7.55-7.70 ppm (m, 3H), 7.84 ppm (s, 1H), 7.93 ppm (s, 1H), 8.16-8.22 ppm (d, 1H)

Synthesis Example 9

Synthesis of A-35

A compound (A-35) was obtained by the same method as in the synthesis of the compound (A-27) of Synthesis Example 8 except that mono(2-acryloyloxyethyl) succinate was changed to mono(2-methacryloyloxyethyl) succinate.

$^1$H-NMR (300 MHz, DMSO-d$_6$): δ1.80 ppm (s, 6H), 2.47 ppm (s, 3H), 2.49 ppm (s, 3H), 2.62-2.72 ppm (m, 4H), 2.80-2.90 ppm (m, 4H), 4.25-4.35 ppm (m, 8H), 5.58 ppm (s, 2H), 5.97 ppm (s, 2H), 7.00-7.10 ppm (d, 4H), 7.20-7.30 ppm (d, 4H), 7.55-7.70 ppm (m, 3H), 7.84 ppm (s, 1H), 7.93 ppm (s, 1H), 8.16-8.22 ppm (d, 1H)

Synthesis of Comparative Compound (Z-1)

A compound having the following structure was synthesized by the method described in JP2014-043565A. This was designated as a comparative compound Z-1.

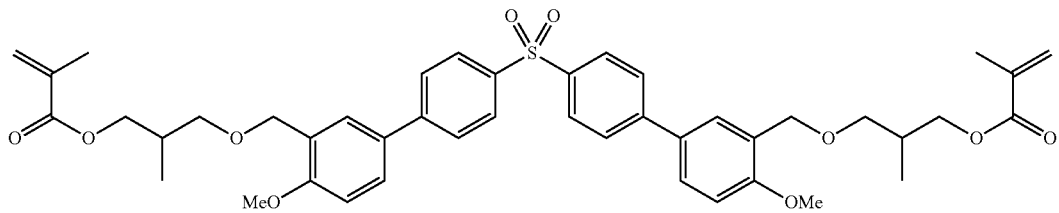

Comparative compound Z-1

Comparative Compound Z-2

N-vinylcarbazole (manufactured by Tokyo Chemical Industry Co., Ltd.) was used as a comparative compound Z-2.

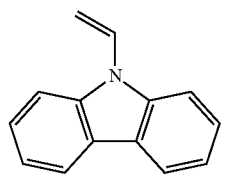

Comparative compound Z-2

Comparative Compound Z-3

The following compound was used as a comparative compound Z-3.

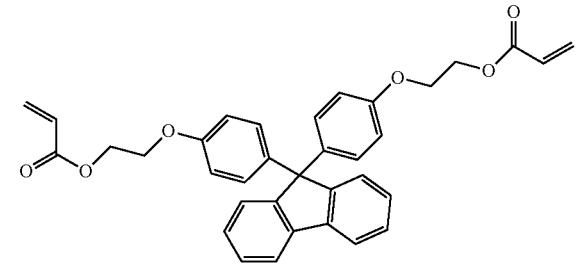

Comparative compound Z-3

The comparative compound Z-3 was synthesized according to a method described in paragraph 0097 of JP5898551B.

<Preparation of Curable Composition>

As shown in the following table, the compound represented by General Formula A (component (A)), the compound represented by General Formula B (component (B)), other components (C-1), a thermal polymerization initiator (t-butylperoxy-2-ethylhexanoate, product name: Perbutyl O (manufactured by NOF CORPORATION)), and a photopolymerization initiator (IRGACURE 819) were mixed and stirred to be uniform. Thereby, a curable composition was prepared.

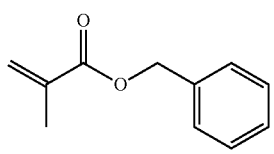

C-1

<Production of Cured Product Sample for Optical Characteristics Measurement>

The prepared curable composition was poured into a transparent circular glass mold having a diameter of 20 mm so that a thickness of the cured product was 2 mm, and was heated to 200° C. in an atmosphere having an oxygen concentration of 1% or less. Thereby, a thermally cured product was produced.

<Optical Characteristics Measurement>

A "refractive index (nd)," an "Abbe number (vd)," and a "partial dispersion ratio (θg, F)" were measured by processing the cured product obtained by the cured product sample production method (2) into a V-shaped block, and using a Kalnew precision refractometer KPR-2000 (manufactured by Shimadzu Device Corporation). The measurement was performed three times for each sample at 25° C., and an average value was taken as a measurement result.

A "refractive index (nd)" is a refractive index at a wavelength of 587.56 nm. In addition, an "Abbe number (vd)" and a "partial dispersion ratio (θg, F)" are values calculated from the refractive index measurement values at different wavelengths according to the following equations.

$$vd=(nd-1)/(nF-nC)$$

$$\theta g,F=(ng-nF)/(nF-nC)$$

Provided that nd represents a refractive index at a wavelength of 587.56 nm, nF represents a refractive index at a wavelength of 486.13 nm, nC represents a refractive index at a wavelength of 656.27 nm, and ng represents a refractive index at a wavelength of 435.83 nm.

The results are shown in Table 1.

TABLE 1

| | Resin composition | Resin composition 1 | Resin composition 2 | Resin composition 3 | Resin composition 4 | Resin composition 5 | Resin composition 6 |
|---|---|---|---|---|---|---|---|
| Component (A) | A-28 | 64.4 | | | | | |
| | VI-2 | | 64.4 | | | | |
| | III-1 | | | 64.4 | | | |
| | I-1 | | | | 64.4 | | |
| | I-24 | | | | | 64.4 | |
| | A-1 | | | | | | 64.4 |
| | A-2 | | | | | | |
| | A-27 | | | | | | |
| | A-35 | | | | | | |
| Component (B) | B-1 | | | | | | |
| | B-5 | | | | | | |
| | B-7 | 5 | 5 | 5 | 5 | 5 | 5 |
| | B-9 | | | | | | |
| | B-11 | | | | | | |
| Comparative compound | Tinuvin 99-2 | | | | | | |
| | Z-1 | | | | | | |
| | Z-2 | | | | | | |
| | Z-3 | | | | | | |
| Other components | C-1 | 29.6 | 29.6 | 29.6 | 29.6 | 29.6 | 29.6 |
| Thermal polymerization initiator | Perbutyl O | 1 | 1 | 1 | 1 | 1 | 1 |
| Photopolymerization initiator | Irg 819 | 0.1 | 0.1 | 0.1 | 0.1 | 0.1 | 0.1 |
| Total | | 100 | 100 | 100 | 100 | 100 | 100 |
| Characteristics of cured product | nd | 1.559 | 1.521 | 1.535 | 1.539 | 1.540 | 1.577 |
| | vd | 22.3 | 26.6 | 25.1 | 24.6 | 21.9 | 22.2 |
| | θg, F | 0.64 | 0.72 | 0.76 | 0.77 | 0.79 | 0.81 |

| | Resin composition | Resin composition 7 | Resin composition 8 | Resin composition 9 | Resin composition 10 | Resin composition 11 |
|---|---|---|---|---|---|---|
| Component (A) | A-28 | | | | | |
| | VI-2 | | | | | |
| | III-1 | | | | | |
| | I-1 | | | | | |
| | I-24 | | | | | |
| | A-1 | 64.4 | 64.4 | 64.4 | 64.4 | 64.4 |
| | A-2 | | | | | |
| | A-27 | | | | | |
| | A-35 | | | | | |
| Component (B) | B-1 | | | 5 | | |
| | B-5 | | | | 5 | |
| | B-7 | 3 | 1.5 | | | |
| | B-9 | | | | | 5 |
| | B-11 | | | | | |

TABLE 1-continued

|  |  |  |  |  |  |  |
|---|---|---|---|---|---|---|
| Comparative compound | Tinuvin 99-2 |  |  |  |  |  |
|  | Z-1 |  |  |  |  |  |
|  | Z-2 |  |  |  |  |  |
|  | Z-3 |  |  |  |  |  |
| Other components | C-1 | 31.6 | 33.1 | 29.6 | 29.6 | 29.6 |
| Thermal polymerization initiator | Perbutyl O | 1 | 1 | 1 | 1 | 1 |
| Photopolymerization initiator | Irg 819 | 0.1 | 0.1 | 0.1 | 0.1 | 0.1 |
| Total |  | 100 | 100 | 100 | 100 | 100 |
| Characteristics of cured product | nd | 1.575 | 1.573 | 1.572 | 1.571 | 1.579 |
|  | νd | 22.3 | 22.4 | 22.3 | 22.4 | 21.9 |
|  | θg, F | 0.81 | 0.80 | 0.80 | 0.80 | 0.82 |

|  |  | Resin composition | Resin composition 12 | Resin composition 13 | Resin composition 14 | Resin composition 15 | Resin composition 16 |
|---|---|---|---|---|---|---|---|
| Component (A) | A-28 |  |  |  |  |  |  |
|  | VI-2 |  |  |  |  |  |  |
|  | III-1 |  |  |  |  |  |  |
|  | I-1 |  |  |  |  |  |  |
|  | I-24 |  |  |  |  |  |  |
|  | A-1 |  | 64.4 | 64.4 |  |  |  |
|  | A-2 |  |  |  | 64.4 |  |  |
|  | A-27 |  |  |  |  | 64.4 |  |
|  | A-35 |  |  |  |  |  | 64.4 |
| Component (B) | B-1 |  |  |  |  |  |  |
|  | B-5 |  |  |  |  |  |  |
|  | B-7 |  |  |  | 5 | 5 | 5 |
|  | B-9 |  |  | 17.5 |  |  |  |
|  | B-11 |  | 5 |  |  |  |  |
| Comparative compound | Tinuvin 99-2 |  |  |  |  |  |  |
|  | Z-1 |  |  |  |  |  |  |
|  | Z-2 |  |  |  |  |  |  |
|  | Z-3 |  |  |  |  |  |  |
| Other components | C-1 |  | 29.6 | 17.1 | 29.6 | 29.6 | 29.6 |
| Thermal polymerization initiator | Perbutyl O |  | 1 | 1 | 1 | 1 | 1 |
| Photopolymerization initiator | Irg 819 |  | 0.1 | 0.1 | 0.1 | 0.1 | 0.1 |
| Total |  |  | 100 | 100 | 100 | 100 | 100 |
| Characteristics of cured product | nd |  | 1.578 | 1.583 | 1.581 | 1.590 | 1.588 |
|  | νd |  | 22.1 | 21.7 | 21.8 | 21.0 | 21.1 |
|  | θg, F |  | 0.81 | 0.82 | 0.82 | 0.86 | 0.86 |

|  |  | Resin composition | Comparative composition 1 | Comparative composition 2 | Comparative composition 3 | Comparative composition 4 | Comparative composition 5 |
|---|---|---|---|---|---|---|---|
| Component (A) | A-28 |  |  |  |  |  |  |
|  | VI-2 |  |  |  |  |  |  |
|  | III-1 |  |  |  |  |  |  |
|  | I-1 |  | 64.4 | 64.4 |  |  |  |
|  | I-24 |  |  |  |  |  |  |
|  | A-1 |  |  |  | 64.4 |  |  |
|  | A-2 |  |  |  |  |  |  |
|  | A-27 |  |  |  |  |  |  |
|  | A-35 |  |  |  |  |  |  |
| Component (B) | B-1 |  |  |  |  |  |  |
|  | B-5 |  |  |  |  |  |  |
|  | B-7 |  |  |  |  |  |  |
|  | B-9 |  |  |  |  | 5 | 17.5 |
|  | B-11 |  |  |  |  |  |  |
| Comparative compound | Tinuvin 99-2 |  |  | 5 |  |  |  |
|  | Z-1 |  |  |  |  | 64.4 |  |
|  | Z-2 |  |  |  |  |  | 19.3 |
|  | Z-3 |  |  |  |  |  | 45.1 |

TABLE 1-continued

| | | | | | | |
|---|---|---|---|---|---|---|
| Other components | C-1 | 34.6 | 29.6 | 34.6 | 29.6 | 17.1 |
| Thermal polymerization initiator | Perbutyl O | 1 | 1 | 1 | 1 | 1 |
| Photopolymerization initiator | Irg 819 | 0.1 | 0.1 | 0.1 | 0.1 | 0.1 |
| Total | | 100 | 100 | 100 | 100 | 100 |
| Characteristics of cured product | nd | 1.539 | 1.541 | 1.579 | 1.577 | 1.602 |
| | vd | 24.6 | 24.6 | 22.3 | 22.8 | 23.1 |
| | θg, F | 0.77 | 0.76 | 0.80 | 0.69 | 0.65 |

In the table, an amount of each component is expressed by % by mass

<Production of Compound Lenses L-1 to L-16 and Comparative Lenses R-1 to R-5>

The lenses were produced as described below with reference to the description in WO2017/115649A.

200 mg of the curable composition was injected into a molding mold whose surface was treated with chromium nitride, the entire surface of the curable composition that was not in contact with the molding mold was covered with a transparent glass lens (glass material=BK7, convex lens with a diameter of 33 mm, a center thickness of 3 mm, a radius of curvature of the surface in contact with the curable composition=44.3 mm, a radius of curvature of the surface not in contact with the curable composition=330.9 mm), and the curable composition was spread to have a diameter of 30 mm. After this state, irradiation of ultraviolet rays of 300 mJ/cm$^2$ was performed from above the glass lens using an Execure 3000 (manufactured by Hoya Corporation) as a light source. In this case, a short wavelength cut filter LU0422 (manufactured by Asahi Spectra Co., Ltd.) was disposed between the light source and the glass lens.

Next, while maintaining the state sandwiched between the molding mold and the glass lens, the temperature was raised to 200° C. while applying a pressure of 0.196 MPa (2 kgf/cm$^2$) to the curable composition. Thereafter, the cured product of the curable composition and the molding mold were separated at a speed of 0.05 mm/sec to produce a compound lens.

In addition, 25 compound lenses were respectively produced and used for evaluation.

<Production of Cemented Lenses L-14 and L-15>

In a work box purged with nitrogen, a lens adhesive was applied to one surface of a horizontally installed lens B. Next, a lens A was superimposed on the applied adhesive, and was spread out so that air bubbles did not enter. At this time, an application amount was adjusted so that a film thickness of the lens adhesive layer at the central part became 30 μm. Next, irradiation with ultraviolet rays of 300 mJ/cm$^2$ was performed from the side of the lens A using Execure 3000 (manufactured by HOYA CORPORATION) to cure the lens adhesive. Thereby, a cemented lens L-14 was obtained.

As the lens A, BK7 (a glass lens, manufactured by Ohara Corporation) was used. As the lens B, the compound lens L-4 produced above was used, and a surface on a resin layer side was used as a cemented surface. Furthermore, a cemented lens L-15 was obtained in the same manner except that the compound lens L-6 was used as the lens B.

In addition, 25 compound lenses were respectively produced and used for evaluation.

As the lens adhesive, a lens adhesive having the following composition was used.

Composition of Adhesive
Compound S-1: 70 parts by mass
Acrylic acid (2-ethylhexyl): 29 parts by mass
IRGACURE 819: 1 part by mass

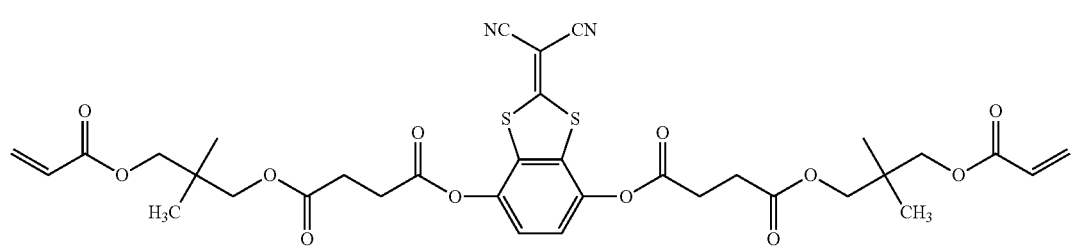

(S-1)

Synthesis of Compound S-1 (Compound $I_X$-4 Exemplified Above)
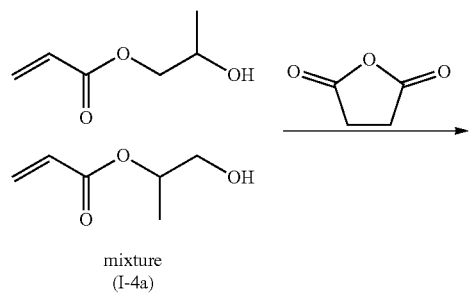
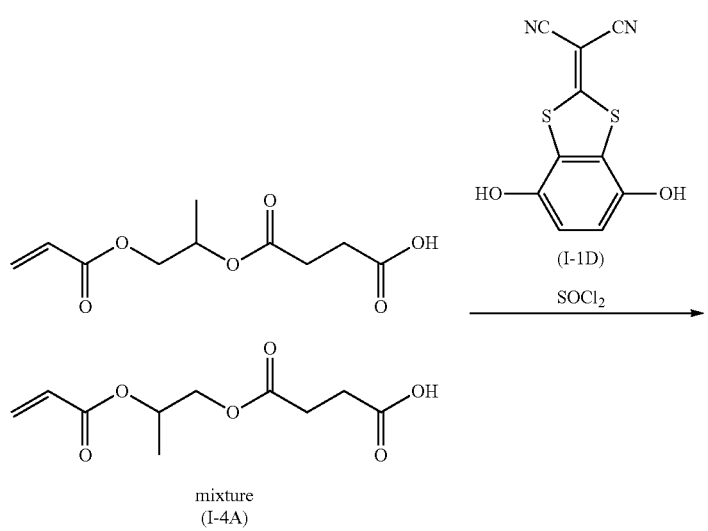
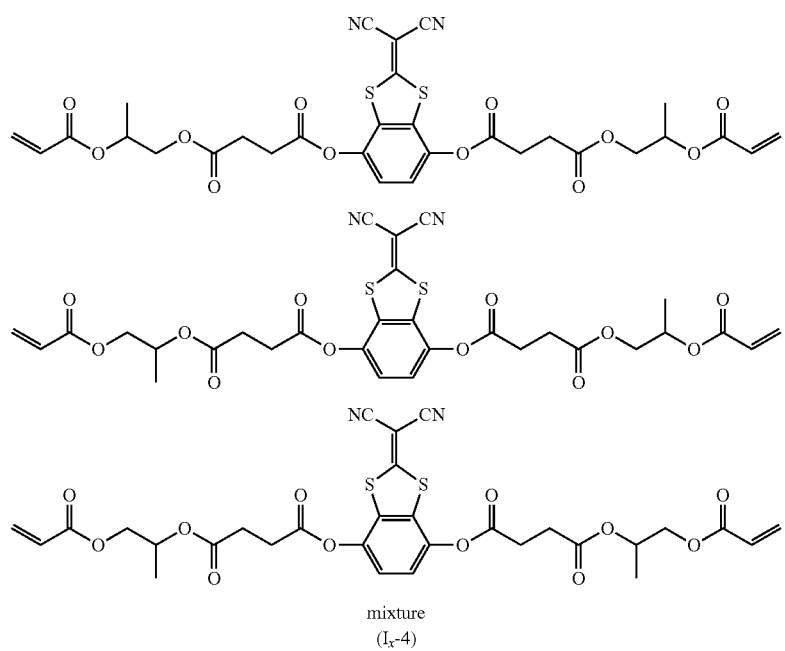

Synthesis of Compound (I-1D)

Synthesis of a compound (I-1D) was performed according to a method described in "Journal of Chemical Crystallography" (1997); 27 (9); p. 515-526.

Synthesis of Compound (I-4A)

A compound (I-4A) was synthesized according to a method for synthesizing a compound (I-4A) described in JP2016-081035A.

Synthesis of Compound (I-4$_x$)

15.5 g (67.4 mmol) of a carboxylic acid compound (I-4A), 185 mL of ethyl acetate, 46 mL of N,N-dimethylacetamide, and 60 mg of 2,6-di-t-butyl-4-methylphenol were mixed, and an internal temperature was cooled to 0° C. To the mixture, 7.75 g (65.1 mmol) of thionyl chloride was added dropwise at an internal temperature of 0° C. to 5° C. After stirring at 5° C. for 60 minutes, a solution of 6.85 g (27.6 mmol) of the compound (I-1D) and 52 mL of tetrahydrofuran (THF) was added dropwise at an internal temperature of 0° C. to 8° C.

Thereafter, 16.8 g of N,N-diisopropylethylamine was added dropwise at an internal temperature of 0° C. to 10° C. After stirring at an internal temperature of 20° C. to 25° C. for 1 hour, 40 mL of ethyl acetate, 165 mL of water, and 14 mL of concentrated hydrochloric acid were added and washed. The organic layer was washed with 140 mL of saturated saline and separated, and then washed with 100 mL of saturated saline and 10 mL of an aqueous solution of 7.5% by mass saturated sodium bicarbonate to be separated. Thereafter, concentration was performed to obtain an oily composition, which was then purified by column chromatography, and thereby a compound (I-4) (yield 85%) was obtained.

$^1$H-NMR (400 MHz, CDCl$_3$): δ (ppm) 1.25-1.35 (d, 6H), 2.78 (t, 4H), 2.95 (t, 4H), 4.10-4.35 (m, 4H), 5.25 (sext, 2H), 5.83 (d, 2H), 6.05-6.15 (m, 2H), 6.40 (d, 2H), 7.33 (s, 2H)

<Evaluation of Light Fastness of Lens>

Five lenses of each of the produced compound lens and cemented lens were irradiated with ultraviolet rays of 75 J/cm$^2$ using Execure 3000 (manufactured by HOYA CORPORATION). Before and after ultraviolet ray irradiation, ultraviolet-visible transmittance measurement of the central part of the compound lens (diameter 5 mm) was performed using a spectrophotometer UV-3100 (manufactured by Shimadzu Corporation), a decrease width in transmittance at a wavelength of 430 nm was obtained according to the following formula, and an average value of the five lenses was used as the evaluation result. The cemented lens was irradiated with ultraviolet rays from the lens A side.

Decrease width=transmittance (%) at wavelength 430 nm before ultraviolet ray irradiation−transmittance (%) at wavelength 430 nm after ultraviolet ray irradiation <Evaluation of Moisture-Heat Resistance of Lens>

The moisture-heat resistance of the produced compound lens and cemented lens was evaluated by the following method. 20 lenses of each of the lenses were stored in an environment of 50° C. and 85% humidity for 48 hours, and then the temperature was returned to room temperature. A visual evaluation was performed, an appearance inspection for cracks and peeling was performed using a microscope, and lenses that did not change before and after the test were determined as non-defective products.

A ratio of non-defective products was defined as a yield rate, and the evaluation was made according to the following criteria.

A: A yield rate was 95% or more.
B: A yield rate was 90% or more and less than 95%.
C: A yield rate was 85% or more and less than 90%.
D: A yield rate was 80% or more and less than 85%.
E: A yield rate was less than 80%.

TABLE 2

|  | Example 1 | Example 2 | Example 3 | Example 4 | Example 5 | Example 6 |
| --- | --- | --- | --- | --- | --- | --- |
| Lens | L-1 | L-2 | L-3 | L-4 | L-5 | L-6 |
| Resin composition | Resin composition 1 | Resin composition 2 | Resin composition 3 | Resin composition 4 | Resin composition 5 | Resin composition 6 |
| Form | Compound lens | Compound lens | Compound lens | Compound lens | Compound lens | Compound lens |
| Decrease width in transmittance at 430 nm | 8% | 10% | 11% | 8% | 9% | 3% |
| Evaluation of moisture-heat resistance | C | D | D | D | C | C |

|  | Example 7 | Example 8 | Example 9 | Example 10 | Example 11 |
| --- | --- | --- | --- | --- | --- |
| Lens | L-7 | L-8 | L-9 | L-10 | L-11 |
| Resin composition | Resin composition 7 | Resin composition 8 | Resin composition 9 | Resin composition 10 | Resin composition 11 |
| Form | Compound lens | Compound lens | Compound lens | Compound lens | Compound lens |
| Decrease width in transmittance at 430 nm | 5% | 9% | 8% | 10% | 4% |
| Evaluation of moisture-heat resistance | C | C | C | C | C |

|  | Example 12 | Example 13 | Example 14 | Example 15 | Example 16 |
| --- | --- | --- | --- | --- | --- |
| Lens | L-12 | L-13 | L-14 | L-15 | L-16 |
| Resin | Resin | Resin | Resin | Resin | Resin |

TABLE 2-continued

| composition | composition 12 | composition 13 | composition 14 | composition 15 | composition 16 |
|---|---|---|---|---|---|
| Form | Compound lens | Compound lens | Compound lens | Compound lens | Compound lens |
| Decrease width in transmittance at 430 nm | 5% | 3% | 2% | 2% | 2% |
| Evaluation of moisture-heat resistance | C | C | B | C | B |

| | Example 17 | Example 18 | Example 19 | Example 20 | Example 21 |
|---|---|---|---|---|---|
| Lens | L-17 | L-18 | L-19 | L-20 | L-21 |
| Resin composition | Resin composition 4 | Resin composition 6 | Resin composition 14 | Resin composition 15 | Resin composition 16 |
| Form | Cemented lens | Cemented lens | Cemented lens | Cemented lens | Cemented lens |
| Decrease width in transmittance at 430 nm | 3% | 1% | 1% | 1% | 1% |
| Evaluation of moisture-heat resistance | C | B | A | B | A |

| | Comparative Example 1 | Comparative Example 2 | Comparative Example 3 | Comparative Example 4 | Comparative Example 5 |
|---|---|---|---|---|---|
| Lens | R-1 | R-2 | R-3 | R-4 | R-5 |
| Resin composition | Comparative composition 1 | Comparative composition 2 | Comparative composition 3 | Comparative composition 4 | Comparative composition 5 |
| Form | Compound lens | Compound lens | Compound lens | Compound lens | Compound lens |
| Decrease width in transmittance at 430 nm | 39% | 27% | 34% | 29% | 28% |
| Evaluation of moisture-heat resistance | D | D | C | E | D |

What is claimed is:

1. A compound represented by General Formula (A10):

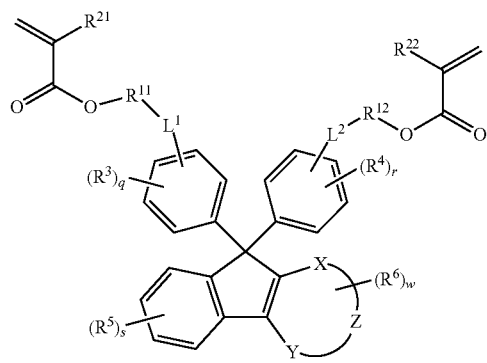

(A10)

in General Formula (A10), X and Y are each independently an oxygen atom, a sulfur atom, a nitrogen atom, or a carbon atom, and at least one of X or Y is an oxygen atom, a sulfur atom, or a nitrogen atom; Z represents an atomic group forming a 5- to 7-membered ring together with X—C=C—Y and containing at least one selected from a carbon atom or a heteroatom; and in X, Y, and Z, a hydrogen atom is bonded to a carbon atom to which $R^6$ is not bonded to form CH, $R^3$ to $R^6$ each independently represent a substituent, and q and r are each independently an integer of 0 to 4, s is an integer of 0 to 4, w is an integer of 0 or more, and a maximum number of w is a maximum number of substituents that may be substituted on the ring formed by X—C=C—Y and Z, $L^1$ and $L^2$ represent an ester bond, $R^{11}$ and $R^{12}$ each independently represent a linear alkylene group having 2 to 20 carbon atoms, or a group in which one or two or more non-adjacent —$CH_2$—'s are substituted by —O—, —C(=O)—, —OC(=O)—, —C(=O)O—, —OC(=O)O—, or —NH— in the linear alkylene group having 2 to 20 carbon atoms, and $R^{21}$ and $R^{22}$ each independently represent a hydrogen atom or a methyl group.

2. The compound according to claim 1, wherein $R^{11}$ and $R^{12}$ each independently represent a linear alkylene group having 2 to 10 carbon atoms, or a group in which one or two or more non-adjacent —$CH_2$—'s are substituted by —O—, —C(=O)—, —OC(=O)—, —C(=O)O—, —OC(=O)O—, or —NH— in a linear alkylene group having 3 to 15 carbon atoms.

3. The compound according to claim 1, wherein both -$L^1$-$R^{11}$- and -$L^2$-$R^{12}$— are —OC(=O)—$C_2H_4$—C(=O)—O—$C_2H_4$—.

4. The compound according to claim 1, which is represented by General Formula (A10-1):

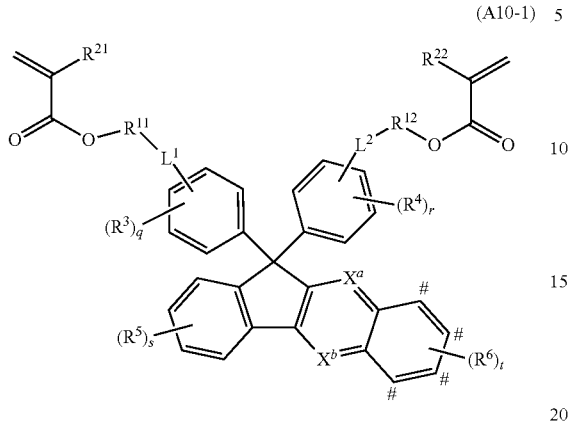

(A10-1)

in General Formula A10-1, one of $X^a$ or $X^b$ represents N and the other represents CH, or both $X^a$ and $X^b$ represent N, any one of CH's at positions # may be N, $R^3$ to $R^6$ each independently represent a substituent; and q, r, s, and t are each independently an integer of 0 to 4, $L^1$ and $L^2$ represent an ester bond, $R^{11}$ and $R^{12}$ each independently represent a linear alkylene group having 2 to 20 carbon atoms, or a group in which one or two or more non-adjacent —CH$_2$—'s are substituted by —O—, —C(=O)—, —OC(=O)—, —C(=O)O—, —OC(=O)O—, or —NH— in the linear alkylene group having 2 to 20 carbon atoms, and $R^{21}$ and $R^{22}$ each independently represent a hydrogen atom or a methyl group.

* * * * *